(12) United States Patent
Marteyn et al.

(10) Patent No.: US 10,138,280 B2
(45) Date of Patent: Nov. 27, 2018

(54) POLYPEPTIDES TARGETING GLYCOSYLATED MUC2 PROTEINS, METHODS OF SYNTHESIS, THEIR NUCLEIC ACIDS AND USES THEREOF

(71) Applicant: INSTITUT PASTEUR, Paris (FR)

(72) Inventors: Benoit Marteyn, Paris (FR);
Yves-Marie Coic, Meudon (FR);
Francoise Baleux, Paris (FR); Philippe Sansonetti, Paris (FR)

(73) Assignee: Institut Pasteur, Paris (FR)

( * ) Notice: Subject to any disclaimer, the term of this patent is extended or adjusted under 35 U.S.C. 154(b) by 12 days.

(21) Appl. No.: 15/178,049

(22) Filed: Jun. 9, 2016

(65) Prior Publication Data
US 2016/0318981 A1 Nov. 3, 2016

Related U.S. Application Data

(62) Division of application No. 14/343,588, filed as application No. PCT/EP2012/067587 on Sep. 7, 2012, now Pat. No. 9,382,299.

(30) Foreign Application Priority Data

Sep. 9, 2011 (EP) ..................................... 11290403

(51) Int. Cl.
| | | |
|---|---|---|
| C07K 14/335 | (2006.01) | |
| C12P 21/02 | (2006.01) | |
| C07K 14/195 | (2006.01) | |
| C07K 14/315 | (2006.01) | |
| C07K 7/08 | (2006.01) | |
| G01N 33/68 | (2006.01) | |

(52) U.S. Cl.
CPC .............. *C07K 14/335* (2013.01); *C07K 7/08* (2013.01); *C07K 14/195* (2013.01); *C07K 14/315* (2013.01); *C12P 21/02* (2013.01); *G01N 33/6893* (2013.01); *C07K 2319/60* (2013.01); *C07K 2319/61* (2013.01)

(58) Field of Classification Search
None
See application file for complete search history.

(56) References Cited

PUBLICATIONS

UniProt sequence Q9RGN5 (entered May 1, 2000).*
Allen et al., "The MUC2 gene product: a human intestinal mucin," The International Journal of Biochemistry and Cell Biology, vol. 30, No. 7, pp. 797-801, Jul. 1, 1998.
Bin Wang et al., "Identification of a Surface Protein from Lactobacillus reuteri JCM1081 That Adheres to Porcine Gastric Mucin and Human Enterocyte-Like HT 29 Cells," Current Microbiology, vol. 57, No. 1, Apr. 2008.
Boekhorst, Joe, et al.; Comparative analysis of proteins with a mucus-binding domain found exclusively in lactic acid bacteria: Microbiology (2006), 152; pp. 273-280; with supplementary Figure C (2 pages).
Database ENA [online] "marine metgenome partial hypothetical protein id—EB064552; SV1; linear; genomic dna; con; env; 229 BP." retrieved from EBI database accession No. EB064552, Oct. 17, 2012.
Database UniProt [Online] May 5, 2009 (May 5, 2009), « SubName : Full=Uncharacterized protein (ECI ;0000313 EMBL :EEG51799.1 », EBI access number. No. UNPROT :CODA50.
Godl et al. "The N Terminus of the MUC2 Mucin Forms Trimers That Are Held Together within a Trypsin-resistant Core Fragment". The Journal of Biological Chemistry; vol. 277, No. 49; pp. 47248-47266, 2002.

(Continued)

*Primary Examiner* — Jennifer Pitrak McDonald
*Assistant Examiner* — Tara L Martinez
(74) *Attorney, Agent, or Firm* — Arrigo, Lee, Guttman & Mouta-Bellum LLP

(57) ABSTRACT

The invention relates to polypeptides, defined through a consensus sequence, having a length from 10 to 80 amino-acid residues, and whose polypeptidic sequence comprises or consists of the consensus sequence P1($X_a$)P3($X_b$)P5($X_c$)P6($X_d$)P7 (SEQ ID NO: 1), presenting specific patterns. The polypeptides of the invention target glycosylated Muc2 proteins. The invention also relates to methods of synthesis of such polypeptides, to their nucleic acids and uses thereof. The polypeptidic sequence of the polypeptides of the invention can be part of the N-terminal sequence of a mucus-binding (MUB) domain, especially a mucus-binding (MUB) domain of several species. The invention also relates to chimeric molecule(s) comprising such polypeptides, which are labelled, and vectors, especially plasmids and population of cells or composition comprising polypeptides of the invention. Synthesis methods encompass biotechnological or chemical production. Polypeptides of the invention can be used in staining experiments, as a probe or marker for staining Muc2 protein(s) contained in mucus layer(s), to detect in vitro mucus production or mucus composition in human colon or monitoring any one of the following disease conditions: neoplasic disease(s), including mucinous carcinoma(s), gastric cancer(s) or colorectal cancer(s), especially colon cancer(s), cystic fibrosis, intestine inflammatory disease(s) such as inflammatory bowel disease (IBD) and ulcerative colitis. The invention also relates to a method for manufacturing a medicament. In a particular embodiment, use of polypeptides of the invention can be made for marking neutrophiles.

Figure 1A:

17 Claims, 43 Drawing Sheets
Specification includes a Sequence Listing.

(56) References Cited

PUBLICATIONS

International Search Report issued in application No. PCT/EP2012/067587 dated Nov. 7, 2012.
Mackenzie et al., "Crystal Structure of a Mucus-binding Protein Repeat Reveals an Unexpected Functional Immunoglobulin Binding Activity," Journal of Biological Chemistry, vol. 284, No. 47, pp. 32444-32453, Nov. 20, 2009.
Roos et al., "A high-molecular-mass cell-surface protein from Lactobacillus reuteri 1063 aderes to mucus components," Microbiology, vol. 148, No. Pt. 2, pp. 433-442, Feb. 1, 2002.
Sequence alignment run Mon Apr. 20, 2015 13:49:42, obtained online at http://www.ebi.ac.uk/Tools/psa/emboss_needle/.
Sequence alignment run Mon Apr. 20, 2015 18:03:36 obtained online at http://www.ebi.ac.uk/Tools/psa/emboss_needle/.
Sternberg et al.,"Alternative splicing of the human MUC2 gene," Archives of Biochemistry and Biophysics, vol. 421, No. 1, pp. 21-33, Jan. 1, 2004.
UniProt Q9RGN5 (Date entered into UniProt: May 1, 2000).

\* cited by examiner

*Lb. Reuteri* MucBP
*Lb. Plantarum* MucBP 200 aa
100 aa

[MucBD repeats]   #1   #2      #5   #6   #7      #12   #13
*L. Reuteri*

MucBD repeat #7

MucBP associated domain (MUBAD) or MUB₇₀

```
L. reuteri      TLTVIYTADAQKVHVQYIDGETDQMLRQD--DLDGYTDETIPYSTAEGIKKEEGDGYELF
L. gasseri      ---TVTYKANPQKITVNYIDDTTGKT-STK--DINGKSDEKSDYATKDSIAEYEKQHYDLV
L. johnsonii    ----IYSPDAQHMITYVDDTTGEILRTD--KRDGFSDQDAKYTTGDTIKQYEDQHYKLV
L. fermentum    ---TITYTADTQKGSVSVVDDTTGKTLKTD--SISGTTGSKSSYSTSGSIADYKKQGYELV
L. acidophilus  -----VVPAKDQAAVVNYVDADEDNKITSSGDLTGKAGETINYSTADTIKDLENKGYVLV
                    *   :*   * *  .   :     :        . . *.    *  . . * ::   * *

L. reuteri      KDNFPAG-EKFDNDDTNDQFYTVIFKHH-----RENVDPNHS---------SADG
L. gasseri      SDETNGSELVFDHDDKVDQVYNVHFTHH-----MTSIND--------------
L. johnsonii    SDSTKGQPLIFDHDDNVDQTYEVHLKHS-----TENVTR--------------
L. fermentum    TDGYPAD-ITFDNDDTKDQNEFVHIKHQNIQSTE---------------------
L. acidophilus  NDGFPAG-AKYDSDDNTTQIYEVYLKHGTTTTITPDKPGEPINPNDPDGPKWPDNSGE
                 *       :  .*:*   :  . :  .   .

MUCin Binding Protein (MucBP domain)

L. reuteri      TKGTKTLTETVHYKYANGTKAAEDQ-TAQVTFTRNGVLDDVTGIVAWG-KWNEASQSYKA
L. gasseri      ---TKKINETIHYYEDGTKAHDDINGQPVIFTHDGERDEVTNKEHWN-DWKSEKDSFDF
L. johnsonii    ---NDTVTRTIHYLYDNGNTAKPDK-TQTVSFNETGTKBDVTGKTTND-NDN--AQSVDS
L. fermentum    ---AKTVIETIHYQGAGNQIPADSADQSFAAVTSPVIKGYTADKAQIL-XQTVNGDSKNT
L. acidophilus  NNLSKTGTQIIHYIGAGDKTIPEDNK--QEFTFTKIMVVDNVIGKVITDGAWNVISHTFGN
                    .   **   .*.   :      :  :    .

LTSPTIAGYAPSEAVVKRSSNSDAEQG
L. reuteri      VNSPKIAGYTPDFATIEK---------
L. gasseri      VTTPSIHGYTP---------
L. johnsonii    VTTPSIIGYTP---------
L. fermentum    AQVTETRQVSTDAVTGEKTYGSW----
L. acidophilus  VDTPVIDGI-----------
```

Fig. 1C

| Synthesis strategy | Operating sequences |
|---|---|
| 1 | H-VHVQYIDGETDQMLRQDDLDGYTDETIPYSIAEGIKKFEGDGYELFKDNFPAGEKFDNDIDNQFYTVIF-OH |
| 2 | H-CVHVQYIDGETDQMLRQDDLDGYTDETIPYSIAEGIKKFEGDGYELFKDNFPAGEKFDNDIDNQFYTVIF-OH |

Fig. 5

Charge

Net Charge at pH 7 = -12.9

Hydrophobicity profile

CLUSTALW

```
1685   TLTVIYTADAQKVHVQYIDGETDQMLRQDD---LDGYTDETIPYS--TAEGIKKFEGDGY  55
2053   TLTVIYTADAQKVHVQYIDGETDQMLRQDD---LDGYTDETIPYS--TAEGIKKFEGDGY  55
1869   TLTVIYTADAQKVHVQYIDGETDQMLRQDD---LDGYTDETIPYS--TAEGIKKFEGDGY  55
2237   TLTVIYTADAQKVHVQYIDGETDQMLRQDD---LDGYTDETIPYS--TAEGIKKFEGDGY  55
1501   TLTVIYTADAQKVHVQYIDGETDQMLRQDD---LDGYTDETIPYS--TAEGIKKFEGDGY  55
2421   TLTVIYTADAQKVHVQYIDGETDQMLRQDD---LDGYTDETIPYS--TAEGIKKFEGDGY  55
1317   TYVVKYNADVQHAVTNYIDGESDETLHTDK---VNGHSDFKINYS--TADMTKQLEAKGY  55
2605   TLTVIYTADAQTAYVKYVDDTTGETLRQDD---LHGYTDETIPYS--TAEGIKKFEGDGY  55
742    --TVYYTADTQEAAINFYD-ETGHKLLDNQTIHLTGKTGEKVDRT-QADQTLADLVKQGY  56
548    -INVVYVADTQEAAISFYD-ETDHKPLNDQTIQLTGKTGEKISHT-EANQTLAKLGKQGY  57
939    --TVYYTADTQEAAINFYD-ETGHKLLDNQTIHLTGKTGEKVDRT-QADQTLAELEKQGY  56
1127   --TVVYVGNAQEAQAIFYD-ETTGKEISGTREIATGKTDETISFTKDPNEVVKELEKQGY  57
2974   --TVVYVGDPQEAQAIFYD-ETTGKEISNTREIVNGKTDETIGFTKDPNEVVKELEKQGY  57
           *  .: * .   : *   :       .   * :.*.:  :   . :  . .**

1685   ELFKDN-----FPAGEKFDNDDTNDQ-Y-VIFKHHRENVDPNHSSADGT----------- 99
2053   ELFKDN-----FPAGEKFDNDDTNDQ-Y-VIFKHHRENVDPNHSSADGT----------- 99
1869   ELFKDN-----FPAGEKFDNDDKNDQTY-VIFKHHRENVDPNHSSADGT----------- 99
2237   ELFKDN-----FPAGEKFDNDDKNDQTY-VIFKHHRENVDPNHSSADGT----------- 99
1501   ELFKDN-----FPAGEKFDNDDKNDQTY-VIFKHHRENVDPNHSSADGT----------- 99
2421   ELFKDN-----FPAGEKFDNDDKTDQTY-VIFKHHRENVDPNHSSADGT----------- 99
1317   ELFKDN-----FPAGEKFDNDDTNDQ-Y-VIFKHHRENVDPNHSSADGT----------- 99
2605   ELFKDN-----FPAGEKFDNDDKTDQTY-VIFKHHRENVDPNHSSADGT----------- 99
742    VLDKENTAK-AFPADAVYDNNDQTPQEFTIYLKIIGTTIITDATSSKAD----------- 102
548    VVDQN------TFADDATYDNDTQAPQEFTIYLKIIDTTIITDATSSKAD---------- 99
939    VLDENNTKL GFPSNAAYDDDDVKPQEFTIYLKHGMTHTDATDKNAE              102
1127   VFDKDNAKNNVFVAGTAYDKNSEVHQYFKYYLKHGHATVTPDQ         DPQKG    105
2974   VFDKDNANNNVFAACTTYDKNSEVHQYFKYYFTHATTIVPDNPKTPADVLPDNPCKNYP  117
         . .:      *  . :.        :   :.*    .   .

1685   ------KGIKTLTETVHYKYANG----TKAAEDQTAQVTFTRNGVLDDVTG-IVAWGKWN 148
2053   ------KGIKTLTETVHYKYANG----TKAAEDQTAQVTFTRNGVLDDVTG-IVAWGKWN 148
1869   ------KCIKTLTETVHYKYADC----TKAAEDQTAQVTFTRNCVLDDVTC-IVAWCKWN 148
2237   ------KGIKTLTETVHYKYADG----TKAAEDQTAQVTFTRNGVLDDVTG-IVAWGKWN 148
1501   ------KGIKTLTETVHYKYADG----TKAAEDQTAQVTFTRNGVLDDVTG-IVAWGKWN 148
2421         KGIKTLTETVHYKYADG    TKAAEDQTAQVTFTRNGVLDDVTG IVAWGKWN 148
1317   ------KGIKTLTETVHYKYADG----TKAAEDQTAQVTFTRNGVLDDVTG-IVAWGKWN 148
2605   ------KGIKTLTETVHYKYADG----TKAAEDQTAQVTFTRNGVLDDVTG-IVAWGKWN 148
742    --------QKTVSETIHYVYKDGVNANKPVADDANTTVTFKRGYTTDKVTGKIVSYDPWT 154
548    --------QKTVSETIHYVYKDGVNANKPVADDANTTVTFKRGYTTDKVTGKIVSYDPWT 151
939    --------QKIVTETIHYVYEN----NQTAKTDYTSAVDFKRGYTTDNVTHKIISYDPWM 150
1127   --------QKTVTQTTKYFYADG---TATGLADNVQTLTFKRTGDKDLVTHFVT-WPDWS 153
2974   SGVAKDDLNKTVTRTINITTPDG---KTQTIT---QKAEFTRSATVDEVTGEVT-YGPWS 170
                *  :::.*::    :              *.*    *  **   :  :  *

1685   ------EASQSYKALTSPTIAGYAPSEAVVKRSSNSDAEQG 183
2053   ------EASQSYKALTSPTIAGYAPSEAVVKRSSNSDAEQG 183
1869   ------EASQSYKALTSPTIAGYTPSEAVVKRSSNSDAEQG 183
2237   ------EASQSYKALTSPTIAGYTPSEAVVKRSSNSDAEQG 183
1501   ------EASQSYKALTSPTIAGYTPSEAVVKRSSNSDAEQG 183
2421   ------EASQSYKALTSPTIAGYTPSEAVVKRSSNSDAEQG 183
1317   ------EASQSYKALTSPTIAGYAPSEAVVKRSSNSDAEQG 183
2605   ------EASQSYKALTSPTIAGYTPSEAVVKRSSNSDAEQG 183
742    VDGKQADSKTFDAVKSPVIAGYTADQAEV----------- 183
548    VDGKQADSKTFDAVKSPVIAGYTADQAEV----------- 180
939    VS------SKKFGFVKSPAIEGYTPNHSQI---------- 174
1127   TV----AGQQTSVVTSPALKGYT----------------- 172
2974   KN    VVLES   VDVPNISGYVPSASV            192
               :   *  : **.
```

Fig. 12

***L. reuteri* mucus binding protein precursor (mub) gene, complete cds**

```
GenBank: AF120104.1 Lactobacillus reuteri ATCC 53608 CDS 121..9930
/gene="mub"
                /translation="MVGKNNNYVRESKSNEHFQRFALRKLSVGVVSVAVAAGFYLGSG
                ATAQAATTESNASAKTEQVVQQNSTSAASDSTSTSNSSAAVSTSSATPVSTESASSMT
                VSDLPASASAASDNQASAANASESSSQSASSSVASDAAATVSKDSQAASEANSQSAAD
                VETVQLPTSAANANANESQAANILGAQAVQKAANQQAPAGFTVTDPNYPAEMYKDPDA
                SHYTYWWAQSSNGEYNLVLSTDRNGDGKVYVFLLGNNNNVLGKYTVDKNKSTEVATDD
                EGDFGTVYNDGQSGVFVTSDGTWKSKFNVFDPKAGEDDGDYGSISFMIPQVETQTTTY
                VTYFDSKGNKVDKPIEVSDPVIQKGLDGQIYTTKGGKVINGYFAKEPKNAHGFMSPFG
                KQGAIYTKDWHDGLKATFTETDTKTGLMHVVVKHYYHSWGWGTWRTVKEFDLAPGQSE
                KVDYDVYKSVTIHSIYIPQTINIQYTYEKLGNLVISSDSKSFPAEDKTQYPNDKSDST
                KAGNVTIPKVAGFTPTINDKTVTNYTFNPSDYVSDLSKDINVVYVADTQEAAISFYDE
                TDHKPLNDQTIQLTGKTGEKISHTEANQTLAKLGKQGYVVDQNTFADDATYDNDTQAP
                QEFTIYLKHDTTHTDATSSKADQKTVSETIHYVYKDGVNANKPVADDANTTVTFKRGY
                TTDKVTGKIVSYDPWTVDGKQADSKTFDAVKSPVIAGYTADQAEVAAQTVTPDSQNIN
                KTVYYTADTQEAAINFYDETGHKLLDNQTIHLTGKTGEKVDRTQADQTLADLVKQGYV
                LDKENTAKAFPADAVYDNNDQTPQEFTIYLKHGTTHTDATSSKADQKTVSETIHYVYK
                DGVNANKPVADDANTTVTFKRGYTTDKVTGKIVSYDPWTVDGKQADSKTFDAVKSPVI
                AGYTADQAEVAAQTVTPDSQNINKTVYYTADTQEAAINFYDETGHKLLDNQTIHLTGK
                TGEKVDRTQADQTLAELEKQGYVLDENNTKLGFPSNAAYDDDDVKPQEFTIYLKHGMT
                HTDATDKNAEQKIVTETIHYVYENNQTAKTDYTSAVDFKRGYTTDNVTHKIISYDPWM
                VSSKKFGFVKSPAIEGYTPNHSQIDEITVTPDSKDVVKTVVYVGNAQEAQAIFYDETT
                GKEISGTREIATGKTDETISFTKDPNEVVKELEKQGYVFDKDNAKNNVFVAGTAYDKN
                SEVHQYFKYYLKHGHATVTPDQDPQKGQKTVTQTIKYEYADGTATGLADNVQTLTFKR
                TGDKDLVTHEVTWPDWSTVAGQQTSVVTSPALKGYTADTNEIPAITYHAGDSDVTYVV
                KYNADVQHAVINYIDGESDEILHTDKVNGHSDEKINYSTADMIKQLEAKGYELFKDNF
                PAGEKFDNDDTNDQFYTVIFKHHRENVDPNHSSADGTKGTKTLTETVHYKYANGTKAA
                EDQTAQVTFTRNGVLDDVTGIVAWGKWNEASQSYKALTSPTIAGYAPSEAVVKRSSNS
                DAEQGPTLTVIYTADAQKVHVQYIDGETDQMLRQDDLDGYTDETIPYSTAEGIKKFEG
                DGYELFKDNFPAGEKFDNDDKNDQTYTVIFKHHRENVDPNHSSADGTKGTKTLTETVH
                YKYADGTKAAAEDQTAQVTFTRNGVLDDVTGIVAWGKWNEASQSYKALTSPTIAGYTPS
                EAVVKRSSNSDAEQGPTLTVIYTADAQKVHVQYIDGETDQMLRQDDLDGYTDETIPYS
                TAEGIKKFEGDGYELFKDNFPAGEKFDNDDTNDQFYTVIFKHHRENVDPNHSSADGTK
                GTKTLTETVHYKYANGTKAAEDQTAQVTFTRNGVLDDVTGIVAWGKWNEASQSYKALT
                SPTIAGYAPSEAVVKRSSNSDAEQGPTLTVIYTADAQKVHVQYIDGETDQMLRQDDLD
                GYTDETIPYSTAEGIKKFEGDGYELFKDNFPAGEKFDNDDKNDQTYTVIFKHHRENVD
                PNHSSADGTKGTKTLTETVHYKYADGTKAAAEDQTAQVTFTRNGVLDDVTGIVAWGKWN
                EASQSYKALTSPTIAGYPSEAVVKRSSNSDAEQGPTLTVIYTADAQKVHVQYIDGET
                DQMLRQDDLDGYTDETIPYSTAEGIKKFEGDGYELFKDNFPAGEKFDNDDTNDQFYTV
                IFKHHRENVDPNHSSADGTKGTKTLTETVHYKYANGTKAAEDQTAQVTFTRNGVLDDV
                TGIVAWGKWNEASQSYKALTSPTIAGYAPSEAVVKRSSNSDAEQGPTLTVIYTADAQK
                VHVQYIDGETDQMLRQDDLDGYTDETIPYSTAEGIKKFEGDGYELFKDNFPAGEKFDN
                DDKNDQTYTVIFKHHRENVDPNHSSADGTKGTKTLTETVHYKYADGTKAAEDQTAQVT
                FTRNGVLDDVTGIVAWGKWNEASQSYKALTSPTIAGYTPSEAVVKRSSNSDAEQGPTL
                TVIYTADAQKVHVQYIDGETDQMLRQDDLDGYTDETIPYSTAEGIKKFEGDGYELFKD
                NFPAGEKFDNDDKTDQTYTVIFKHHRENVDPNHSSADGTKGTKTLTETVHYKYADGTK
                AAEDQTAQVTFTRNGVLDDVTGIVAWGKWNEASQSYKALTSPTIAGYTPSEAVVKRSS
                NSDAEQGPTLTVIYTADAQTAYVKYVDDTTGETLRQDDLHGYTDETIPYSTAEGIKKF
                EGDGYELFKDNFPAGEKFDNDDKTDQTYTVIFKHHRENVDPNHSSADGTKGTKTLTET
                VHYKYADGTKAAEDQTAQVTFTRNGVLDDVTGIVAWGKWNEASQSYKALTSPTIAGYT
                PSEAVVKRSSNSDAEQGPTLTVIYTADAQTAYVKYVDDTTGETLRQDDLHGYTDETIP
```

Fig. 16A

```
              YSTAEGIKKYEGDGYVLVSDGFKPGTKFGVGTPTYEVHFKHGMTHTDATDKNAEQKTV
              TETIHYVDENNQTVQPDSTTAVTFKRGYTTDNVTGKVVSYDPWTVDGNQADSKTFAAV
              PSPAVEGYTPNHQQINEFTVTPDSKDIVKTVVYVGDPQEAQAIFYDETTGKEISNTRE
              IVNGKTDETIGFTKDPNEVVKELEKQGYVFDKDNANNNVFAAGTTYDKNSEVHQYFKY
              YFTHATTIVTPDNPKTPADVLPDNPGKNYPSGVAKDDLNKTVTRTINITTPDGKTQTI
              TQKAEFTRSATVDEVTGEVTYGPWSKNVVLESVDVPNISGYVPSASVPEITVTPNDQD
              MTINITYKKLDSGKAADQGGNASNGGQATNGGSTTGQSAQNGQSGQTQNNAGAQQLPQ
              TGNANNEKGALGLASAMFAAGLGLGFGSKKKCHED"

ORIGIN
        1 ggaagattcg ctgcaattaa ctttaaagaa gttgcaacag caaatgccaa taattgttgg
       61 ttgctgaatg aatgttgatt ttttcataat gcaaaaattt taagggagag ttttagtaat
      121 atggtcggga aaaacaataa ttatgtaagg gaaagcaaat ctaatgagca ttttcaacgg
      181 tttgcgctgc gcaaactgag cgttggggtt gtctcggttg ccgttgcggc tggttttat
      241 ttaggcagtg gtgcaacagc acaggctgca actactgaat cgaatgcatc ggctaaaact
      301 gaacaggttg tgcaacagaa ctcaacttca gctgccagtg actcaacttc aacatctaat
      361 agcagtgcag ccgtgtccac aagcagtgct acgccggtaa gcaccgagtc tgcttctagc
      421 atgacggttt ctgatttgcc agcatcggcc agcgcggctt cagacaatca agcttcggct
      481 gccaatgcca gtgaaagcag tagtcagtcg gcatcaagct cagttgccag cgatgccgca
      541 gctactgtaa gcaaagactc acaggcagct agtgaagcca acagtcaaag cgctgctgat
      601 gtagaaacag tacagttgcc aacgtcagcc gctaatgcca atgctaatga aagccaagca
      661 gccaatattt tgggtgctca agctgttcaa aaggctgcca atcaacaggc gccagccgga
      721 tttacggtta ctgacccaaa ttatccggca gaaatgtata aagatccaga tgccagtcac
      781 tatacctact ggtgggcaca aagctcgaat ggcgagtata acctggttct ttcaactgat
      841 cggaatggtg atggcaaggt ttatgtcttc ttgctgggca acaataataa tgttttaggt
      901 aagtacacgg ttgataaaaa taaatcaaca gaagtagcta ctgatgacga gggagatttt
      961 ggcacagttt acaatgatgg tcagtcaggt gtctttgtta cttctgatgg tacctggaag
     1021 tcaaagttca acgttttttga ccctaaggcg ggcgaggatg atggagacta tggcagtatt
     1081 agtttcatga tcccacaagt agaaacgcag acgacgactt acgttactta ttttgatagc
     1141 aagggtaaca aggtcgataa accaatcgag gtcagtgacc ctgtcattca aaaaggtctg
     1201 gatggtcaaa tctatacgac aaagggtggc aaagtaatca atggctattt tgccaaagag
     1261 ccaaaaaatg cccatggctt catgtcgcca tttggcaagc agggtgcaat ctacactaaa
     1321 gattggcatg atgggcttaa agccacctt accgaaactg ataccaagac cggcttgatg
     1381 catgttgttg tgaaacatta ttatcatagt tgggttggg gaacttggcg gacagtaaaa
     1441 gagtttgatc ttgccccagg tcaatcagag aaagttgact atgatgtcta taaatcagtt
     1501 actattcaca gcatctacat tccacagacg atcaacattc aatacaccta tgaaaagctg
     1561 ggcaatctgg tcatcagttc tgacagcaag tccttcccag ctgaagtaa gactcaatat
     1621 ccaaatgata agtctgactc aaccaaggcc ggtaatgtta caattccaaa ggtagccggc
     1681 tttacgccaa cgatcaatga caagacggtg acaaactaca cgtttaaccc ttctgattac
     1741 gtcagcgatc tgagtaagga cattaatgtt gtttatgtag ctgacacgca agaagctgcc
     1801 atcagcttct atgacgagac agaccacaag ccactgaatg accaaacgat tcagctgact
     1861 ggcaagactg gtgaaagat cagccatacc gaagctaatc aaacactggc taagctggga
     1921 aagcaaggct atgttgtcga ccagaatact tttgctgatg atgcaacgta tgacaacgat
     1981 acgcaagcac cacaagagtt tacgatctac ctcaagcatg atacgaccca tactgacgca
     2041 actagctcaa aggcagatca aaagaccgtc agcgaaacga ttcactacgt ctacaaagat
     2101 ggggtcaacg ctaataagcc ggtagcttga tgcgctaata caacggttac cttcaaacgc
     2161 ggctacacga ctgacaaagt tacgggaaag attgtttcct atgatccttg gacggttgat
     2221 ggcaagcaag ccgacagcaa gacgtttgat gccgtcaaga gtccagtcat tgctggttac
     2281 acggccgatc aagcagaagt tgccgctcca aggtaacgc cagattccaa aaatattaac
     2341 aagacagttt actataccgc tgacacgcaa gaagctgcca tcaacttcta tgacgagaca
     2401 ggccacaagc tgttagataa ccaaacgatt catttgactg gcaagaccgg tgaaaaggta
     2461 gaccggacgc aagcggacca gacgttggct gatctggtaa agcaaggcta tgttttggat
     2521 aaagaaaaca cggccaaggc attcccagct gacgcggtat atgacaacaa tgaccaaacg
```

Fig. 16B

```
2581 ccacaagagt ttacgatcta cctcaagcat ggtacgaccc atactgacgc aaccagctca
2641 aaggcagatc aaaagaccgt cagcgaaacg attcactacg tctacaaaga tggggtcaac
2701 gctaataagc cggtagctga tgacgctaat acaacggtta ccttcaaacg cggctacacg
2761 actgacaaag ttacgggaaa gattgtttcc tatgatcctt ggacggttga tggcaagcaa
2821 gccgacagca agacgtttga tgccgtcaag agtccagtca ttgctggtta cacggccgat
2881 caagcagaag ttgccgctca aacggtaacg ccagattccc aaaatattaa caagacagtt
2941 tactataccg ctgacacgca agaagctgcc atcaacttct atgacgagac aggccacaag
3001 ctgttagata accaaacgat tcatctgact ggcaagactg gtgaaaaggt tgatcggacg
3061 caagcggacc agacgctggc tgaactggaa aaacaaggct acgttctgga tgagaataac
3121 actaaactgg gattcccatc caatgcagcg tatgacgatg atgacgttaa gccacaagag
3181 tttacgatct atctgaagca tggcatgacg cataccgatg caaccgacaa gaatgctgaa
3241 caaaagattg ttacggaaac gattcactac gtttacgaaa acaaccagac tgctaagaca
3301 gactacacgt cagcggttga ctttaagcgc ggctacacga ctgacaacgt tacgcataag
3361 attatttcct acgatccatg gatggtatcc agcaagaagt ttggtttcgt aaagagtcca
3421 gccattgaag gctacacgcc aaaccattcg cagattgatg aaatcactgt tacgccagat
3481 tcaaaagacg tcgtcaagac ggtggtttat gttgggaatg cccaagaagc ccaagccatc
3541 ttctatgatg aaacgacggg caaagaaatc agtgggacac gtgaaattgc aactggcaag
3601 actgatgaaa cgatcagctt taccaaggat ccaaatgaag tcgttaagga actcgaaaag
3661 cagggttacg tttttgacaa ggataacgct aagaataatg tctttgtcgc tggaacggcc
3721 tacgacaaga attccgaagt tcaccaatac ttcaagtact acctgaagca cggacatgcg
3781 acggtaacgc cagaccaaga tccacaaaaa ggtcaaaaga cggttacaca gacaattaag
3841 tacgaatacg ctgatggcac ggcaactggt ttggctgata atgtgcaaac cttgacgttc
3901 aagcgtacag gtgacaagga tctcgttact catgaagtaa cctggccaga ctggtcaacg
3961 gttgccggtc aacaaaccag tgttgtaacc agtccagctc tcaagggcta cactgctgat
4021 accaacgaaa ttccagccat tacctaccat gctggtgaca gtgatgttac ttatgttgtt
4081 aagtacaatg ccgatgttca acatgctgtt atcaattaca ttgatggcga aagtgatgag
4141 atactgcaca ctgataaggt taatgccac tctgacgaaa agatcaacta cagcactgct
4201 gatatgatca aacagttgga agccaagggt tatgaactgt tcaaggacaa cttcccagct
4261 ggtgagaagt tcgataacga tgacaccaac gatcaattct acacggtaat cttcaagcac
4321 catcgtgaaa acgttgatcc aaaccactcc tcggctgacg gcacgaaggg tacgaagacg
4381 ctgacggaaa cggttcacta caagtacgct aatggcacca aggcggctga agatcagacg
4441 gctcaggtaa cgtttacgcg gaacggtgtc ctggatgacg ttacgggtat cgtggcctgg
4501 ggcaagtgga acgaagccag ccagagctac aaggctttga cttcaccaac gattgccggc
4561 tacgcgccaa gcgaagcggt ggtaaagcgc agttccaaca gcgatgccga acaaggccca
4621 acgcttacgg tcatttacac ggctgatgcc caaaaggttc acgttcaata cattgatggt
4681 gaaactgacc agatgctgcg tcaggatgat ttggacggct acacggatga acgattcct
4741 tacagcacgg ctgaaggcat caagaagttt gaaggcgacg gttatgaact gttcaaggac
4801 aacttcccag ctggtgagaa gttcgataac gatgacaaga atgaccaaac ctacacggta
4861 atcttcaagc accatcgtga aaacgttgat ccaaaccact cctcggctga tggcacgaag
4921 ggtacgaaga cgctgacgga aacggttcac tacaagtacg cagatgctac caaggccgct
4981 gaagatcaga cggctcaggt aacgtttacg cggaacggtg tcctggatga cgttacgggt
5041 atcgtggcct ggggcaagtg gaacgaagcc agccagagct acaaggcttt gacttcacca
5101 acgattgccg gctacacgcc aagcgaagcg gtggtaaagc gcagttccaa cagcgatgcc
5161 gaacaaggcc caacgcttac ggtcatctac acggctgatg cccaaaaggt tcacgttcaa
5221 tacattgatg gtgaaactga ccagatgctg cgtcaggatg atttggacgg ctacacggat
5281 gaaacgattc cttacagcac ggctgaaggc atcaagaagt ttgaaggcga cggttatgaa
5341 ctgttcaagg acaacttccc agctggtgag aagttcgata acgatgacac caacgatcaa
5401 ttctacacgg taatcttcaa gcaccatcgt gaaaacgttg atccaaacca ctcctcggct
5461 gatggcacga agggtacgaa gacgctgacg gaaacggttc actacaagta cgctaatggc
5521 accaaggcgg ctgaagatca gacggctcag gtaacgttta cgcggaacgg tgtcctggat
5581 gacgttacgg gtatcgtggc ctggggcaag tggaacgaag ccagccagag ctacaaggct
5641 ttgacttcac caacgattgc cggctacgcg ccaagcgaag cggtggtaaa gcgcagttcc
5701 aacagcgatg ccgaacaagg cccaacgctt acggtcattt acacggctga tgcccaaaag
5761 gttcacgttc aatacattga tggtgaaact gaccagatgc tgcgtcagga tgatttggac
5821 ggctacacgg atgaaacgat tccttacagc acggctgaag gcatcaagaa gtttgaaggc
5881 gacggttatg aactgttcaa ggacaacttc ccagctggtg agaagttcga taacgatgac
```

Fig. 16C

```
5941 aagaatgacc aaacctacac ggtaatcttc aagcaccatc gtgaaaacgt tgatccaaac
6001 cactcctcgg ctgatggcac gaagggtacg aagacgctga cggaaacggt tcactacaag
6061 tacgcagatg gtaccaaggc cgctgaagat cagacggctc aggtaacgtt tacgcggaac
6121 ggtgtcctgg atgacgttac gggtatcgtg gcctggggca agtggaacga agccagccag
6181 agctacaagg ctttgacttc accaacgatt gccggctaca cgccaagcga agcggtggta
6241 aagcgcagtt ccaacagcga tgccgaacaa ggcccaacgc ttacggtcat ctacacggct
6301 gatgcccaaa aggttcacgt tcaatacatt gatggtgaaa ctgaccagat gctgcgtcag
6361 gatgatttgg acggctacac ggatgaaacg attccttaca gcacggctga aggcatcaag
6421 aagtttgaag gcgacggtta tgaactgttc aaggacaact tcccagctgg tgagaagttc
6481 gataacgatg acaccaacga tcaattctac acggtaatct tcaagcacca tcgtgaaaac
6541 gttgatccaa accactcctc ggctgatggc acgaagggta cgaagacgct gacggaaacg
6601 gttcactaca agtacgctaa tggcaccaag gcggctgaag atcagacggc tcaggtaacg
6661 tttacgcgga acggtgtcct ggatgacgtt acgggtatcg tggcctgggg caagtggaac
6721 gaagccagcc agagctacaa ggctttgact tcaccaacga ttgccggcta cgcgccaagc
6781 gaagcggtgg taaagcgcag ttccaacagc gatgccgaac aaggcccaac gcttacggtc
6841 atctacacgg ctgatgccca aaaggttcac gttcaataca ttgatggtga aactgaccag
6901 atgctgcgtc aggatgattt ggacggctac acggatgaaa cgattcctta cagcacggct
6961 gaaggcatca agaagtttga aggcgacggt tatgaactgt tcaaggacaa cttcccagct
7021 ggtgagaagt tcgataacga tgacaagaat gaccaaacct acacggtaat cttcaagcac
7081 catcgtgaaa acgttgatcc aaaccactcc tcggctgatg gcacgaaggg tacgaagacg
7141 ctgacggaaa cggttcacta caagtacgca gatggtacca aggccgctga agatcagacg
7201 gctcaggtaa cgtttacgcg gaacggtgtc ctggatgacg ttacgggtat cgtggcctgg
7261 ggcaagtgga acgaagccag ccagagctac aaggctttga cttcaccaac gattgccggc
7321 tacacgccaa gcgaagcggt ggtaaagcgc agttccaaca gcgatgccga acaaggccca
7381 acgcttacgg tcatctacac ggctgatgcc caaaaggttc acgttcaata cattgatggt
7441 gaaactgacc agatgctgcg tcaggatgat ttggacggct acacggatga aacgattcct
7501 tacagcacgg ctgaaggcat caagaagttt gaaggcgacg gttatgaact gttcaaggac
7561 aacttcccag ctggtgagaa gttcgacaac gatgacaaga ctgaccaaac ctacacggta
7621 atcttcaagc accatcgtga aaacgttgat ccaaaccact cctcggctga cggcacgaaa
7681 ggtacgaaga cgctgacgga aacggttcac tacaagtacg cagatggtac caaggccgct
7741 gaagatcaga cggctcaggt aacgtttacg cggaacggtg tcctggatga cgttacgggt
7801 atcgtggcct ggggcaagtg gaacgaagcc agccaaagct acaaggctct gacttcacca
7861 acgattgccg gctacacgcc aagtgaagcg gtagtaaagc gcagttccaa cagcgatgcc
7921 gaacaaggcc caacgcttac ggtcatctac acggctgatg cccaaacagc ctacgtcaag
7981 tacgttgatg acacgactgg cgagacgctg cgtcaagacg atctgcacgg ctacacggat
8041 gaaacgattc cttacagcac ggctgaaggc atcaagaagt ttgaaggcga cggttatgaa
8101 ctgttcaagg acaacttccc agctggtgag aagttcgaca acgatgacaa gactgaccaa
8161 acctacacgg taatcttcaa gcaccatcgt gaaaacgttg atccaaacca ctcctcggct
8221 gacggcacga aaggtacgaa gacgctgacg gaaacggttc actacaagta cgcagatggt
8281 accaaggccg ctgaagatca gacggctcag gtaacgttta cgcggaacgg tgtcctggat
8341 gacgttacgg gtatcgtggc ctggggcaag tggaacgaag ccagccaaag ctacaaggct
8401 ctgacttcac caacgattgc cggctacacg ccaagtgaag cggtagtaaa gcgcagttcc
8461 aacagcgatg ccgaacaagg cccaacgctt acggtcatct acacggctga tgcccaaaca
8521 gcctacgtca agtacgttga tgacacgact ggcgagacgc tgcgtcaaga cgatctgcac
8581 ggctacacgg atgaaacgat tccatacagc acggctgaag gcatcaagaa gtacgaaggc
8641 gacggctacg ttctggtatc ggacggcttt aagccaggta ctaagttcgg tgttggcacg
8701 ccaacctatg aagttcactt caagcatggc atgacgcata ccgatgcaac cgacaagaat
8761 gctgaacaaa agacggttac ggaaacgatt cactacgttg acgaaaacaa ccaaaccgtt
8821 cagccagact ccacgacagc agtaaccttc aagcgcgatg acacgaccga taacgttacc
8881 ggcaaggttg tttcctacga tccatggacg gttgatggta atcaggctga cagtaagaca
8941 tttgctgccg tacctagccc agcagtcgaa ggttacacgc aaaccacca gcaaattaac
9001 gaattcaccg ttacgccaga ttcaaaagac attgtcaaga cggtcgttta tgttggtgat
9061 ccccaagaag ctcaagccat cttctatgat gaaacaacgg gcaaggaaat cagcaacacg
9121 cgtgaaatcg taaatggcaa gactgatgaa acgatcggct ttaccaagga tccaaatgaa
9181 gtcgtcaagg aactcgaaaa gcaaggttat gtctttgata aggacaatgc taataacaat
9241 gtctttgctg ccggcacgac ctacgacaag aattctgaag ttcaccaata cttcaagtac
```

Fig. 16D

```
9301 tacttcacgc acgctacgac gatcgttacg ccagacaatc caaagacgcc ggctgatgta
9361 ttgccggaca accctggcaa gaattacccg agcggtgttg ccaaggatga tctgaacaag
9421 accgttacgc ggacgatcaa cattacgacg ccagatggca agacacagac gatcacgcag
9481 aaggctgaat ttacgcggag tgcaacggtt gatgaggtta ccggtgaagt aacttatgga
9541 ccatggtcga agaatgtcgt tttggaaagc gttgacgtac caaacatttc tggatacgtg
9601 ccatctgcat ccgttccaga aattacggtt acgccaaatg atcaagacat gacgatcaac
9661 atcacctaca agaagcttga ttctggcaag gcagctgacc aaggcggcaa tgcttccaat
9721 ggtggtcaag caacgaatgg cggttcaacg actggtcaat ccgctcaaaa cggccagtca
9781 ggtcaaaccc aaaacaatgc tggtgctcaa caattgccac aaactggtaa cgccaacaat
9841 gaaaagggcg cactgggatt ggcaagcgca atgttcgccg ctggtcttgg cctgggcttt
9901 ggctcaaaga agaagtgtca cgaagactag atgaaacaat aaaatagatt catcacagat
9961 aaaaaagact caacctttga tttttcaaag gttgagcctt tttgtctttt ttcgcaaaga
```

Fig. 16E

Fig. 17

| Name | SEQ ID N° | |
|------|-----------|---|
| MUB40-1 | 62 | CTAEGIKKFEGDGYELFKDNFPAGEKFDNDD<u>TNDQFYTVIF</u> |
| MUB40-2 | 63 | CGYTDETIPYSTAEGIKKFEGDGYELFKDNFPAGEKF<u>DNDD</u> |
| MUB40-3 | 64 | CDQMLRQDDLDGYTDETIPYSTAEGIKKFEGDGYELFKDNF |
| MUB40-4 | 65 | CVHVQYIDGETDQMLRQDDLDGYTDETIPY<u>STAEGIKKFEG</u> |

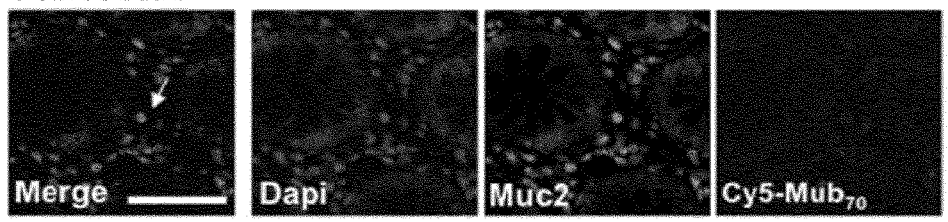
Fig. 23

Healthy colon (control)

Colonic mucinous carcinoma

*Stable cell line:*

S2/DeSNAPuniv-MUB70

```
PATTERNS :                       P8            P9       P10
MUB40-1            CTAEGIKKFEGDGYELFKDNF--PAGEKFDNDDTNDQFYTVIF  41
L. reuteri LPXTG   STADQIKQLEAQGYVLVSDGF--PAGAVFDNDDNTTQTYTVVL  41
L. fermentum       STAATIKQLEDQGYVLVSNGF--PAGAVFDNDDNTTQTYTVVL  41
L. acidophilus     STADTIKDLENKGYVLVNDGF--PAGAKYDSDDNTTQIYTVVL  41
L. crispatus       STKSTIADLENKGYVLVNDGF--PAGAKFDSDDNTTQIFTVVL  41
L. johnsonii       STASTIEELENKGYVLVSDGF--PAGATFDNDDNTTQIYTVVL  41
L. hominis         STQSTITSLENQGYELVHDGF--PTGATYDNDDNTTQTYTVVL  41
L. gasseri         STADQIKKLINQGYVLKNDGF--PAGAVFDNDDSKNQVFYVDF  41
L. mucosae         STAEGIKKFEGDGYELFKDNF--PAGEKFDNDDANDQTYTVIF  41
S. SC150           STAERIKHYQDLGYVLVTDGY--PAGTTFDLDSTVDQAWTVSF  41
S. salivarius      -TAERIKHYQDLGYALVTDGY--PAGASFDLDSTVDQAWTVSF  40
L. garviae         -TSGSIADYKKHGYELVTDGY--PADLTFDNDDTTDQNFTV--  38
Leunostoc          STSGNIADYKKHGYELVTDGY--PADLTFDNDDKTDQNFTV--  39
L. coryniformis    -TSGNIADYKKQGYELVTDGY--PADLTFDNDDTTDQNFTV--  38
S. cristatus       STASRIEQLKQAGYTLVSDGFTQPNGQKFDNDKTKDQTWTVVV  43
Weissella          -TADRIKAYEAQGYTLVSDDF--PADFQFDRDDATEQKFEV-  38
                    *    *       ** *   :.:   *  . :* *.   * : *
```

Fig. 32

POLYPEPTIDES TARGETING GLYCOSYLATED MUC2 PROTEINS, METHODS OF SYNTHESIS, THEIR NUCLEIC ACIDS AND USES THEREOF

CROSS REFERENCE TO RELATED APPLICATIONS

This application is a divisional of U.S. application Ser. No. 14/343,588, filed Jun. 9, 2014; which is a national stage entry of PCT/EP2012/067587, filed Sep. 7, 2012; which claims priority to EPO Application No. 11290403.2, filed Sep. 9, 2011. The disclosures of all prior applications are incorporated by reference herein in their entirety.

SEQUENCE LISTING

The instant application contains a Sequence Listing which has been submitted electronically in ASCII format and is hereby incorporated by reference in its entirety. Said ASCII copy, created on Jun. 9, 2014, is named seqlisting.txt and is 148,084 bytes in size.

The invention relates to isolated polypeptide(s) interacting with glycosylated Muc2 proteins in mucus layers of various biological tissues, especially colonic tissue. The invention also relates to a method for synthesizing such polypeptide(s) via chemical synthesis (i.e. involving solid phase synthesis) or via biotechnological production.

Therefore, the invention also relates to nucleic acid molecule(s) encoding polypeptide(s) of the invention, as well as nucleic acid delivery systems such as vectors and cells or populations of cells comprising nucleic acid molecule(s) or vector(s) in relation with the invention.

The invention also relates to composition(s) comprising the same, in particular to pharmaceutical composition(s) including if necessary carrier(s) or adjuvant(s).

The invention may be used for staining cell(s) in in vivo, ex vivo, especially in vitro, experiments, in particular in live microscopy experiments.

According to a particular embodiment, the molecule(s) comprising a polypeptide of the invention are used as probe(s) for staining mucus potentially containing Muc2 protein(s), especially, but not exclusively, colonic mucus produced by eukaryotic cell(s).

Mucus production or composition in animal or human body might be modified as a result of physiological events as well as a result of several disease conditions such as neoplasic disease(s), non-limitatively including mucinous carcinoma(s), gastric cancer(s) or colorectal cancer(s), especially colon cancer(s), or diseases such as cystic fibrosis or intestine inflammatory disease(s) such as inflammatory bowel disease (IBD) and ulcerative colitis.

In addition to the possibility to use the claimed molecule(s) for immunostaining fixed cells, and according to another particular embodiment, the molecule(s) of the invention can also be used as a marker of degranulation event(s), especially in living neutrophiles.

The human gastro-intestinal mucus layer establishes a physical barrier between the luminal content and the epithelial surface. This layer provides efficient protection against luminal aggressions [1] and is continuously removed (enzymatic destruction and mechanical shearing, i.e. peristaltism) and renewed through the secretory activity of epithelial goblet cells [2]. It was recently suggested that the mucus layer allows constitution of an oxygen gradient diffusing from the intestinal epithelium into the lumen [3] even though no quantification was yet achieved. This gradient plays a critical role in *Shigella* virulence modulation in the vicinity of the intestinal epithelial barrier, and possibly controls the virulence of other pathogens in addition to keeping strictly anaerobic bacteria away from the vicinity of the epithelium [4]. In vivo observations are a prerequisite for oxygen detection in this environment. In order to study this largely unexplored microenvironment at epithelial interface using emerging live imaging techniques (two-photons microscopy, fluorescent life-time imaging (FLIM) and high resolution microscopy (PALM and STORM)), it is required to develop specific, non-toxic and non-destructive colonic mucus fluorescent marker(s).

The colonic mucus is composed of two distinct layers; a firmly adherent layer associated to the epithelial surface and a loosely, more fluid, adherent one. The later is probably the result of bacterial degradation and proteolysis [5]. It is composed of 95% water and 5% mucin glycoprotein molecules, salt, immunoglobulins (IgA and IgG) and trefoil peptides [6]. Among secreted mucins, the main gel forming molecules are Muc2, Muc5ac, Muc5b and Muc6 (expressed from chromosome 11p15.5) [7], Muc2 is the predominant mucin in the colonic mucus layer and is highly glycosylated, allowing its protection from proteolysis in the lumen [8] [9] [10] [11]. Muc2 shows differential glycosylation profiles in the small intestine (ileum) and in the large intestine (colon) respectively enriched in sialylated and sulfated oligosaccharide species [9] [12]. Mucus production and composition modulations are commonly observed in the major inflammatory bowel diseases (IBD) like Crohn disease [13] [14] and ulcerative colitis [15]. Specifically, Muc2 expression is upregulated in malignant tumors of a broad range of organs [16] including lung [17], stomach [18] [19], breast [20], prostate [21], bile ducts [22] and colon [23]. Detecting the nature and amount of mucus is important to envision the diagnostic and prognosis of various pathological conditions.

Part of the process of identifying a molecule able to specifically bind human colonic mucus, the mucus adhesion properties of commensal bacteria were observed. These microorganisms, such as *Lactobacillus* spp, express cell-surface proteins named Mucus binding proteins (MucBP, PFAM PF06458) that are involved in intestinal mucus adhesion. As an example, in the human intestine, *Lactobacillus reuteri* (*L. reuteri*) has been identified as an inhabitant of the ileum and colon loosely adherent to the mucus layer [24]. The MucBP protein family is characterized by the presence of well-conserved mucin binding domains (MucBD) expressed as repeats in many cell-surface MucBP of *L. reuteri* [25] [26]. Considering that there is a need for tools suitable for mucus observation in various pathological situations, in particular for mucus observation in specific intestine compartments affected by such pathological situations, the inventors have identified in several bacteria, regions whose amino-acid sequences may be used to prepare polypeptides useful for mucus observation.

Through this study, novel binding properties of *L. reuteri* Mucus Binding Proteins to human colonic mucus were characterized. It was demonstrated that the considered domain of interest binds to mucus proteins independently of the previous characterized MUB domain. This domain is a novel MucBD of 70 amino acids length, hereafter named $MUB_{70}$, which can be individualized as a polypeptide able to oligomerize and to specifically bind the glycosylated moiety of Muc2.

Therefore, the invention relates to a polypeptide having a length from 10 or from 17 to 80 amino-acid residues and whose polypeptidic sequence comprises or consists of the consensus sequence $P1(X_a)P3(X_b)P5(X_c)P6(X_d)P7$ (SEQ ID NO: 1) disclosing, from N-terminal to C-terminal ends, patterns P1, P3, P5, P6 and P7, which are defined as follows:

P1 represents the amino-acid sequence VXYXD/N, where X represents any amino-acid,
P3 represents the amino-acid sequence GY,
P5 represents the amino-acid sequence F/YD,
P6 represents amino-acid residue D, and
P7 represents amino-acid residue Q;

and wherein said patterns are further characterized by spacer amino-acid segments $(X_a)$, $(X_b)$, $(X_c)$ and $(X_d)$ containing respectively a, b, c and d numbers of any amino-acid residue(s) which are defined as follows:

a ranges from 2 to 33,
b ranges from 2 to 11,
c ranges from 1 to 2,
d ranges from 1 to 3;

and wherein said polypeptide interacts with glycosylated Muc2 protein(s), in particular interacts with sulfated moieties of glycosylated Muc2 protein, of human colonic mucus or human intestinal mucus.

The consensus sequence of SEQ ID NO: 1 can also be written: VXYXD/N$(X_a)$ GY$(X_b)$ FND$(X_c)$D$(X_d)$Q, with spacer amino-acid segments $(X_a)$, $(X_b)$, $(X_c)$ and $(X_d)$ as defined above.

According to a particular preferred embodiment, the polypeptidic sequence of a polypeptide of the invention comprises or consists of the consensus sequence P1$(X_m)$P2$(X_n)$P3XP4$(X_p)$P5$(X_q)$P6$(X_r)$P7$X_3$P8 (SEQ ID NO: 2), X being any amino-acid residue, said consensus sequence disclosing, from N-terminal to C-terminal ends, patterns P1, P2, P3, P4, P5, P6, P7 and P8, which are defined as follows:

P1 represents the amino-acid sequence VXYXD/N, where X represents any amino-acid,
P2 represents the amino-acid sequence YS/TT,
P3 represents the amino-acid sequence GY,
P4 represents amino-acid residue L,
P5 represents the amino-acid sequence F/YD,
P6 represents amino-acid residue D,
P7 represents amino-acid residue Q, and
P8 represents amino-acid residue V, and wherein said patterns are further characterized by spacer amino-acid segments $(X_m)$, $(X_c)$, $(X_p)$, $(X_q)$ and $(X_1)$ containing respectively m, n, p, q and r numbers of any amino-acid residue(s) which are defined as follows:

m ranges from 1 to 23,
n and p range from 1 to 10,
q is 1 or 2,
r ranges from 1 to 3.

Consequently, the consensus sequence identified under consensus sequence (SEQ ID NO: 2) can also be written VXYXD/N$(X_m)$YS/TT$(X_n)$GYXL$(X_p)$FND$(X_q)$D$(X_r)$Q$X_3$V, wherein X is a symbol representing any amino-acid, including modified or non-conventional amino-acids, said symbol X being, when necessary, followed by a subscript number indicating the number of amino-acid residues incorporated into the consensus sequence. The absence of subscript number indicates that only one amino-acid residue is incorporated. The same abbreviations are generally used for the purpose of the present disclosure, unless differently specified.

In the consensus sequences disclosed above and more generally in the amino-acid sequences disclosed herein, the symbol "/" inserted between two amino-acid residues means that any of these two amino-acid residues is to be found in a polypeptide of the invention encompassed by consensus sequences disclosed herein, as an alternative. As a consequence, a symbol such as "X/X" represents the presence of only one amino-acid residue having one or the other proposed nature. A symbol such as "D/N" represents only one amino-acid residue chosen among amino-acid D and amino-acid N. Conventional abbreviations are used herein, with respect to the single letter amino-acids alphabet. Parenthesis symbols "( )" are used to separate several positions within a consensus sequence, when alternatives are possible for two consecutive positions within said consensus sequence.

By a "pattern", it is meant an amino-acid residue or a series of amino-acid residues that are to be found substantially unchanged, in their nature and/or sequence(s) and/or position(s), within all polypeptides encompassed by the consensus sequences disclosed above. The described patterns are thus further characterized, as a whole, by the spacer segments "Xi" providing a determined distance (expressed as a number of amino-acids) between especially two of them. The consensus sequences disclosed herein were identified starting from sequence alignments performed by the inventors, as exemplified within the present disclosure, through conventional alignment methods or algorithms.

According to a particular embodiment, a polypeptide of the invention has a length from 17 to 80 amino-acid residues and is selected from:

i. A polypeptide whose polypeptidic sequence comprises or consists of SEQ ID NO: 3, or;
ii. A polypeptide whose polypeptidic sequence comprises or consists in a sequence having at least 23% or at least 30% identity with SEQ ID NO: 3, or;
iii. A polypeptide whose polypeptidic sequence comprises or consists of a fragment, especially a fragment of contiguous amino-acid residues of at least 10 or 17 amino-acid residues, of any one of the sequences defined in i) or ii);

said polypeptide interacting with glycosylated Muc2 protein(s), in particular with sulfated moieties of glycosylated Muc2 protein, of human colonic mucus or human intestinal mucus.

According to specific embodiments of the invention, a polypeptide of the invention has a polypeptidic sequence comprising or consisting of a fragment of the sequence of any one of SEQ ID NO: 5 to SEQ ID NO: 16, or any one of SEQ ID NO: 19 to SEQ ID NO: 22, especially a fragment within the N-terminal extremity of said polypeptide, or has an amino-acid sequence comprising or consisting of any one of SEQ ID NO: 23 to 61 or a variant or a fragment thereof.

In a particular embodiment, the polypeptide of the invention has a length from 38 to 43 amino-acid residues and its polypeptidic sequence also comprises the consensus sequence GY$(X_s)$FND$(X_t)$Q (SEQ ID NO: 67) where X represents any amino-acid, said consensus sequence disclosing, from N-terminal to C-terminal ends, spacer amino-acid segments $(X_c)$ and $(X_t)$ containing respectively s and t numbers of any amino-acid residue(s) which are defined as follows:

s ranges from 12 to 16, in particular is 12, 13, 14 or 15,
t ranges from 5 to 9, in particular is 7 or 6 or 8.

As illustrated in FIG. 32, SEQ ID NO: 67 can differently be written as consensus sequence P8$(X_s)$P9$(X_t)$P10, X being any amino-acid residue, said consensus sequence encompassing, from N-terminal to C-terminal ends, patterns P8, P9, P10, which are defined as follows:

P8 represents the amino-acid motif GY,
P9 represents the amino-acid motif F/YD,
P10 represents the amino-acid residue Q, and wherein said patterns are further characterized by spacer amino-acid segments ($X_s$) and ($X_t$) containing respectively s and t numbers of any amino-acid residue(s) which are defined as follows:

s ranges from 12 to 16, in particular is 12, 13, 14 or 15,
t ranges from 5 to 9, in particular is 7 or 6 or 8.

In a more particular embodiment, P8 and P9 respectively correspond to P3 and P5 of SEQ ID NOS 1 or 2.

In a more specific embodiment, the polypeptide of the invention has a length from 38 to 43 amino-acid residues and its polypeptidic sequence also comprises the consensus sequence GYXL($X_u$)F/YDXD($X_v$)QX(Y/F/W)(TN/E)V (SEQ ID NO: 68) where X represents any amino-acid, said consensus sequence disclosing, from N-terminal to C-terminal ends, spacer amino-acid segments ($X_u$) and ($X_v$) containing respectively u and v numbers of any amino-acid residue(s) which are defined as follows:

u ranges from 10 to 14, in particular is 10, 11, 12 or 13 or 14,
ranges from 2 to 6, in particular is 4 or 2, 3, 5.

As illustrated in FIG. 32, SEQ ID NO: 68 can differently be written as consensus sequence P8'($X_u$)P9'($X_v$)P10', X being any amino-acid residue, said consensus sequence encompassing, from N-terminal to C-terminal ends, patterns P8', P9', P10' encompassing patterns P8, P9 and P10 defined herein, said patterns P8', P9', P10' being defined as follows:

P8' represents the amino-acid sequence GYXL, X being any amino-acid residue,
P9' represents the amino-acid sequence F/YDXD, X being any amino-acid residue,
P10' represents the amino-acid sequence QX(Y/F/W)(TN/E)V, X being any amino-acid residue, and wherein said patterns are further characterized by spacer amino-acid segments ($X_u$) and ($X_v$) containing respectively s and t numbers of any amino-acid residue(s) which are defined as follows:

u ranges from 10 to 14, in particular is 10, 11, 12 or 13 or 14
ranges from 2 to 6, in particular is 4 or 2, 3, 5.

By "variant", it is meant a polypeptide resulting from limited variations in the sequence of the polypeptide of reference, variant polypeptides encompassing polypeptides having at least 23%, 25%, 29%, 40% or 50% identity with the sequence of reference. According to a particular embodiment, identity percentages reach 60%, 70%, 80% or more. In a particular embodiment, identity percentages are at least of 85% or at least of 90%.

According to another particular preferred embodiment, the polypeptidic sequence of a polypeptide of the invention comprises or consists in a sequence having at least 30% identity with SEQ ID NO: 3 (also referred to as $MUB_{70}$ herein), or comprises or consists in SEQ ID NO: 3, or comprises or consists of a fragment, especially a fragment of contiguous amino-acid residues of at least 10 amino-acid residues, in particular at least 17 amino-acid residues, of any one of the sequences or fragment thereof encompassed by the consensus sequences SEQ ID NO: 1 or SEQ ID NO: 2 or fragments thereof, or of any one of the sequences or fragment thereof encompassed by the sequences having at least 30% identity with SEQ ID NO: 3 or fragment thereof.

According to a particular embodiment, a polypeptide of the invention comprises or consists in a sequence having at least 23%, 25%, 29%, 40% or 50% identity with SEQ ID NO: 3 or SEQ ID NO: 58, or a fragment thereof. Identity percentages can reach 60%, 70%, 80% or more. In a particular embodiment, identity percentages are at least of 85% or at least of 90%. Such a polypeptide can be the polypeptide of SEQ ID NO: 67 or the polypeptide of SEQ ID NO: 68.

According to a particular embodiment, a polypeptide of the invention consists of a fragment of contiguous amino-acid residues of about 20, 30 or 40 and up to 50 amino-acid residues of SEQ ID NO: 3, in particular consists of a fragment encompassing the sequence of any one of SEQ ID NOS 58, 59, 60 or 61, or having the sequence of any one of SEQ ID NOS 58, 59, 60 or 61.

According to a particular embodiment, a polypeptide of the invention comprises or consists in a sequence having at least 23%, 25%, 29%, 40%, 50%, 70% or at least 90% identity with any one of SEQ ID NOS 58, 59, 60 or 61, or a fragment thereof. In a particular embodiment, identity percentages are at least of 80 or 85% or at least of 90 or 95%.

According to a particular embodiment, a polypeptide of the invention comprises or consists of any one of SEQ ID NOS 69 to 83, as disclosed in FIG. 32.

With respect to the interaction with glycosylated Muc2 protein(s) of human colonic or intestinal mucus, the expression "interacts" used herein means that a polypeptide of the invention binds said components of the mucus, or enters into close vicinity with such components when present in colonic mucus layers, i.e. loose mucus layer or firm mucus layer, or in intestine mucus.

According to a particular embodiment, a polypeptide of the invention interacts with glycosylated Muc2 protein(s) through sulfated moieties of glycosylated Muc2 protein(s).

According to a specific embodiment, a polypeptide of the invention interacts with glycosylated human, rabbit and guinea pig Muc2 protein(s) but not with murine glycosylated Muc2 protein(s).

According to a particular embodiment, a polypeptide of the invention specifically interacts with mammalian glycosylated Muc2 protein(s), and in particular with glycosylated Muc2 protein(s), from colonic mucus or intestine mucus.

The expression "specifically interacts with Muc2 protein (s)" relates to the fact that the molecule(s) of the invention do(es) not interact or not significantly interact with other secreted gel-forming mucins, taken alone or according to any combination between them, said other secreted gel-forming mucins including for example Muc5ac, Muc5b or Muc6.

According to a particular embodiment, polypeptide(s) of the invention can have a dimeric or a trimeric quaternary structure.

According to a particular preferred embodiment, polypeptide(s) of the invention are able to dimerize or trimerize.

According to a particular embodiment, a polypeptide of the invention has a length from 10, in particular 17, to 100 amino-acid residues, especially from 10 to 80 or 90 amino-acid residues, in particular up to 68, 69, 70, 71 or 72 amino-acid residues. In a particular embodiment a polypeptide of the invention has a length of 15, 17, 20, 30, 40, 50, 60, 65, 68, 69, 70, 71 or 72 amino-acid residues.

According to a particular embodiment, a polypeptide of the invention has a length of 35, 36, 37, 38, 39, 40, 41, 42, 43, 44, 45 amino-acid residues.

In a particular embodiment, a polypeptide of the invention consists or contains or encompasses a sequence found within the N-terminal extremity or the C-terminal extremity of sequence SEQ ID NO: 3, or have at least 23%, 25%, 29%, 40% or 50% identity with a fragment of SEQ ID NO: 3 as found within the N-terminal extremity of said sequence or with SEQ ID NO: 58 or a fragment thereof. Identity percentages can reach 60%, 70%, 80% or more than 85% or 90%. By "N-terminal extremity of sequence SEQ ID NO: 3" it is meant the portion of SEQ ID NO: 3 that is closer to the N-terminal extremity than to the C-terminal extremity. Conversely, by "C-terminal extremity of sequence SEQ ID NO: 3" it is meant the portion of SEQ ID NO: 3 that is closer to the C-terminal extremity than to the N-terminal extremity.

The length of the polypeptide may vary depending on the species, from which it was identified, especially when identified from *Lactobacillus* protein(s).

According to a particular embodiment, the polypeptidic sequence of a polypeptide of the invention is part of the N-terminal sequence of a mucus-binding (MUB) domain, especially a mucus-binding (MUB) domain of a species selected amongst the *Lactobacillus, Streptococcus, Cryptobacterium, Weissella, Granulicatella* or *Leuconostoc* species, and in particular is part of any one of the repeats of a *L. reuteri* mucus-binding (MUB) domain (For example it is part of a polypeptide having a sequence disclosed in Table 2).

By "part of", it is meant that the information relative to the contents in amino-acid residues of the polypeptide(s) of the invention (i.e. the "nature" of said amino-acid residues and their sequence arrangement) can be derived or identified or deduced from the contents of polypeptidic domain(s) or protein(s) or fragment(s) thereof identified as relevant within the present disclosure.

Polypeptides of short length may be preferred and may be obtained by shortening the amino-acid sequence of the identified polypeptides, to the extent that the shorter polypeptides keep the capacity of the original polypeptides to bind human colonic mucus through glycosylated Muc2 protein. Advantageously, a short polypeptide of the invention might be 10, or 17, or 25 to 40 amino-acid long, or 10, or 17, or 25 to 60 amino-acid long.

Examples of short polypeptide(s) of the invention include the polypeptide(s) disclosed herein under SEQ ID NOS 58, 59, 60 or 61, having a length of 40 amino-acid residues. The invention encompasses polypeptides resulting from small variations in the sequence of such polypeptides, including polypeptides having at least 23%, 25%, 29%, 40% or 50% identity with any one of SEQ ID NOS 58, 59, 60 or 61. According to a particular embodiment, identity percentages reach 60%, 70%, 80% or more. In a particular embodiment, identity percentages with respect to any one of SEQ ID NOS 58, 59, 60 or 61 are at least of 85% or at least of 90%.

The invention also encompasses polypeptides resulting from small variations in the size of such polypeptides, including polypeptides having a length of 20, 30, 35, 37, 38, 40, 42, 44, 45 or 50 amino-acid residues.

Accordingly, in a particular embodiment, polypeptides of the invention have from 38 to 43 amino-acid residues and comprise or consist of any one of SEQ ID NOS 69 to 83, as disclosed in FIG. 32, or a fragment thereof.

According to a specific embodiment, the polypeptidic sequence of a polypeptide of the invention can be found within the N-terminal sequence of the repeats of a *L. reuteri* mucus-binding (MUB) domain, i.e, its sequence can be identified or deduced from the N-terminal sequence(s) of the repeats of a *L. reuteri* mucus-binding (MUB) domain, after aligning said N-terminal sequence(s) with the consensus sequences described herein (see Table 1).

TABLE 1

MUB$_{70}$ repeat sequences comparison in *L. reuteri* mucus binding precursor AF120104. Data were obtained using BlastP software, comparing 13 MucBDs (SEQ ID NO: 5 to SEQ ID NO: 16), identified by their amino acids numbers boundaries, within AF120104 protein.

| MUB domain repeat | aa numbers | E value | % identity | % positive |
|---|---|---|---|---|
| 1 | 548-727 | 2e−13 | 35 | 50 |
| 2 | 742-924 | 1e−13 | 35 | 50 |
| 3 | 939-1112 | 1e−13 | 32 | 51 |
| 4 | 1127-1297 | 1e−13 | 35 | 50 |
| 5 | 1317-1500 | 2e−86 | 85 | 91 |
| 6 | 1501-1684 | 3e−101 | 98 | 99 |
| 7 | 1685-1868 | 4e−104 | 100 | 100 |
| 8 | 1869-2052 | 3e−101 | 98 | 99 |
| 9 | 2053-2236 | 4e−104 | 100 | 100 |
| 10 | 2237-2420 | 3e−101 | 98 | 99 |
| 11 | 2421-2604 | 2e−100 | 98 | 98 |
| 12 | 2605-2788 | 3e−93 | 92 | 95 |
| 13 | 2974-3165 | 1e−08 | 29 | 47 |

The "repeats" of *L. reuteri* mucus-binding (MUB) domain are illustrated in Table 1 and the figures and the examples, as a domain encompassing around 200 amino-acid residues. Although different for each repeat, the amino-acid sequences of these repeats show common functional features related to mucus binding. The consensus sequences described herein share patterns that are considered important for said common binding functional features.

The annotated GenBank entry of the mub gene from *L. reuteri*, encoding the Mub protein from *L. reuteri* containing such a mucus-binding (MUB) domain can be found under accession number AF120104.1 (SEQ ID NOS 17 and 18).

By comparison of the Mucus Binding proteins of other organisms, especially *Lactobacillus*, it has been possible to determine similarly functional domains with respect to Muc2 protein binding in colonic mucus, thereby providing the definition of further polypeptides. Accordingly, the invention relates to a polypeptide having a length from 10, in particular at least 17, to 80 amino acid residues and whose sequence can be identified in the N-terminal sequence of the repeats of a Mucus Binding Domain (MUcBD) present in mucus binding protein (MucBP) of *L. gasseri, L. johnsonii, L. fermentum* or *L. Acidophilus* (see FIG. 10 and Table 2), or of *Streptococcus, Weissella,* or *Leuconostoc* species (see Table 2).

According to a specific embodiment, a polypeptide of the invention comprises or consists of a fragment of the polypeptide having the sequence of any one of SEQ ID NO: 5 to SEQ ID NO: 16, or any one of SEQ ID NO: 19 to SEQ ID NO: 22, especially a fragment within the N-terminal extremity of said polypeptide, or this polypeptide has an amino-acid sequence comprising or consisting of any one of SEQ ID NOS 23 to 57 or a fragment thereof.

TABLE 2

MUB$_{70}$ (SEQ ID NO: 3) sequence comparison in several species.
MUB70 (SEQ ID NO: 3)
VHVQYIDGETDQMLRQDDLDGYTDETIPYSTAEGIKKFEGDGYELFKDNFPAGEKFDNDDTNDQFYTVIF

| SEQ ID NO: | GENE ID | Sbjct | % Identity | Sequence |
|---|---|---|---|---|
| 23. | 3252355 LBA1020\| mucus binding protein [Lactobacillus acidophilus NCFM] | | 49% (34/70) | VNYVDADEDNKLITSSGDLTGKAGETINYSTADTIKD LENKGYVLVNDGFPAGAKYDSDDNTTQIYTVVL |
| 24. | ref\|ZP 04061590.1\| MucBP domain protein [Streptococcus salivarius SK126] Length = 245 | Sbjct 57 | 44% (31/70) | ITYVDQTTGQTLANDQVGGKSGEAINYSTADKIKYY EDRGYVLVSDEFPTGAHFDNDASVDQTVVTVTL |
| 25. | ref\|NP 964063.1\| hypothetical protein LJ0047 [Lactobacillus johnsonii NCC 533] | Sbjct 1542 | 46% (32/70) | VNYIDADDNNAIITSSDNLTGKAGEKIDYSTASTIEEL ENKGYVLVSDGFPAGATFDNDDNTTQIYTVVL |
| 26. | ref\|ZP 04063040.1\| adhesion exoprotein [Streptococcus salivarius SK126] | Sbjct 1429 | 44% (31/70) | ITYVDQTTGQTLANDQVGGKSGEAINYSTADKIKYY EDRGYVLVSDEFPKGAHFDNDASVDQIVVTVTL |
| 27. | ref\|ZP 04061224.1\| adhesion exoprotein [Streptococcus salivarius SK126] | Sbjct 223 | 44% (31/70) | ITYVDQTTSQTLANDQVGGKSGEAINYSTADKIKYYE DRGYVLVSDEFPTGAHFDNDASVDQTVVTVTL |
| 28. | ref\|ZP 03073062.1\| LPXTG-motif cell wall anchor domain protein [Lactobacillus reuteri 100-23] ("LPXTG" disclosed as SEQ ID NO: 84) | Sbjct 1198 | 44% (31/70) | VNYVDQDNNNAQIATSGNLTGKPGSVINYSTADQIK QLEAQGYVLVSDGFPAGAVFDNDDNTTQTYTVVL |
| 29. | ref\|ZP 08229673.1\| mucus binding protein [Leuconostoc argentinum KCTC 3773] | Sbjct 16 | 40% (28/70) | VSYVDDTTGKTLKTDSISGTTGSKSSYSTSGNIADYK KHGYELVTDGYPADLTFDNDDKTDQNFTV |
| 30. | ref\|ZP 08574918.1\| cell surface protein precursor [Lactobacillus coryniformis subsp. torquens KCTC 3535] | Sbjct 732 | 41% (29/70) | VSYVDDTTGKTLKTDSISGTTGSKSSYSTSGNIADYK KQGYELVTDGYPADLTFDNDDTTDQNFTV |
| 31. | ref\|ZP 03073481.1\| LPXTG-motif cell wall anchor domain protein [Lactobacillus reuteri 100-23] | Sbjct 3821 | 44% (31/70) | VNYVDQDNNNAQIATSGNLTGKPGSVINYSTADQIK QLEDQGYVLVSDGFPAGAVFDNDDNTTQTYTVVL |
| 32. | ref\|YP 004727441.1\| hypothetical protein SALIVB_0614 [Streptococcus salivarius CCHSS3] | Sbjct 601 | 44% (31/70) | ASVTYRDETSGSILETVALAGKSGEAINYSTAERIKH YQDLGYALVTDGYPAGASFDLDSTVDQAWTVSF |
| 33. | ref\|YP 001727229.1\| mucus binding protein [Leuconostoc citreum KM20] | Sbjct 688 | 40% (28/70) | VSYVDDTTGKTLKTDSISGTTGSKSSYSTSGNIADYK KQGYELVTDGYPADLTFDNNDTTDQNFTV |
| 34. | ref\|ZP 04642914.1\| adhesion exoprotein [Lactobacillus gasseri 202-4] | Sbjct 2768 | 43% (30/70) | DGANKQLATSGDLTGKSGSEISYSTADQIKKLINQG YVLKNDGFPAGAVFDNDDSKNQVFYVDF |

TABLE 2 -continued

MUB₇₀ (SEQ ID NO: 3) sequence comparison in several species.
MUB70 (SEQ ID NO: 3)
VHVQYIDGETDQMLRQDDLDGYTDETIPYSTAEGIKKFEGDGYELFKDNFPAGEKFDNDDTNDQFYTVIF

| SEQ ID NO: | GENE ID | Sbjct | % Identity | Sequence |
|---|---|---|---|---|
| 35. | ref\|ZP 06261711.1\| gram-positive signal peptide protein, YSIRK family [*Lactobacillus gasseri* 224-1] | Sbjct 2818 | 43% (30/70) | DGANKQLATSGDLTGKSGSEISYSTADQIKKLINQG YVLKNDGFPAGAVFDNDDSKNQVFYVDF |
| 36. | ref\|YP 813898.1\| adhesion exoprotein +*Lactobacillus gasseri* ATCC 33323] | Sbjct 2830 | 43% (30/70) | DGANKQLATSGDLTGKSGSEISYSTADQIKKLINQG YVLKNDGFPAGAVFDNDDSKNQVFYVDF |
| 37. | ref\|ZP 07712941.1\| putative mucus binding protein [*Lactobacillus gasseri* MV-22] Length = 2986 | Sbjct 2124 | 43% (30/70) | DGANKQLATSGDLTGKSGSEISYSTADQIKKLINQG YVLKNDGFPAGAVFDNDDSKNQVFYVDF |
| 38. | ref\|YP 004033545.1\| mucus binding protein [*Lactobacillus delbrueckii* subsp. *bulgaricus* ND02] | Sbjct 612 | 43% (30/70) | AKVAYIDDKTGKTLKTDSLTGVTNAKSGYTTADSIKT YQALGYKLVSDDTKGAEIVFDNEDGKDQSYTVHF |
| 39. | ref\|ZP 05549219.1\| adhension protein [*Lactobacillus crispatus* 125-2-CHN] | Sbjct 2301 | 43% (30/70) | VNYIDSDEGNKVITTSGNLSGKAGSTIDYSTKSTIADL ENKGYVLVNDGFPAGAKFDSDDNTTQIFTVVL |
| 40. | ref\|ZP 08047859.1\| putative mucus binding protein [*Streptococcus* sp. C150] | Sbjct 334 | 43% (30/70) | ASVTYRDETGGSTLETVSLAGKSGEAVGYSTAERIK HYQDLGYVLVTDGYPAGTTFDLDSTVDQAWTVSF |
| 41. | ref\|ZP 04061106.1\| MucBP domain protein [*Streptococcus salivarius* SK126] | Sbjct 760 | 41% (29/70) | ASVTYRDETSGSTLETVALAGKSGEAVNYSTADRIK HYQDLGYVLVTDGYPAGATFDLDSTVDQAVVTVSF |
| 42. | ref\|ZP 07644834.1\| Mlp [*Streptococcus mitis* NCTC 12261] | Sbjct 429 | 37% (26/70) | IRYVSTNGNQVLKTDEVTGKSGEAIAYSTTSQINEFK KQGYKLVSDEFTAGGAKVYDYDTARDQVYTVTL |
| 43. | ref\|ZP 08417090.1\| mucus binding protein [*Weissella cibaria* KACC 11862] | Sbjct 4532 | 39% (27/70) | IAYIDKTTGKQLALDPITGHSDESSTYTTADKIAAYEA AGYVLVSDGYPGANFTFDREDDYDQTYEVIL |
| 44. | ref\|YP 004727470.1\| hypothetical protein SALIVB_0643 [*Streptococcus salivarius* CCHSS3] | Sbjct 231 | 41% (29/70) | ITYIDETTGAYLVSDQLTGELGEAIEYGTATRIKTFKD MGYELIQDEFPKDAIFDDKDIDDQEWFVLL |
| 45. | ref\|ZP 04008293.1\| conserved hypothetical protein [*Lactobacillus johnsonii* ATCC 33200] | Sbjct 86 | 40% (28/70) | VTYVDDKTGKTLKVDNLNGVTSAKSGYTTKAAIDTY TGLGYTLVSDDTNGNEWFDNDDSNDQAFTV |
| 46. | ref\|YP 193899.1\| mucus binding protein [*Lactobacillus acidophilus* NCFM] Length = 2650 | Sbjct 2251 | 39% (27/70) | VNYIDADEGNKVIISSGNLIGKAGDKVDYNTSDTIKNL ENKGYVLVHNGFPDGVTFDNDDSTIQTYTVIL |
| 47. | ref\|ZP 04021706.1\| mucus binding protein [*Lactobacillus acidophilus* ATCC 4796] | Sbjct 2251 | 39% (27/70) | VNYIDADEGNKVIISSGNLIGKAGDKVDYNTSDTIKNL ENKGYVLVHNGFPDGVTFDNDDSTIQTYTVIL |

TABLE 2 -continued

MUB₇₀ (SEQ ID NO: 3) sequence comparison in several species.
MUB70 (SEQ ID NO: 3)
VHVQYIDGETDQMLRQDDLDGYTDETIPYSTAEGIKKFEGDGYELFKDNFPAGEKFDNDDTNDQFYTVIF

| SEQ ID NO: | GENE ID | Sbjct | % Identity | Sequence |
|---|---|---|---|---|
| 48. | ref\|ZP_04061119.1\| MucBP domain protein [*Streptococcus salivarius* SK126] | Sbjct 231 | 40% (28/70) | ITYIDETTGAYLVSDQLTGELGEAIEYGTATRIKTFKD MGYDLIQDEFPKDAIFDDKDIDDQEWFVLL |
| 49. | ref\|YP_004034456.1\| cell surface protein [*Lactobacillus delbrueckii* subsp. *bulgaricus* ND02] | Sbjct 452 | 41% (29/70) | VSYVDDTTGKTLKTDSISGITGSKSSYSTSGSIADYK KQGYELVTDGYPADLTFDNDDTTDQNFTV |
| 50. | ref\|ZP_05863780.1\| conserved hypothetical protein [*Lactobacillus fermentum* 28-3-CHN] | Sbjct 410 | 41% (29/70) | VSYVDDTTGKTLKTDSISGTTGSKSSYSTSGSIADYK KQGYELVTDGYPADLTFDNDDTTDQNFTV |
| 51. | ref\|YP_001843489.1\| hypothetical protein LAF_0673 [*Lactobacillus fermentum* IFO 3956] | Sbjct 533 | 41% (29/70) | VSYVDDTTGKTLKTDSISGTTGSKSSYSTSGSIADYK KQGYELVTDGYPADLTFDNDDTKDQNFTV |
| 52. | ref\|ZP_08047833.1\| putative mucus binding protein [*Streptococcus* sp. C150] | Sbjct 1019 | 41% (29/70) | VTYVDGTTRKKLEVVDLLGKSGEVIDYSTIERIKYYS DRGYTLLADGFTNGVIFDGDSHVDQNFMVTL |
| 53. | ref\|ZP_05863779.1\| predicted protein [*Lactobacillus fermentum* 28-3-CHN] | Sbjct 30 | 41% (29/70) | VSYVDDTTRKTLKTDSISGTTGSKSSYSTSGSIADYK KQGYELVTDGYPADLMFDNDDTTDQNFTV |
| 54. | ref\|ZP_07059088.1\| conserved hypothetical protein [*Lactobacillus gasseri* JV-V03] | Sbjct 1860 | 44% (31/70) | IIYVDETTGKALETATVDGKYNESINYSTADKIKYYES LGYELVKDGYTAG-KF--GETTKTFY-VIF |
| 55. | ref\|ZP_04644067.1\| putative cell surface protein [*Lactobacillus gasseri* 202-4] | Sbjct 1440 | 34% (24/70) | IVYVDETTGKELERATVDGKYNETINYSTADKIKYYE SLGYELVKDGYTGGE |
| 56. | ref\|ZP_07712160.1\| putative mucus binding protein [*Lactobacillus gasseri* MV-22] | Sbjct 485 | 32% (22/70) | LDNEGQQITSSGPLIGKPNENITDLYSTSIPLAGLEKA GYHVIFNNFDGNNKIQKFDGNDLTTQVFTV |
| 57. | ref\|ZP_04643870.1\| adhesion exoprotein [*Lactobacillus gasseri* 202-4] | Sbjct 488 | 32% (22/70) | LDNEGQQITSSGPLIGKPNENITDLYSTSIPLAGLEKA GYHVIFNNFDGNNKIQKFDGNDLTTQVFTV |

Compared sequences are identified with their Genbank access numbers (SEQ ID NO: 23 to SEQ ID NO: 57), alignments identity results with SEQ ID NO: 3 are provided.

In a particular embodiment, a polypeptide of the invention has the sequence SEQ ID NO: 3 or SEQ ID NO: 4 or has an amino-acid sequence comprising or consisting of any one of SEQ ID NO: 23 to 57 or a fragment thereof.

In a specific embodiment, a polypeptide of the invention is a fragment of contiguous amino-acid residues of at least 10 amino-acid residues, in particular 17 amino-acid residues, of SEQ ID NO: 3 or SEQ ID NO: 4 or of any one of SEQ ID NOS 5 to 16 or SEQ ID NOS 19 to 57.

The inventors have also synthesized and characterized shorter peptides according to the invention, identified by the term MUB₄₀, which span the entire MUB₇₀ sequence. Their sequences are provided in Table 3.

TABLE 3

MUB₄₀ (SEQ ID NOS 58, 59, 60 and 61) operating sequences. See also FIG. 17

| SEQ ID NO: | References | Sequence |
|---|---|---|
| 58 | MUB40-1, used for probe MUB40-Cy5#1 | TAEGIKKFEGDGYELFKDNFPAGEK FDNDDTNDQFYTVIF |
| 59 | MUB40-2, used for probe MUB40-Cy5#2 | GYTDETIPYSTAEGIKKFEGDGYEL FKDNFPAGEKFDNDD |

TABLE 3 -continued

MUB₄₀ (SEQ ID NOS 58, 59, 60 and 61) operating sequences. See also FIG. 17

| SEQ ID NO: | References | Sequence |
|---|---|---|
| 60 | MUB40-3, used for probe MUB40-Cy5#3 | DQMLRQDDLDGYTDETIPYSTAEGI KKFEGDGYELFKDNF |
| 61 | MUB40-4, used for probe MUB40-Cy5#4 | VHVQYIDGETDQMLRQDDLDGYTDE TIPYSTAEGIKKFEG |

In a particular embodiment, a polypeptide of the invention has the sequence SEQ ID NOS 58 or 59 or 60 or 61 or has an amino-acid sequence comprising or consisting of any one of SEQ ID NOS 58 to 61 or a fragment thereof.

According to a particular embodiment, synthesized peptides $MUB_{40-1}$ to $MUB_{40-4}$ of the invention (SEQ ID NOS 58, 59, 60, 61) have an additional Cysteine residue at their respective N-terminal extremities (SEQ ID NOS 62, 63, 64, 65). These shorter peptides proved to be functional as human mucus-binding peptides, as detailed herein.

A polypeptide of the invention advantageously lacks or is devoid of hydrophobic domain(s). According to a preferred embodiment, it does not penetrate into living cells, especially eukaryotic cells and in particular it does not penetrate into such cells of human colon, e.g. goblet cells. According to a particular embodiment however, a polypeptide of the invention possesses globet-cells binding properties.

However in a particular embodiment, polypeptide(s) of the invention penetrate into fixed cell(s).

According to a particular embodiment, polypeptide(s) of the invention is/are not toxic to cells. Non-limitative examples of cells that might be impervious to the polypeptides of the invention are epithelial cells, especially human epithelial cells, myeloid cells, especially human myeloid cells, Embryonic Stem (ES) cells, especially human Embryonic Stem (ES) cells, dendritic cells, especially mouse dendritic cells.

However, it was found that, according to a particular embodiment, the polypeptides of the invention target components found at the level of neutrophile granules, especially fixed neutrophile granules, which are not yet characterized. In vitro incubation of the polypeptide with living neutrophiles, or analysis of fixed neutrophiles, therefore allows the detection of degranulation events.

In a particular embodiment, a polypeptide of the invention has an additional Cysteine residue at its N-terminal extremity. The presence of a free Cysteine residue may be of interest to enable attachment of additional moieties, especially markers or labels or other active groups.

However, according to another particular embodiment, no specific amino-acid residue is required at the N-terminal extremity of a polypeptide of the invention to achieve attachment of additional moieties, since any amino-acid carboxy group or another chemical group of a polypeptide of the invention can be used to this end.

In a particular embodiment of the invention, the polypeptide comprises or is constituted by L amino acid residues.

In a particular embodiment, the polypeptides comprise or are fully constituted by D-amino acids (excluding the chiral form of amino acids naturally synthesized by living organisms, which is the L-form), or comprise or are fully constituted by modified aminoacids. Such modifications might help preventing proteolytic cleavage by active enzymes, especially when the polypeptide is administered in vivo.

According to a particular embodiment, polypeptide(s) of the invention is/are labelled, especially by coupling with a fluorophore such as Cy5, Cy5.5, or a biotin. A Cy5-labelled $MUB_{70}$ polypeptide (or respectively, a Cy5-labelled $MUB_{40}$ polypeptide) is therefore referred to as $MUB_{70}$-Cy5 or Cy5-$MUB_{70}$ (respectively $MUB_{40}$-Cy5 or Cy5-$MUB_{40}$) within the present disclosure.

According to a particular embodiment, the invention enables the detection or the monitoring of mucus production and/or mucus composition in human or animal body(ies), especially the detection or the monitoring of human colonic or intestinal mucus. According to a particular embodiment, the invention makes use of labeled polypeptide(s) as probe (s), especially as physiological labeled probe(s) for staining Muc2 protein(s) contained in mucus layer(s) of cell or tissue sample(s).

According to a particular embodiment, the invention makes use of labeled polypeptide(s) as probe(s), especially labeled probe(s) for staining fixed or living neutrophile(s). Staining living neutrophile(s) is preferably achieved in vitro.

It has further been observed by the inventors that Muc2 proteins are also expressed in other tissues of the human body, either when said tissues are in a healthy state or to the contrary when they reflect a pathological state.

Hence, the polypeptides of the invention may be used for detection or monitoring of mucus production and/or composition, in other tissues such as lung tissue or epithelial tissue.

In a particular embodiment, polypeptide(s) of the invention is/are associated in a molecule with a reporter or a carrier molecule or with an active molecule such as drug(s) (i.e. anti-inflammatory molecule(s)) or enzyme(s) such as DNase or chitinase (e.g. cystic fibrosis context), or fragments thereof.

The polypeptides and molecules of the invention can be prepared by conventional routes, in particular chemically synthesized or engineered through biotechnological methods.

In a particular embodiment wherein the polypeptide of the invention has the sequence SEQ ID NO: 3 or SEQ ID NO: 4 or a continuous fragment thereof, in particular a fragment thereof of about contiguous 40 amino-acid residues, especially as found within the C-terminal extremity of SEQ ID NO: 3 or SEQ ID NO: 4, chemical synthesis is achieved through Solid-Phase synthesis, especially trough Fmoc-SPPS, including steps of coupling with Fmoc-Asp(OtBu)-(Dmb)Gly-OH dipeptides when the synthesis reaches the positions 29 and/or 50 and/or 63 in reference to the C-terminus of SEQ ID NO: 3.

Additionally, said solid-phase synthesis can include steps of incorporation of pseudoproline dipeptides when the synthesis reaches positions 10 and/or 40 in reference to the C-terminus of SEQ ID NO: 3.

This synthesis is illustrated in the examples and can be similarly used for other polypeptides having analogous amino-acid composition, in particular peptides shorter than the MUB70 peptide and having at least partly an amino-acid composition that is analogous to MUB70 peptide composition.

Accordingly, the specific features and properties detailed herein with respect to the MUB70 peptide are also applicable to MUB70 analogous peptide(s), (having similarity in amino-acid composition, or encompassing MUB70 fragment(s), or MUB70 fragment(s)), as disclosed herein.

When polypeptide(s) of the invention are prepared in recombinant cells, these cells are recombined with a polynucleotide expressing the polypeptide, using nucleic acid expression systems such as plasmid vectors.

Therefore, the invention also encompasses nucleic acid molecule(s) encoding polypeptidic sequence(s) of isolated polypeptide(s) as described herein and nucleic acid expression system(s), especially vector(s) comprising such nucleic acid molecule(s) under expression control sequences.

According to a particular embodiment, production of isolated polypeptide(s) of the invention is achieved through the transfection of such vector(s) in cell(s) such as E. coli cell(s) or eukaryotic cells, including yeast cells, insect cells or mammalian cells, the culture of said cell(s) and the recovery of the protein result of the culture, especially the recovery of the polypeptide(s) of the invention.

According to a particular embodiment, production of isolated polypeptide(s) of the invention is done using a MGMT-based method for obtaining high yield of recombinant protein expression, as disclosed in patent application WO2012/076715.

In such a particular embodiment, a vector of the invention may comprise a nucleotide sequence encoding in a single open reading frame, from 5' to 3':
   a) a peptidic secretion signal which is functional in insect cells, in particular S2 Drosophilia insect cells;
   b) a 6-methylguanine-DNA-methyltransferase enzyme (MGMT, EC 2.1.1.63) or a mutant or a fragment thereof having at least 80% of the catalytic activity of the native MGMT protein;
   c) a polypeptide of the invention, as disclosed herein.

In a particular embodiment, production of isolated polypeptide(s) of the invention is thus achieved through the transfection of the vector(s) described herein, in particular MGMT-based vector(s), in S2 Drosophilia insect cell(s).

The invention also encompasses cell(s) or population of cells, in particular S2 Drosophilia insect cells, comprising a nucleic acid molecule or a vector as described herein, especially for use in a method of production of isolated or purified polypeptide(s) of the invention.

The invention also relates to composition(s) comprising polypeptide(s) of the invention, in particular pharmaceutical composition(s) when the polypeptide is associated with an active ingredient having a therapeutic effect, said composition comprising if necessary pharmaceutically acceptable excipient(s), such as carrier(s) and/or adjuvant(s), According to a particular embodiment, the molecule(s) derived from theses polypeptides according to the invention might be used in a method for manufacturing a medicament, when a step of association of a polypeptide of the invention with a biologically active molecule is performed, and therefore used in a method of therapy practised on human or animal body(ies), in particular for treating a disease selected form the following group, or its symptom(s): neoplasic disease(s), including mucinous carcinoma(s), gastric cancer(s) or colorectal cancer(s), especially colon cancer(s), cystic fibrosis disease, intestine inflammatory disease(s) such as inflammatory bowel disease (IBD) and ulcerative colitis.

The invention thus also relates to the use of a polypeptide of the invention, as a probe or marker for staining living cell(s) or tissue(s) in in vivo, ex vivo, specifically in in vitro experiments, in particular in live microscopy experiments. Live microscopy encompasses for example the use of widefield microscopy on living cells (for example HT29-MTX cells stained with Cy5-$MUB_{70}$), 2-photons microscopy (for example on human colon ex vivo sample stained with Cy5-$MUB_{70}$), or 3D animal analysis (Xenogen, Ivis, Cy5-$MUB_{70}$), (Fluoptics, Cy5.5-$MUB_{70}$), or spectral imaging (for example: coloscopy).

In a particular embodiment, the invention relates to the use of a labelled polypeptide as a probe or marker for staining Muc2 protein(s) contained in mucus layer of a cell or tissue sample, especially human colonic or intestine tissue sample.

In a particular embodiment, the invention relates to the use of a polypeptide as a physiological labelled probe to detect in vitro interaction with human colonic mucus in the adhesive mucus layer of colonic tissue sample and/or to detect in vitro interaction with globet cells.

By "physiological labelled probe", it is meant a probe that is non-harmful, i.e. non-toxic, and well-tolerated by cells or biological tissues.

In a particular embodiment, the invention relates to the use of a polypeptide to detect in vitro mucus production or mucus composition in human colon, said use comprising contacting said polypeptide with a sample of colonic tissue comprising adhesive mucus layer and goblet cells and detecting stained mucus.

In another particular embodiment, the invention relates to a polypeptide of the invention, which is labelled, for use as a probe for in vivo detection of mucus production or mucus composition in human intestine, especially colon or other compartments such as lung tissue, nasal tissue or stomach tissue.

The invention therefore relates to the use of a polypeptide or of a composition comprising the same, as a probe for staining mucus potentially containing Muc2 protein(s) or exhibiting variations in Muc2 protein(s) expression that could provide information on a change in mucus production or in mucus composition.

According to a particular embodiment, the observed mucus is colonic mucus, for example in human, rabbit or guinea pig samples as well as human cell lines producing a mucus layer samples.

According to a particular embodiment, the observed mucus is human colonic carcinoma mucus.

According to a particular embodiment, stained mucus-producing cells are eukaryotic cell(s), including intestine mucus cells, such as goblet cells.

The probes of the invention are preferably non-toxic to cells, which are preferably impervious to said probes.

However, according to another specific embodiment, the invention is also directed to the use of a polypeptide of the invention, in particular $MUB_{70}$ and/or $MUB_{40}$ polypeptides or polypeptides sharing identity with $MUB_{70}$ and/or $MUB_{40}$ polypeptides, or fragments thereof, as marker of degranulation event(s) in neutrophiles, especially an in vitro marker of degranulation event(s) in neutrophiles Detection in vitro of mucus production or mucus composition in human colon might serve as a basis for comparisons between samples, and therefore might serve to analyse or detect or monitor variations or modulations of mucus production or mucus composition in an human or animal body. With this respect, it has been observed that Muc2 protein is naturally expressed and secreted in intestine mucus as a major component of said mucus in healthy tissue, especially in healthy colonic tissue. It has also been observed that Muc2 protein is not expressed in healthy trachea or lung tissues, and in healthy stomach tissues. A change in Muc2 expression in these tissues may thus provide information on the tissue status.

Muc2 expression modulation is also observed in gastric cancer (increased), in ductal adenocarcinoma, in cystic fibrosis (increased), in cystic fibrosis transmembrane conductance regulator model, especially with respect to lung tissues, nasal tissue, goldbladder tissue, pancreas tissue. Muc2 expression modulation is also observed in Inflammatory Bowel Diseases (IBD) such as ulcerative colitis and Crohn disease.

Also, Muc2 glycosylation profile is modulated in colonic diseases such as ulcerative colitis or colorectal carcinoma.

Accordingly, another object of the invention is therefore the use of a polypeptide or of a composition of the invention for in vitro detecting or monitoring any one of the following disease conditions: neoplasic disease(s), including mucinous carcinoma(s), in particular colonic mucinous carcinoma(s), gastric cancer(s) or colorectal cancer(s), especially colon cancer(s), (but also lung, stomach, breast, prostate, or bile ducts cancers) cystic fibrosis, intestine inflammatory disease(s) such as inflammatory bowel disease (IBD) and ulcerative colitis.

The invention also relates to a method for manufacturing a medicament comprising a step of association, especially, coupling, grafting or fusing a polypeptide of the invention with a biologically active molecule such as a drug or an enzyme.

Polypeptide(s), composition(s) or medicament(s) resulting from a polypeptide associated with a biologically active molecule can be used in a method of therapy practised on a human or animal body.

The invention thus encompasses the use of polypeptide(s), composition(s) or medicament(s) resulting from a polypeptide associated with a biologically active molecule for use in treating a disease selected from the following group, or its symptom(s): neoplasic disease(s), including mucinous carcinoma(s), in particular colonic mucinous carcinoma(s), gastric cancer(s) or colorectal cancer(s), especially colon cancer(s) but also lung, stomach, breast, prostate, or bile ducts cancers, cystic fibrosis, intestine inflammatory disease(s) such as inflammatory bowel disease (IBD) and ulcerative colitis.

Other examples and features of the invention will be apparent when reading the examples and the figures, which illustrate the experiments conducted by the inventors, in complement to the features and definitions given in the present description.

LEGEND OF THE FIGURES

Figure 1B:
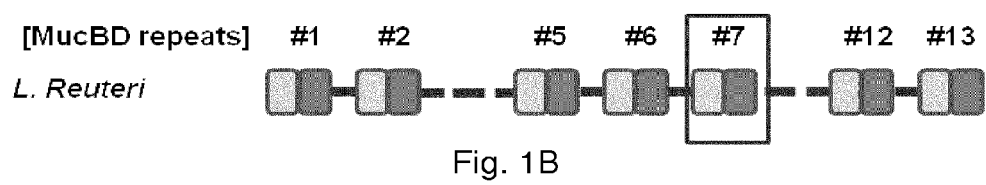

FIGS. 1A-1C. $MUB_{70}$ identification in *L. reuteri*. (FIG. 1A) MucBP diversity illustrated comparing *L. reuteri* (Genbank AF120104) and *L. plantarum* (Ip_1229). (FIG. 1B) Representation of $MUB_{70}$/MucBD 13 repeats of *L. reuteri* AF120104 (SEQ ID NO: 5 to SEQ ID NO: 16). (FIG. 1C) Sequences comparison between *L. reuteri* AF120104 (SEQ ID NO: 11) protein sequence and homologous proteins in *L. gasseri* (ZP_07711585) (SEQ ID NO: 19), *L. johnsonii* (ZP_04008294.1) (SEQ ID NO: 20), *L. fermentum* (YP_001843489.1) (SEQ ID NO: 21) and *L. acidophilus* (SEQ ID NO: 22) are performed using ClustalW software. $MUB_{70}$ sequence and conserved amino acid are highlighted in light gray. MucBD (pfam 06458) sequence and conserved amino acids are highlighted in dark gray. Perfect match over all compared sequences are identified with an asterisk. Good matches are identified with a double dot or a dot.

Figure 2A:
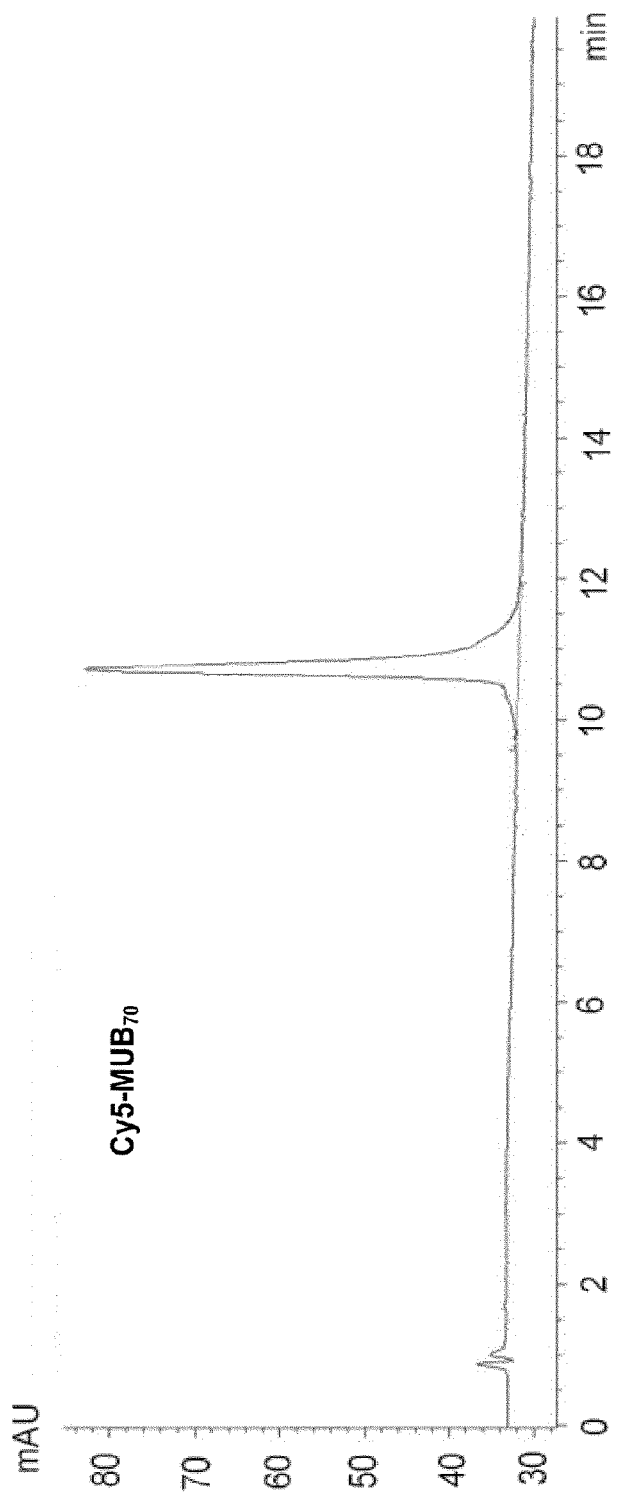
Figure 2B:
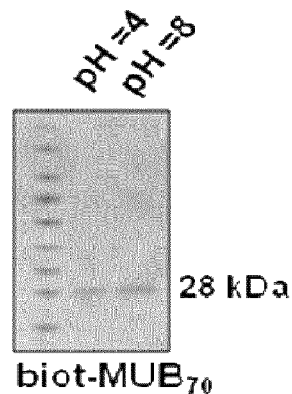
Figure 2C:
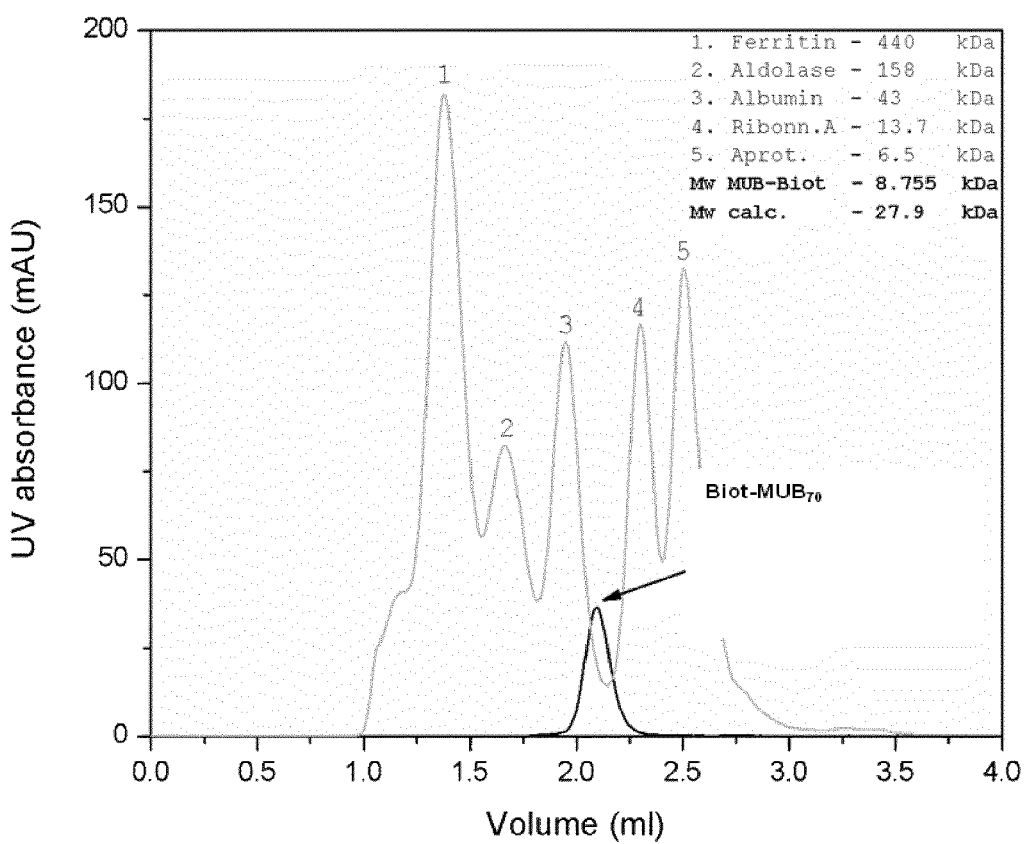

FIGS. 2A-2C. $MUB_{70}$ chemical synthesis and biochemical analysis of trimerization property. (FIG. 2A) RP-MPLC $MUB_{70}$ final purification result. (FIG. 2B). SDS-PAGE visualization of the trimeric form of biot-$MUB_{70}$ performed after incubation of the peptide in Tris 25 mM pH=4 and pH=8. (FIG. 2C) Characterization of biot-$MUB_{70}$ by gel filtration chromatography on Superdex 200 5/150 GL column. The elution profile of biot-$MUB_{70}$ is shown at 280 nm.

Figure 3A:
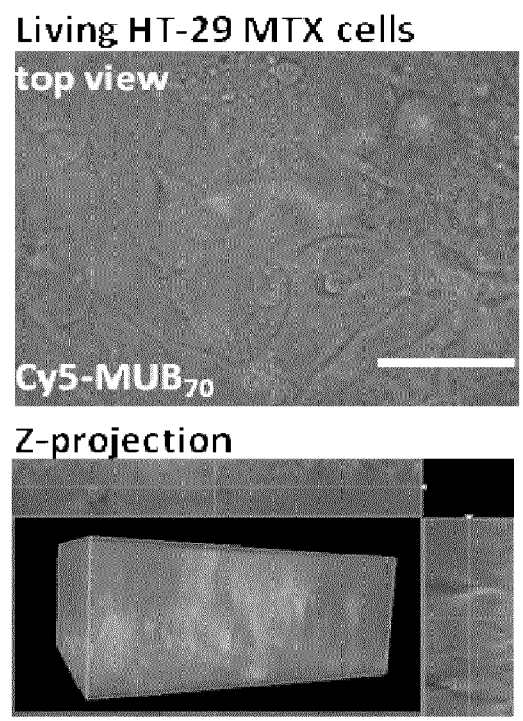
Figure 3B:
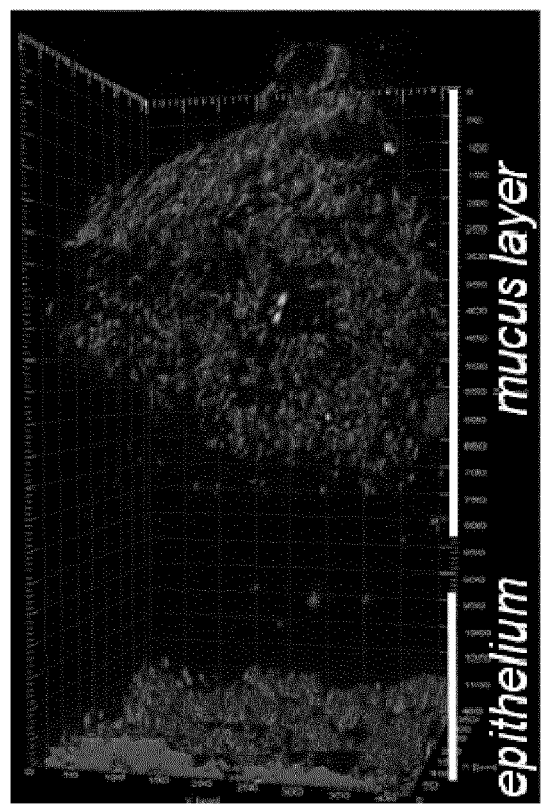

FIGS. 3A-3B. Cy5-$MUB_{70}$ colonic mucus binding property. (FIG. 3A) HT-29 MTX living cells were incubated for 2 h with Cy5-$MUB_{70}$ in a serum-free media. The resulting fluorescent signal (red) was visualized at the surface of the cell layer using an epifluorescent microscope. Z-projection, performed using ImageJ software, allowed 3D localization of Cy5-$MUB_{70}$ fluorescence signal in the mucus layer. Bar is 10 μm (FIG. 3B) MPE and SHG imaging of the binding of Cy5-$MUB_{70}$ to the human colonic mucus. 3D reconstruction (isosurface representation) shows the colonic epithelium covered by the mucus layer (up to 1 000 μm) after 90 min of incubation with Cy5-$MUB_{70}$. Human tissue autofluorescence is detected in the same red channel as Cy5.

Figure 4A:
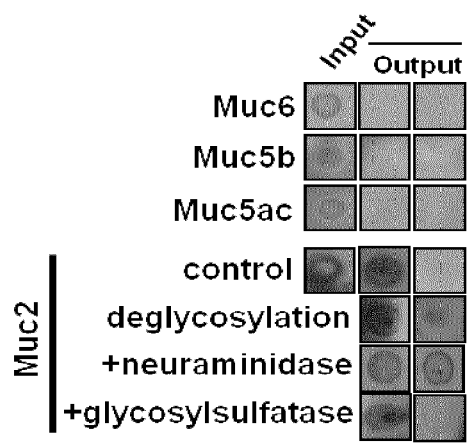
Figure 4B:
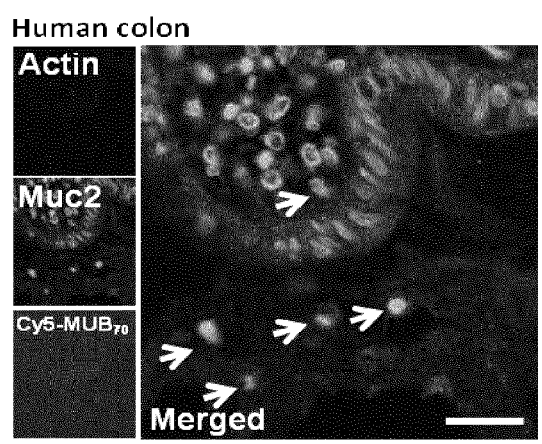

FIGS. 4A-4B. Cy5-$MUB_{70}$ is specifically binding to the glycosylated moiety of Muc2 secreted in the colon mucus layer. (FIG. 4A) Immunodetection of Muc2, Muc5ac, Muc5b and Muc6 (dotblot analysis) on human mucus extracts eluted after a pulldown assay performed with biot-$MUB_{70}$ on avidin conjugated beads (see Methods). Biotin is used as a negative control. Immunodetection of Muc2 (dot-blot analysis) on deglycosylated mucus extracts eluted after a pulldown assay performed with biot-$MUB_{70}$ on avidin conjugated beads. Non-deglycosylated mucus extract is used as a positive control. (FIG. 4B) Co-localization of Muc2 (green) and Cy5-MUB (blue) observed on fixed (Carnoy) human colon samples. Actin is stained in red (Phall.RRX). Observations are performed using a confocal microscope. Bars is 20 μm.

FIG. 5. $MUB_{70}$ (SEQ ID NOS 3 or 4) synthesis strategies description. Operating sequences for designed synthesis 1 and 2, where secondary amino acid surrogates are underlined (pseudoproline dipeptides) or bold (Dmb dipeptides). Proline residues are in italic.

FIGS. 6A-6E. $MUB_{70}$ analytical HPLC profiles in TFA conditions. (FIG. 6A) Crude synthesis 1. $MUB_{70}$ was detected as a major peak (around 8% by area integration) (FIG. 6B) Crude synthesis 2. Optimisation of the synthesis adding three Dmb dipeptides able to reduce aspartimide side reaction and two pseudoproline dipeptides (see Methods). $MUB_{70}$ was detected as a major peak representing 25% of the area integration. (FIG. 6C) Monomeric $MUB_{70}$ after a first step of purification (in acidic conditions, pH 6.5). (FIG. 6D) $MUB_{70}$ after a second step of purification (neutral conditions) and (FIG. 6E) $MUB_{70}$ after a third step of purification (neutral conditions) allowed to yield a purity above 90% on $MUB_{70}$ oligomers.

FIGS. 7A-7D. Biochemical properties of $MUB_{70}$. (FIG. 7A) $MUB_{70}$ total charge was calculated using Protein Calculator program (Scripps website). (FIG. 7B) Kytes and Doolittle hydropathy profile of $MUB_{70}$ was generated using ExPASy bioinformatical tools. (FIG. 7C) Validation of biot-$MUB_{70}$ purity by gel filtration chromatography on Superdex 200 5/150 GL column. (FIG. 7D) Partition coefficients ($K_{av}$) of the standard proteins (ferritin, 440 kDa; aldolase, 158 kDa; ovalbumin, 43 kDa; ribonuclease A, 13.7 kDa; aprotinin, 6.5 kDa) were calculated according to $K_{av}=(V_e-V_0)/(V_t-V_0)$ ($V_e$, elution volume; $V_0$, void volume; $V_t$, total volume of the gel bed) and plotted against the corresponding molecular masses. The molecular mass of biot-$MUB_{70}$ calculated using the calibration curve equation: $\log(M_r)=3.12-3.1\ K_{av}$.

FIGS. 8A-8D. (FIG. 8A) Cell toxicity of Cy5-$MUB_{70}$ tested on HT-29-MTX and Hela epithelial cells. Cell survival was assessed using Sytoxgreen dye on cultures exposed to 1 µg/mL Cy5-MUB$_{70}$ from 0 to 10 h, as indicated. NS indicates P>0.05 (Student's T-test). (FIG. 8B) Rabbit colonic and ileal mucus staining on fixed tissues (PFA 4%), using Cy5-MUB$_{70}$ (1 µg/mL) (blue). Actin is stained in red (Phall.-RRX). Bar is 50 µm. (FIG. 8C) Human ex vivo colon sample was incubated for 2 h with 1 µg/mL Cy5-MUB$_{70}$ in a serum-free media. Resulting fluorescent staining was assessed using a two-photons microscope (see Methods). Z-projection, performed using ImageJ software, allows 3D localization of Cy5-MUB$_{70}$ fluorescence signal. Bar is 100 µm. Colon scheme: firmly (f) and loosely (l) attached colonic mucus layers are represented at the surface of the epithelium (e). (FIG. 8D) Kinetics of colonic mucus with Cy5-MUB$_{70}$. 3D reconstruction (isosurface representation) shows the colonic epithelium covered by the mucus layer (up to 1 000 µm) after 60, 90 and 120 min of incubation with Cy5-MUB$_{70}$. Human tissue autofluorescence is detected in the same red channel as Cy5.

Figure 9A:
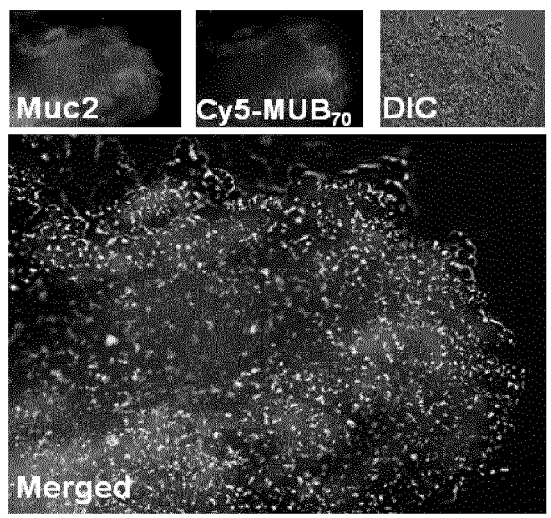
Figure 9B:
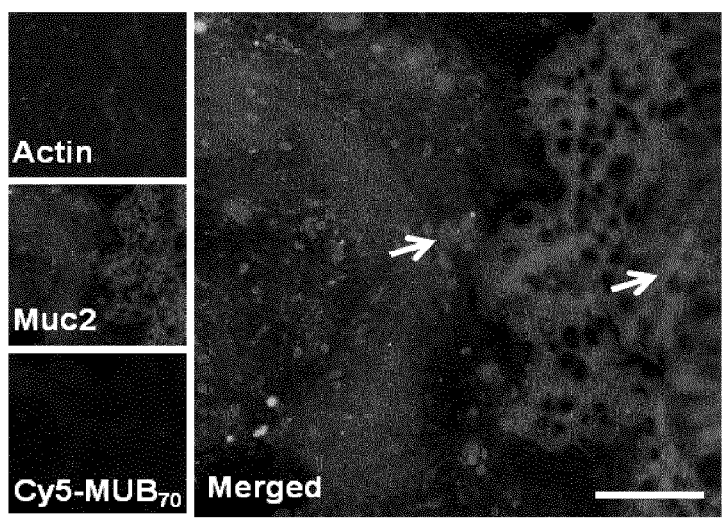

FIGS. 9A-9B. (FIG. 9A) Co-localization of Muc2 (green) and Cy5-MUB (blue) performed by immunofluorescent detection on human mucus extract collected on ex vivo tissues using an epifluorescent microscope. Bar is 50 µm. (FIG. 9B) Co-localization of Muc2 (green) and Cy5-MUB (blue) observed on fixed (PFA 4%) rabbit colon samples. Actin is stained in red (Phall.RRX). Observations are performed using a confocal microscope. Bars is 40 µm.

Figure 10A:
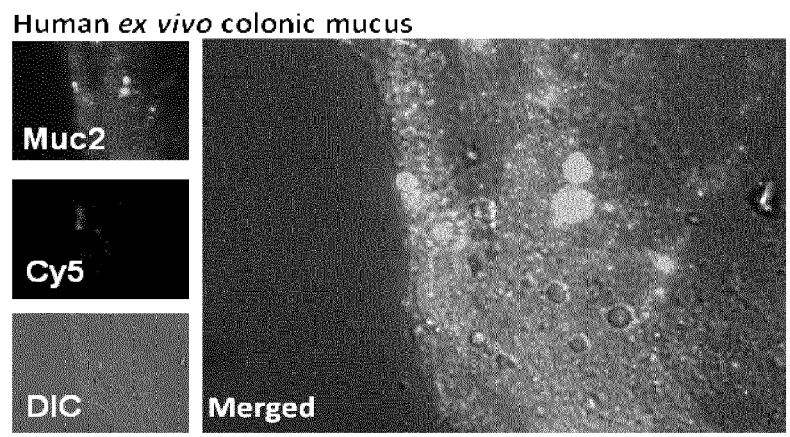
Figure 10B:
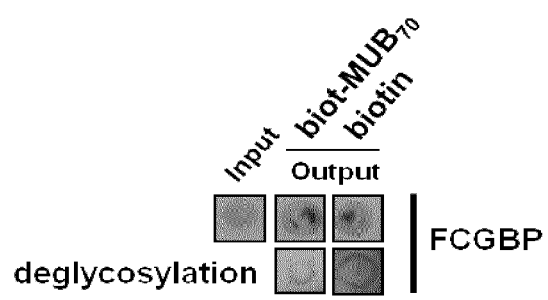

FIGS. 10A-10B. (FIG. 10A) Human mucus negative staining using Cy5 (blue). Muc2 (green) is used as a positive control. Observations were performed by immunofluorescent detection on human mucus extract collected on ex vivo tissues using an epifluorescent microscope. Bar is 50 µm. (FIG. 10B) Immunodetection of FCGBP (dotblot analysis) on human mucus extracts eluted after a pulldown assay performed with biot-MUB$_{70}$ on avidin conjugated beads (see Methods). Biotin is used as a negative control. Immunodetection of FCGBP (dotblot analysis) on deglycosylated mucus extracts and eluted after a pulldown assay performed with biot-MUB$_{70}$ on avidin conjugated beads. Non-deglycosylated mucus extract is used as a positive control.

Figure 11A:
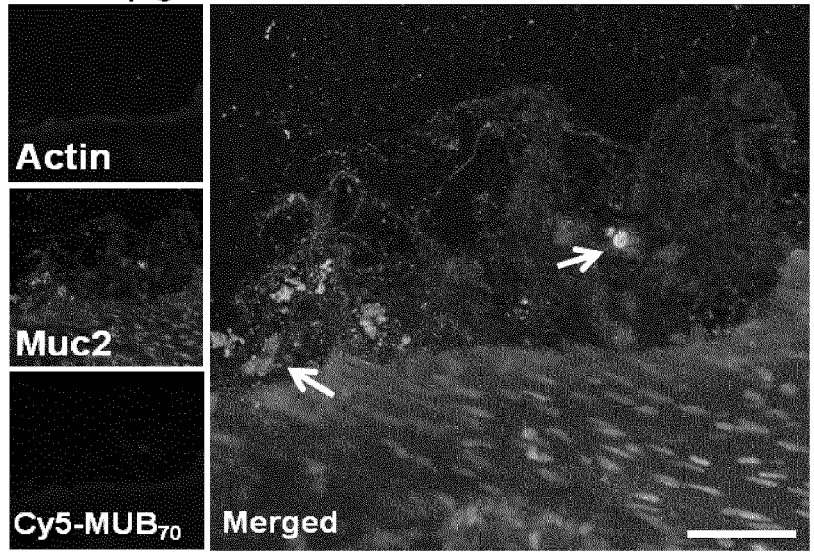
Figure 11B:
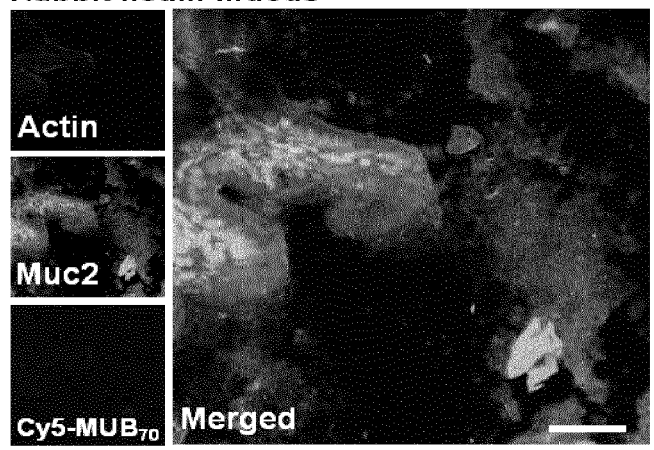
Figure 11C:
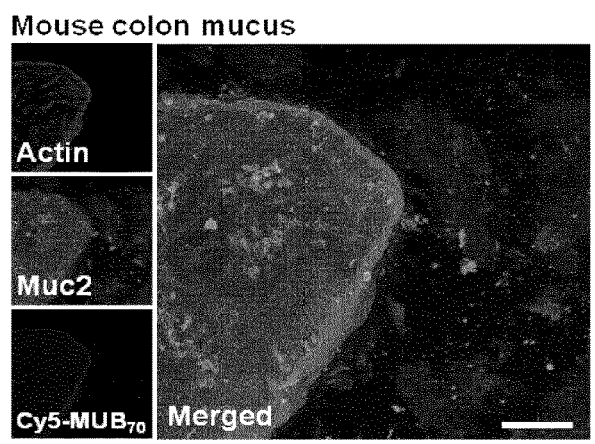

FIGS. 11A-11C. Mucus staining using Cy5-MUB$_{70}$ on fixed tissues. (FIG. 11A) Guinea pig colon, (FIG. 11B) rabbit ileum and (FIG. 11C) mouse colon were fixed in PFA 4%. Immunofluorescent staining was performed using Cy5-MUB$_{70}$ (1 µg/mL) (blue). Actin is stained in red (Phall.-RRX), Muc2 is stained in green (α-Muc2). Observations were performed using a confocal microscope. Bar is 50 µm.

FIG. 12. ClustalW sequence alignments of MUB domain repeats 1 to 13 found in L reuteri AF120104 and disclosed in Table 1 (SEQ ID NO: 5 to SEQ ID NO: 16). Figure discloses SEQ ID NOS 11, 11, 10, 12-14, 9, 15, 6, 5, 7, 8 and 16, respectively, in order of appearance.

Figure 13:
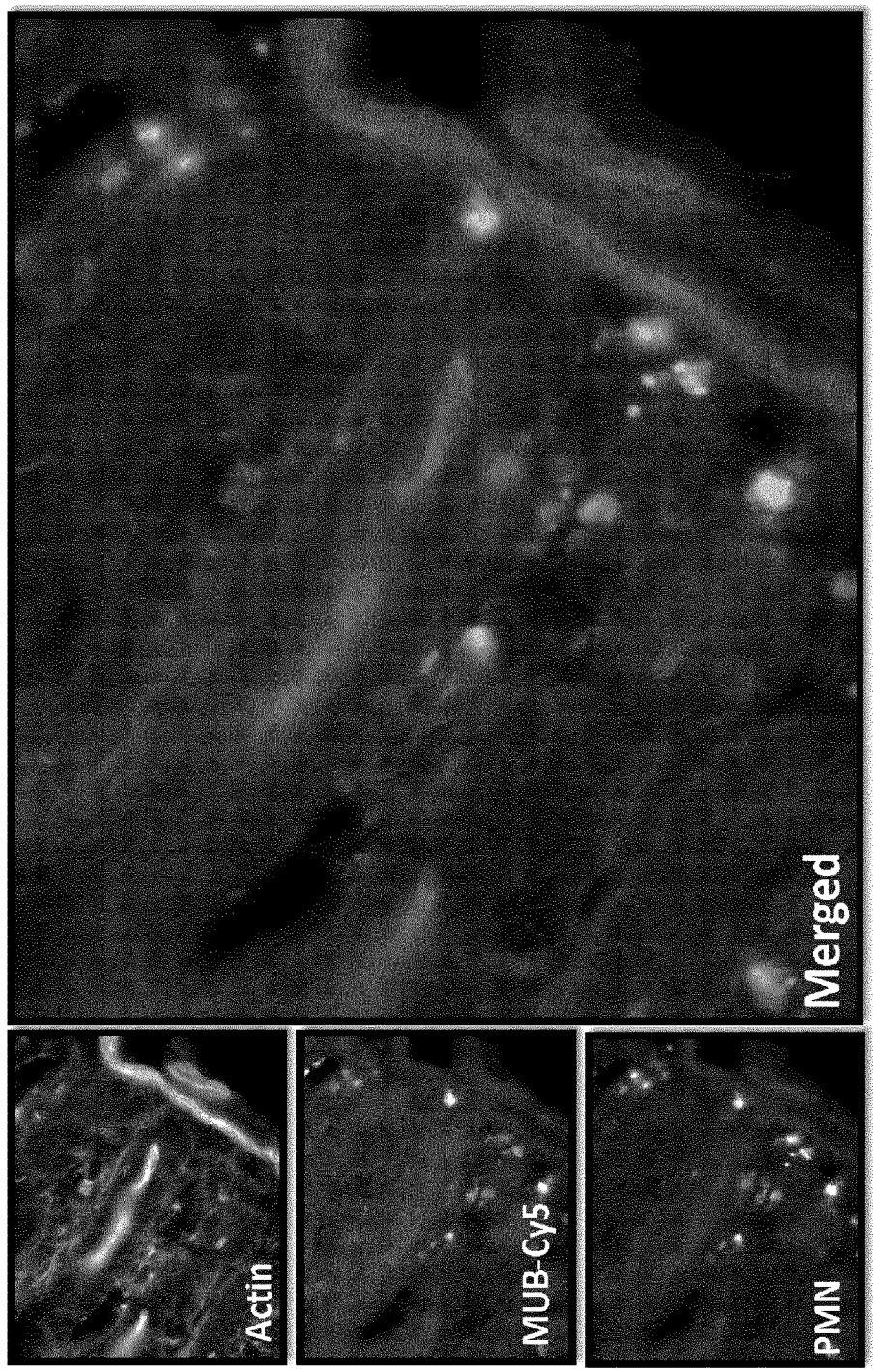

FIG. 13. Staining of individual neutrophiles (white blood cells) in rabbit ileum sub-mucosa. Cy5-MUB70 was incubated on PFA 4% fixed tissues. Signal was colocalized with an α-elastase (PMN) signal. (Primary antibody is α-elastase (PMN) 1:400 and secondary antibody is anti-mouse GFP 1:400, MUBCys5 1:400, Phalloidin-RRX 1:400). This result indicates that Cy5-MUB70 is binding specifically a neutrophile component. In particular, granules staining is achieved.

Figure 14:
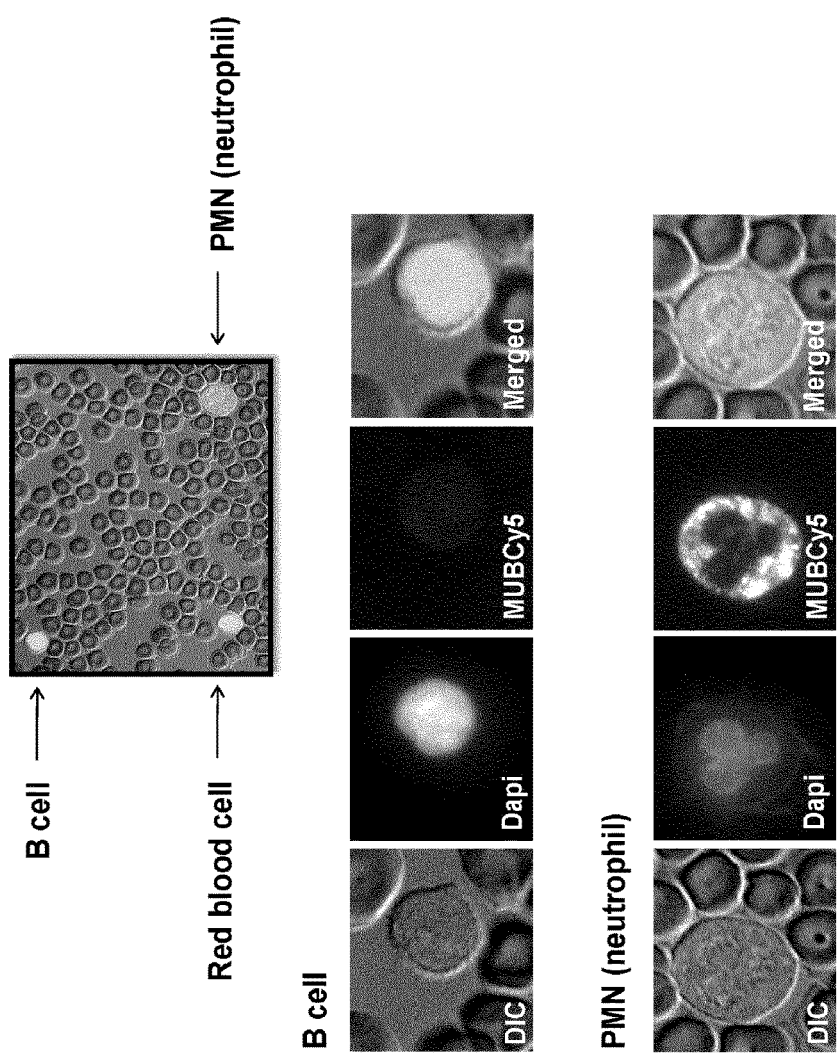

FIG. 14. Staining of individual neutrophiles (white blood cells) in human blood sample. Cy5-MUB70 was incubated on ethanol 100% fixed blood sample. Signal was detected as diffused in neutrophile cytoplasm, due to membrane solubilisation following alcoholic fixation. (Details are provided on the Figure). This result confirms that Cy5-MUB70 is binding specifically a neutrophile component. In particular, granules staining is achieved.

Figure 15:
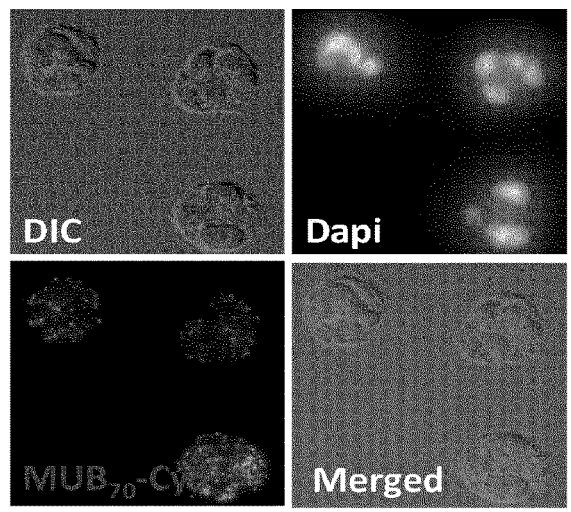

FIG. 15. Staining of individual neutrophiles (white blood cells) purified from fresh human blood sample. Cy5-MUB70 was incubated on PFA 4% fixed neutrophiles (PFA treatment for 15 min, wash 3 times in PBS). Signal was detected as dots distributed in neutrophile cytoplasms. (Staining with Dapi 1:1000 and EB1C5 1:1000 in PBS+10% FCS+0.1% Saponin). This result indicates that Cy5-MUB70 is binding specifically a neutrophile granule component. In particular, granules staining is achieved.

FIGS. 16A-16E. GenBank data under access number AF120104.1 relating to the Mub protein sequence of L. reuteri and the corresponding nucleic acid sequence (SEQ ID NOS 17 and 18).

FIG. 17. MUB$_{40}$ operating sequences (with Cysteine residues at N-terminal extremities) synthesis strategies description (SEQ ID NOS 62, 63, 64 and 65). Operating sequences for designed synthesis of peptides having SEQ ID NOS 58, 59, 60 and 61 as described herein, with Cysteine residues at their N-terminal extremities, where secondary amino acid surrogates are underlined (pseudoproline dipeptides) or in bold (Dmb dipeptides). Proline residues are in italic bold.

Figure 18:
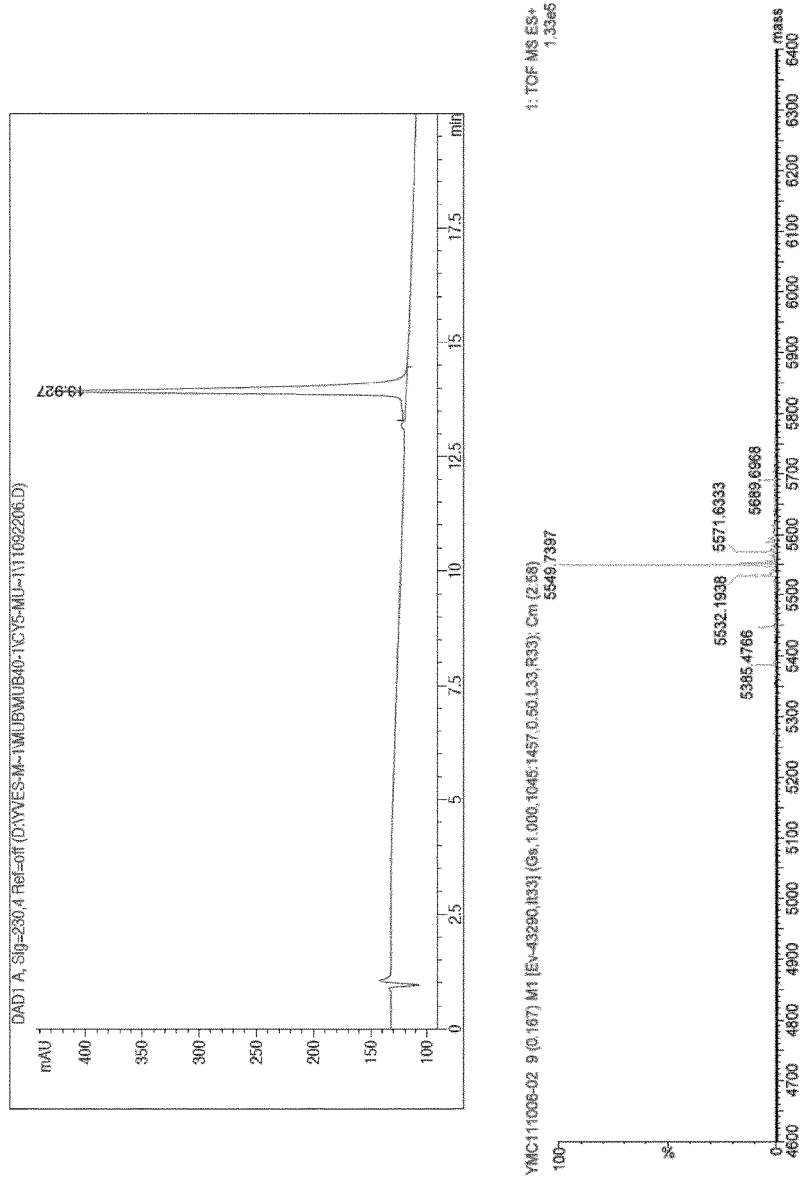

FIG. 18. HPLC analysis of the Cy5-MUB40-1 peptide. Retention time of 13.927 min and Molecular weight of 5549 were obtained.

Figure 19:
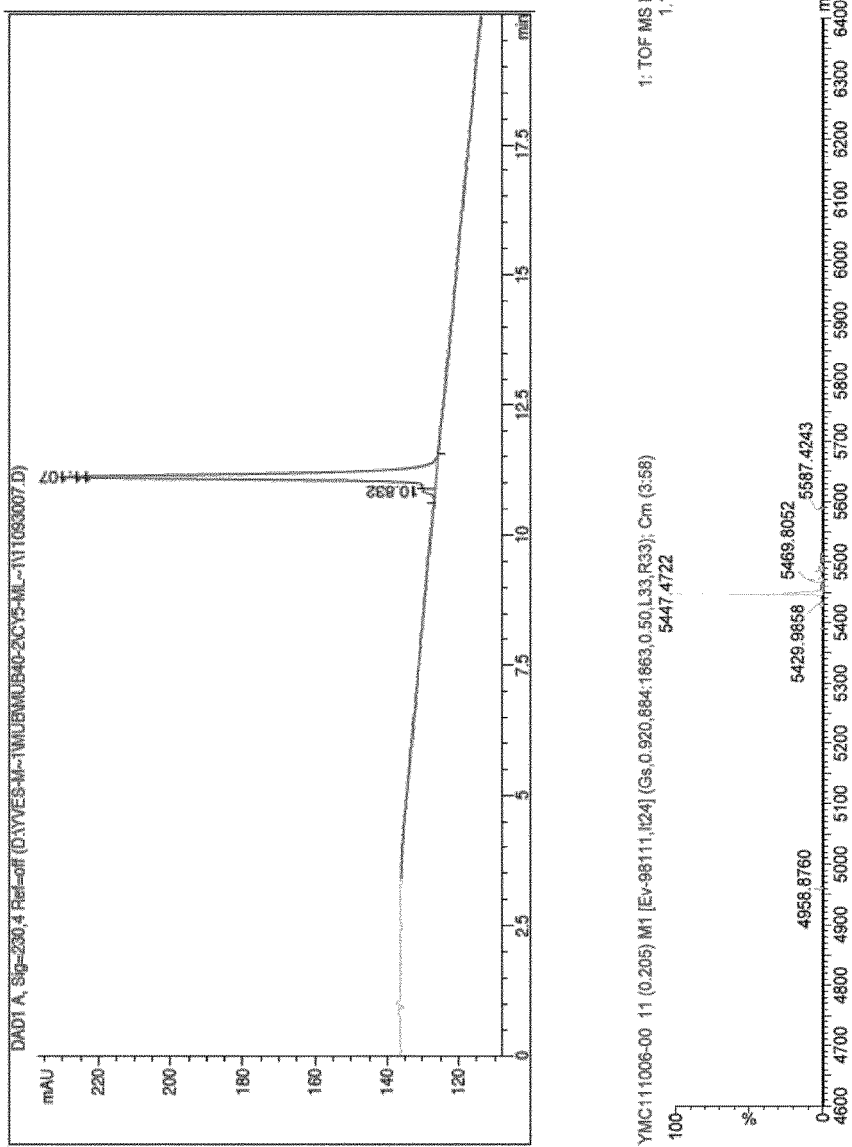

FIG. 19. HPLC analysis of the Cy5-MUB40-2 peptide. Retention time of 11.107 min and Molecular weight of 5547 were obtained.

Figure 20:
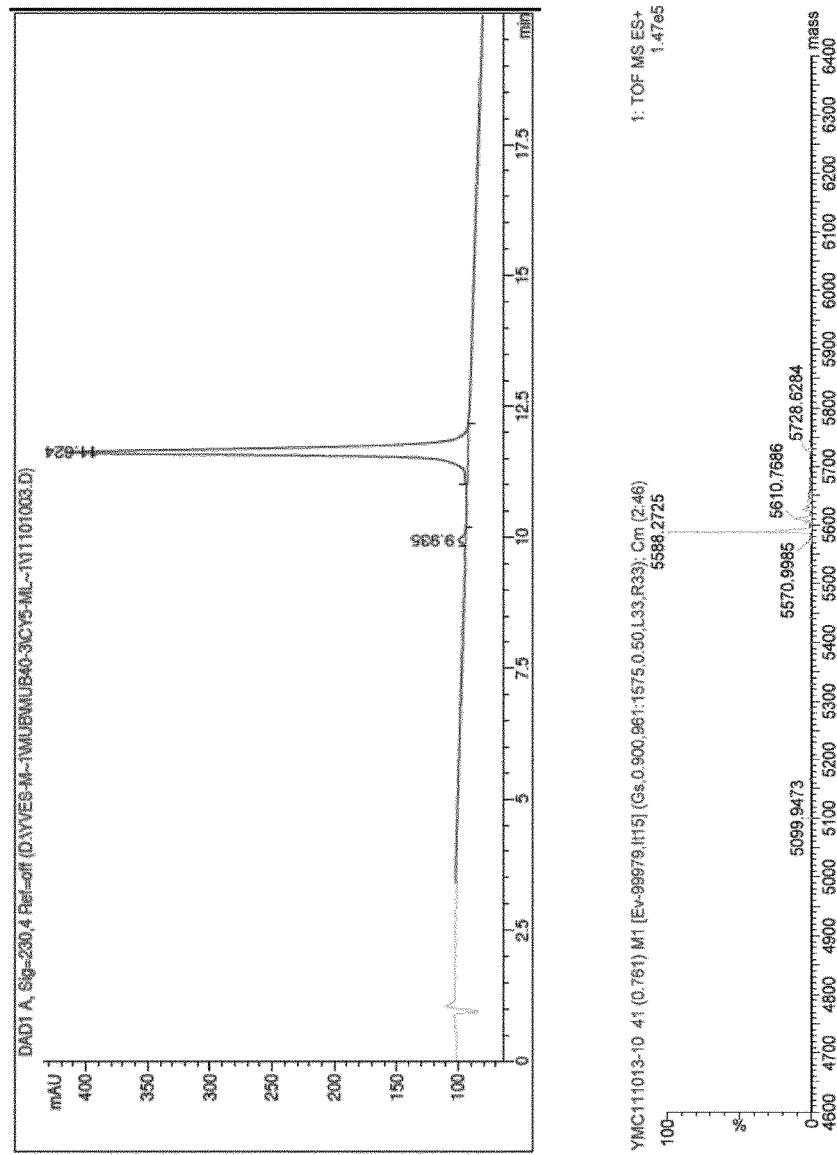

FIG. 20. HPLC analysis of the Cy5-MUB40-3 peptide. Retention time of 11.624 min and Molecular weight of 5588 were obtained.

Figure 21:
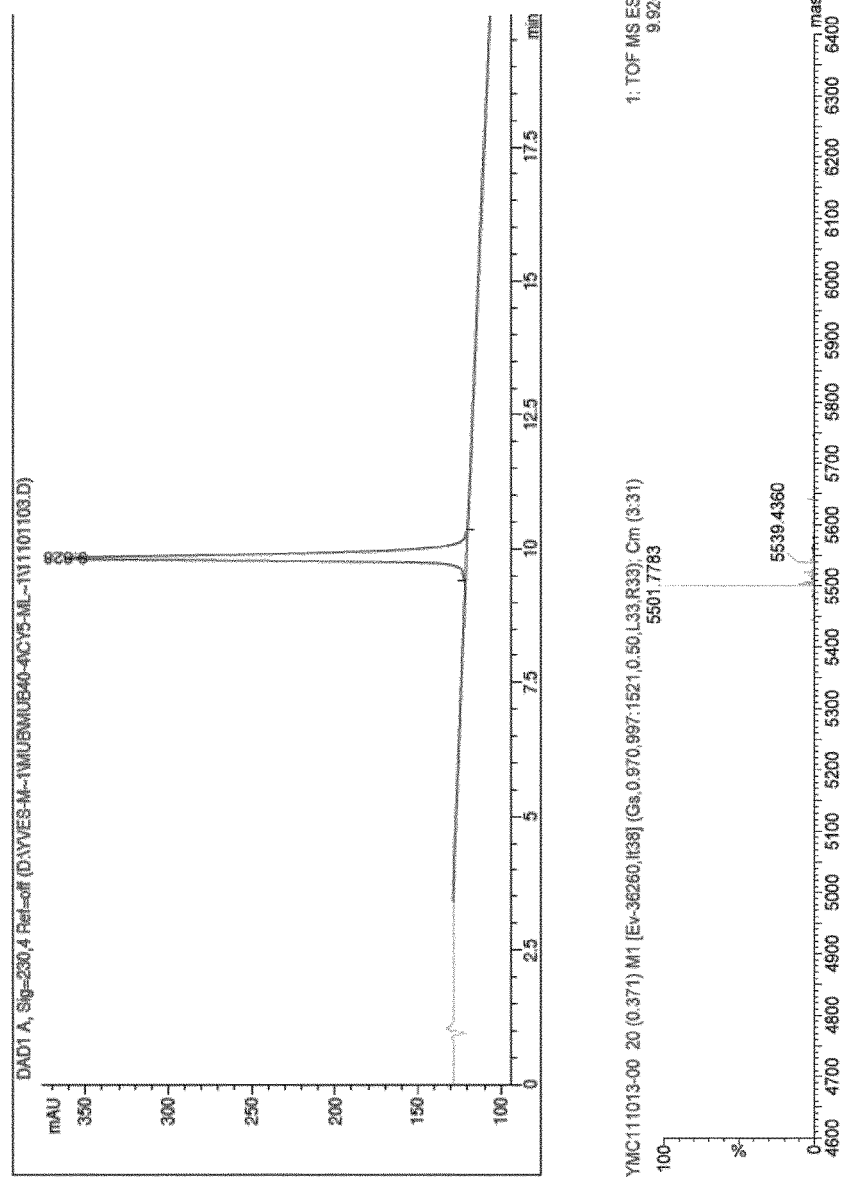

FIG. 21. HPLC analysis of the Cy5-MUB40-4 peptide. Retention time of 9.828 min and Molecular weight of 5501 were obtained.

Figure 22:
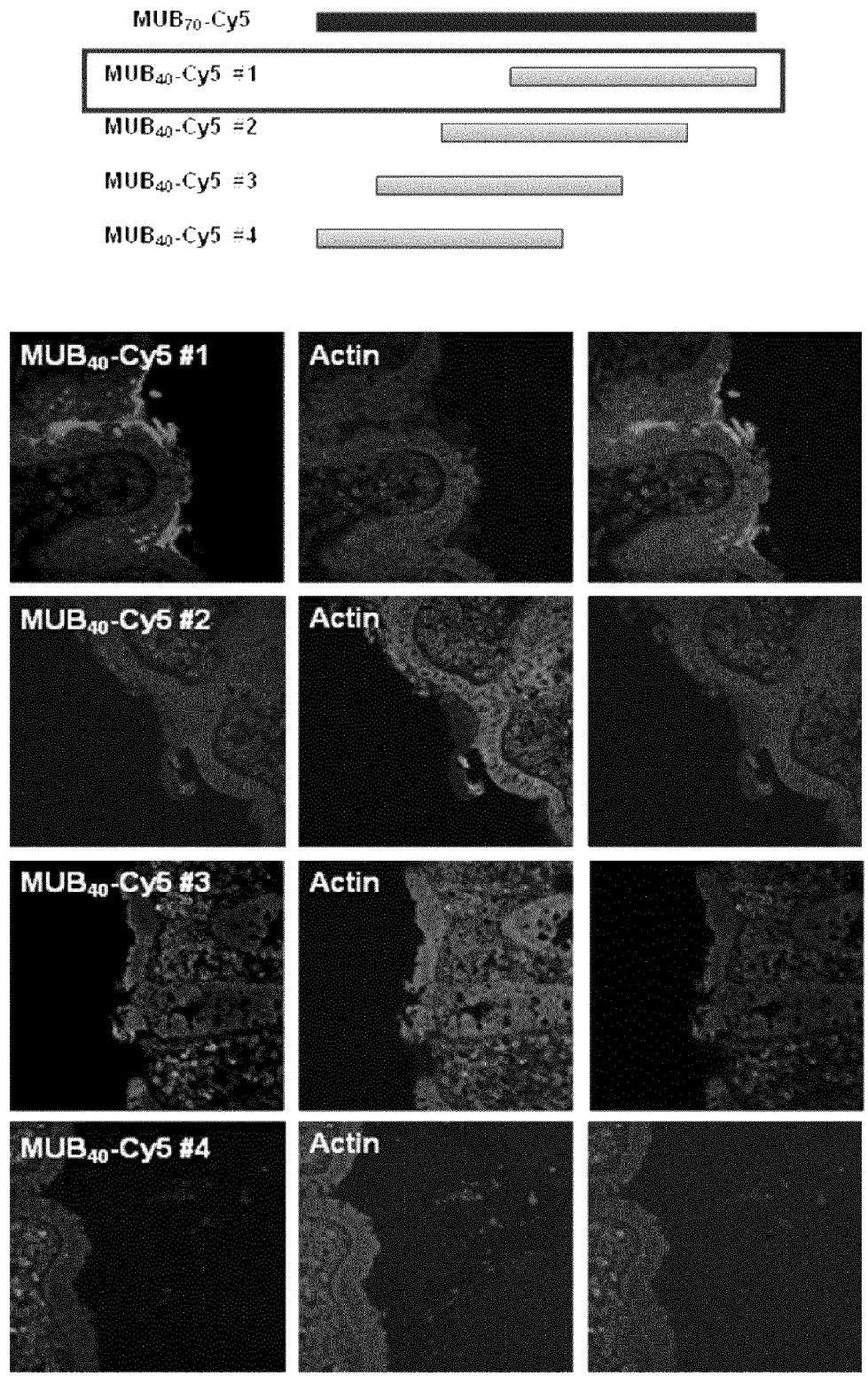

FIG. 22. Schematic description of the Cy5-MUB40-1, Cy5-MUB40-2, Cy5-MUB40-3, Cy5-MUB40-4 peptides (SEQ ID NOS 62 to 65). Fluorescent staining of human colonic mucus was performed by the addition of 1 µg/mL of the corresponding Cy5-conjugated peptides with Phalloidin-RRX (1:100) on formol fixed, paraffin embedded samples. Image acquisition was performed using a fluorescent confocal microscope (see Methods).

FIG. 23 Comparative staining analysis of human colonic goblet cells using Cy5-MUB70 and Cy5-MUB40-1. Fluorescent staining of human colonic mucus was performed by the addition of 1 µg/mL of the corresponding Cy5-conjugated peptides with Phalloidin-RRX (1:100) on formol fixed, paraffin embedded samples. Image acquisition was performed using a fluorescent confocal microscope (see Methods).

Figure 24A:
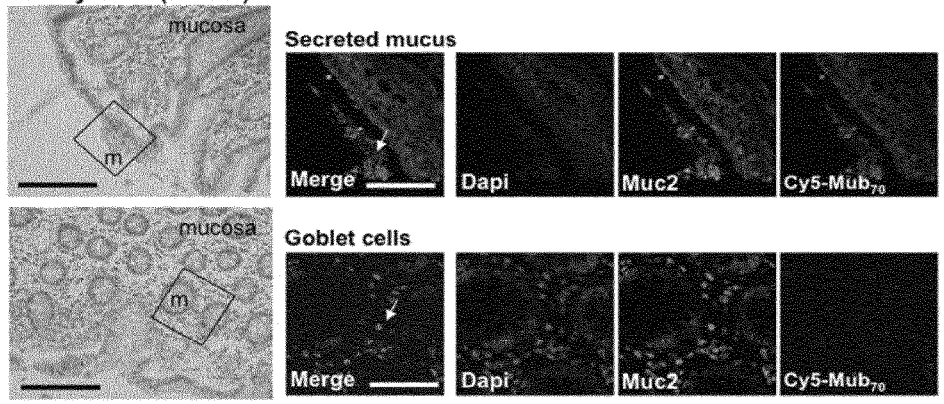
Figure 24B:
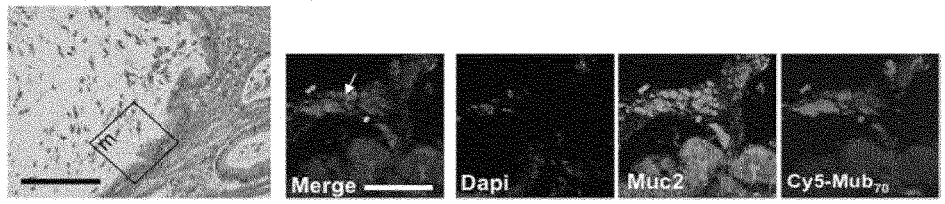

FIGS. 24A-24B. Comparative human colonic mucus staining using MUB70-Cy5 on healthy tissues and mucinous carcinomas (Coic et al, JBC, 2012 (41)). Fluorescent staining of human colonic mucus was performed by the addition of 1 µg/mL of the corresponding Cy5-conjugated peptides with Phalloidin-RRX (1:100) on formol fixed, paraffin embedded samples. Image acquisition was performed using a fluorescent confocal microscope (see Methods).

Figure 25:
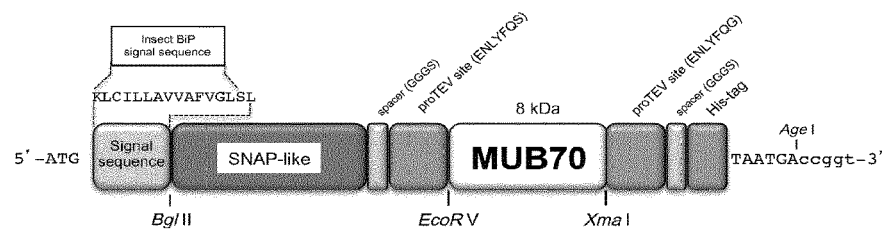

FIG. 25. Schematic description of the MUB70-SNAP cloning strategy. S2 insect cell line was stably transfected using a DeSNAPuniv-MUB70 plasmid in order to allow the overexpression and the secretion of MUB70-SNAP in the cell culture media (see Methods). Figure discloses SEQ ID NOS 85-88, 86, and 89, respectively, in order of appearance.

Figure 26:
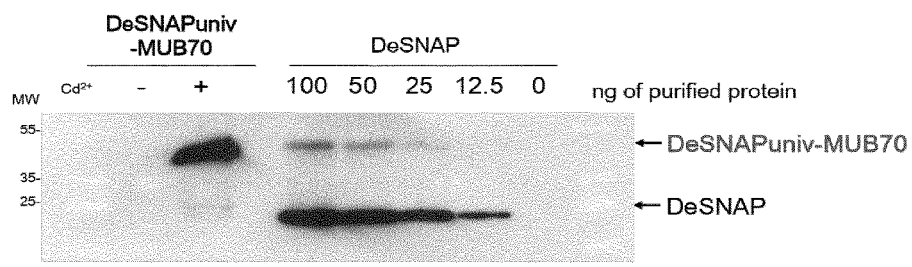

FIG. 26. MUB70-SNAP secretion detection in S2 insect cell lines stably transfected with pDeSNAPuniv-MUB70 was induced by the addition of 5 µg/mL CdCl$_2$. MUB70-

SNAP was detected in 10 μL of the cell culture media by Western blot using an anti-SNAP antibody. The detection of the secretion of SNAP using an empty pDeSNAP vector was used as a control.

Figure 27:
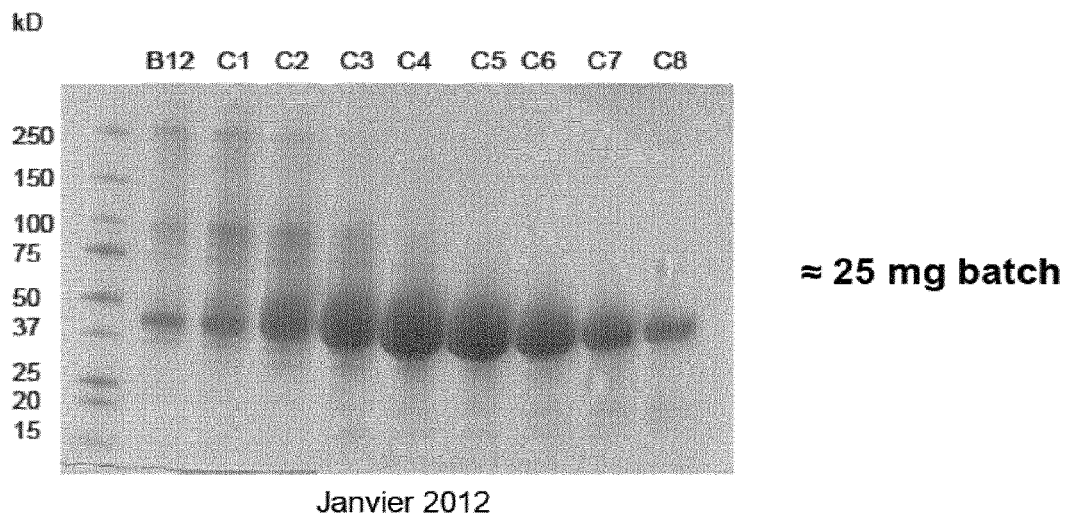

FIG. 27. MUB70 protein production in S2 cells. MUB70-SNAP production in stable transfected S2 insect cells was performed in 1 L of culture media. Following two purification steps (see Methods) the gel filtration fractions were loaded onto a SDS Page gel further stained by Coomassie. 25 mg of MUB70-SNAP were obtained from 1 production batch.

Figure 28:
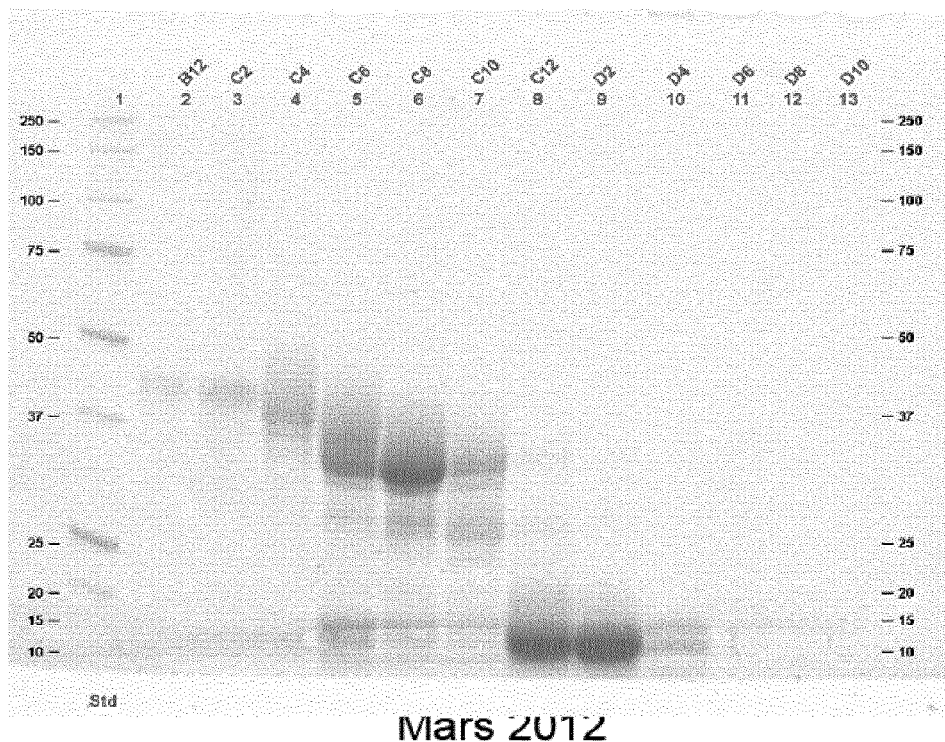

FIG. 28. MUB70-SNAP is not stable at 4° C. as after 3 months of storage in these conditions, some degradation products are detected by gel filtration (see Methods, second purification step).

Figure 29:
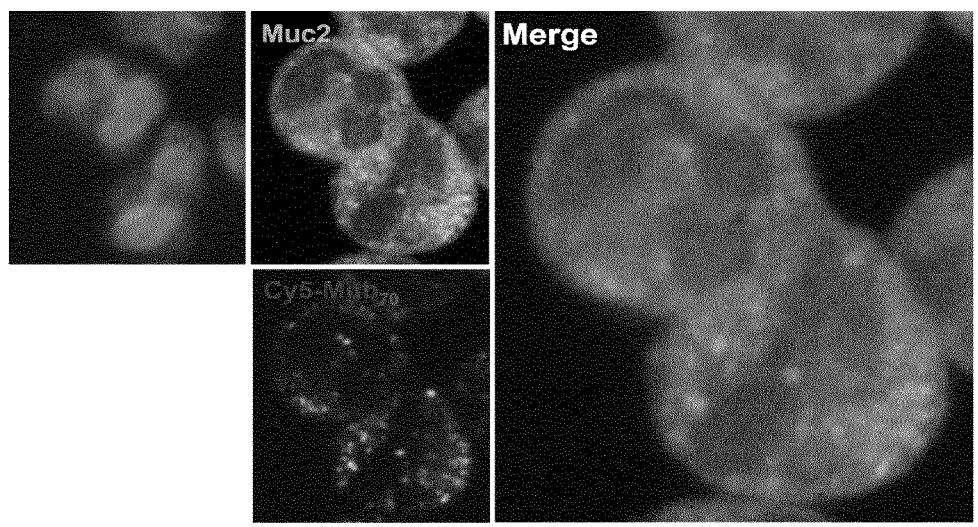

FIG. 29. Identification of Muc2 in neutrophile granules using MUB70-Cy5. Human neutrophil (PMN) granule staining using Cy5-MUB70. PMN were purified from healthy donor blood samples and fixed in the presence of 4% PFA. Fluorescent staining of human colonic mucus was performed by the addition of 1 μg/mL of Cy5-MUB70 (Red) with Dapi (1:100) (Blue) and 1:200 anti-Muc2 antibody (Green). Image acquisition was performed using a fluorescent confocal microscope (see Methods).

Figure 30:
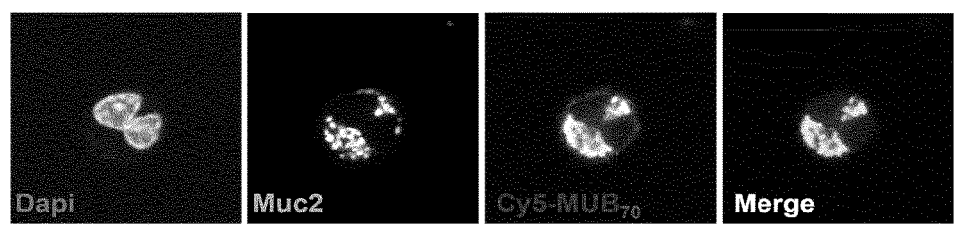

FIG. 30. Identification of Muc2 in neutrophile granules using MUB70-Cy5. Activated (+Shigella flexneri) human neutrophil (PMN) granule staining using Cy5-MUB70. PMN were purified from healthy donor blood samples and incubated with Shigella flexneri (MOI 20) during 15 min prior fixation in the presence of 4% PFA. Fluorescent staining of human colonic mucus was performed by the addition of 1 μg/mL of Cy5-MUB70 (Red) with Dapi (1:100) (Blue) and 1:200 anti-Muc2 antibody (Green). Image acquisition was performed using a fluorescent confocal microscope (see Methods). PMN activation (addition of Shigella flexneri) leads to an increase of the Muc2 accumulation in the granules.

Figure 31:
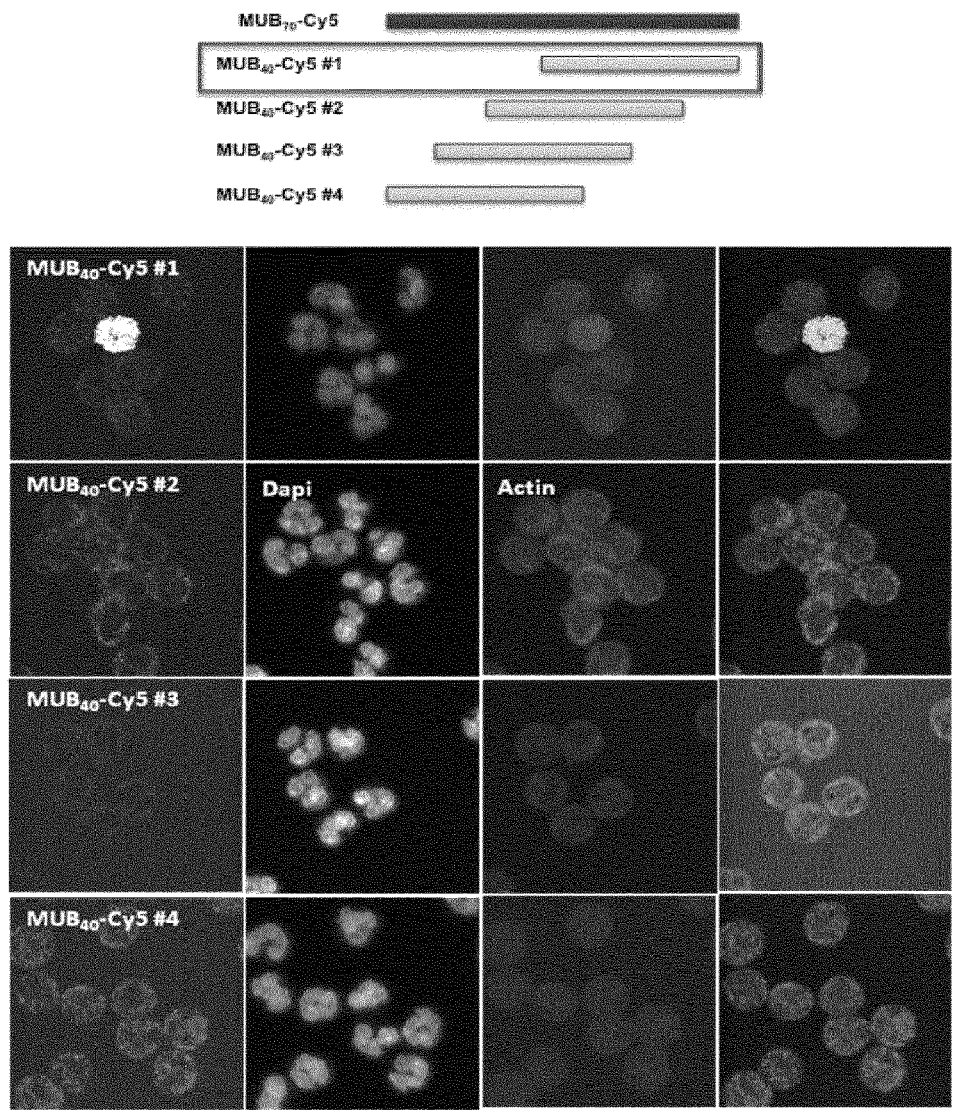

FIG. 31. Identification of Muc2 in neutrophile granules. Human neutrophil (PMN) granule staining using Cy5-MUB40-1, Cy5-MUB40-2, Cy5-MUB40-3, Cy5-MUB40-4 peptides. Schematic description of the Cy5-conjugated peptides. PMN were purified from healthy donor blood samples and fixed in the presence of 4% PFA. Fluorescent staining of human colonic mucus was performed by the addition of 1 μg/mL of the Cy5-conjugated peptides (Green) with Dapi (1:100) (Blue) and Phalloidin-RRX (1:1000) (Red). Image acquisition was performed using a fluorescent confocal microscope (see Methods).

FIG. 32. BLAST alignment performed between MUB40-1 sequence (SEQ ID NO: 62) and corresponding sequences in several species to identify MUB40-1 variants (SEQ ID NO: 69 to SEQ ID NO: 83). $MUB_{40-1}$ sequence is in bold. Conserved patterns P8, P9 and P10, as detailed herein, are indicated and highlighted in light and/or dark gray. Perfect match over all compared sequences are identified with an asterisk. Good matches are identified with a double dot or a dot.

EXAMPLES

A. Materials and Methods

Chemical Synthesis
$MUB_{70}$ Synthesis.

Synthesis was carried out on an ABI 433 synthesizer (Applied Biosystems, Foster City, Calif., USA) equipped with a conductivity flow cell to monitor Fmoc deprotection. PS-PHB-Phe Fmoc resin (capacity 0.52 mmol/g) was purchased from Rapp Polymere GmbH (Tubingen, Germany). Dmb- and pseudoproline (oxazolidine) dipeptides were purchased from Merck-Novabiochem (Darmstadt, Germany). Standard Fmoc amino acids were obtained from Applied Biosystems, and side-protected as followed: tBu for aspartic acid, glutamic acid, serine, threonine and tyrosine, trityl for cysteine, histidine, Boc for lysine, and 2,2,4,6,7-pentamethyl-dihydrobenzofuran-5-sulfonyl for arginine. Fmoc-amino acids and pseudoproline dipeptides were activated with HATU/DIPEA and single coupled with a eightfold molar excess with regard to the resin. Both coupling reagents, as well as N-methyl pyrrolidone (NMP), were purchased from Applied Biosystems. Piperidine was purchased from Sigma-Aldrich (St Louis, Mo., USA). (Synthesis yield 85.4%). Synthesized peptide was collected through classical resin cleavage and HPLC detection techniques. Purification was achieved using a three-step purification method on the dimeric form of $MUB_{70}$. Biotin and Cy5 conjugations are described herein.

Any synthesized peptide mass was calculated using electrospray ionization mass spectrometry.

MUB40-Peptides Chemical Synthesis:

The synthesis strategy used for synthesizing the MUB70 fragment has also been used for synthesizing the overlapping four shorter Mub40 sequences (41). Taking into account the necessity to introduce secondary amino acid surrogates to obtain MUB70, the inventors have preserved in the MUB40 operating sequences both Dmb and pseudoproline dipeptides incorporation in the positions which have been shown to be beneficial (see FIG. 17). As a result, lowering of aggregation propensity and aspartimide formation produced the MUB40 peptides with a satisfactory yield.

Synthesis and Cleavage.

The synthesis were carried out on an ABI 433 synthesizer (Applied Biosystems, Foster City, Calif.) equipped with a conductivity flow cell to monitor Fmoc deprotection, from a polystyrene AM-RAM resin (capacity 0.41 mmol/g, Rapp Polymere GmbH). Fmoc amino acids, Dmb, and pseudoproline dipeptides were activated with HCTU (2-(6-Chloro-1H-benzotriazole-1-yl)-1,1,3,3-tetramethylaminium hexafluorophosphate)/DIPEA (N,N-diisopropylethylamine) and single-coupled with an eight-fold molar excess regarding the resin. Fmoc-Asp(OtBu)-(Dmb)Gly-OH dipeptides and pseudoproline (oxazolidine) dipeptides were purchased from Merck-Novabiochem. Both coupling reagents, N-methyl pyrrolidone (NMP) and standard Fmoc amino acids were obtained from Applied Biosystems. Fmoc amino acids were side-protected as followed: tBu for aspartic acid, glutamic acid, serine, threonine and tyrosine, trityl for cysteine, histidine, Boc for lysine, and 2,2,4,6,7-pentamethyl-dihydrobenzofuran-5-sulfonyl (Pbf) for arginine. Piperidine was purchased from Sigma-Aldrich (St Louis, Mo., USA).

N-terminal acetylation was achieved by treating the peptide resin at the end of the synthesis with acetic anhydride for 30 minutes. As a result, the Mub40 peptides were N-terminal amide and C-terminal acetylated.

Cleavage from the solid support and deprotection of the amino acid side chains were accomplished in one step by treatment with 92.5:2.5:2.5:2.5 mixture of TFA (Applied Biosystems), ethanedithiol, triisopropylsilane (Sigma-Aldrich) and water for 3 h at room temperature. After filtration of the resin, the cleavage mixture was poured into ice-cold diethyl ether. The precipitate was recovered by centrifugation, washed three times, dried, resuspended in a mixture of water and acetonitrile and freeze dried.

HPLC Analysis.

Analysis of crude mixtures and purity control of the final peptides were performed by RP-HPLC on an Agilent (Santa Clara, Calif., USA) 1100 Series liquid chromatograph and monitored with a photodiode array detector by absorbance at 230 nm, according to the following methods. A linear gradient from 15% to 40% of acetonitrile in aqueous solvent A (50 mM ammonium acetate, pH 6.5) over 20 min was applied at a 0.35 ml/min flow rate on a Symmetry 300 C18 3.5 µm 2.1×100 mm column (Waters, Manchester, UK).

Purification.

The free sulfhydryl crude peptides Mub40-1, 2 & 3 were solubilized at a final concentration of 20 mg/ml in a mixture of solvent A and acetonitrile, 8:2 v/v. Crude Mub40-4 was solubilized at the same concentration in water with aqueous ammoniac (pH8) and 10 equivalent of DTT (1,4-Dithio-DL-threitol). Those materials were purified by RP-MPLC (AP-100/200 flash, Armen Instrument, Saint Ave, France) on a preparative column (26×313 mm) packed with 100 Å 20 µm C18 Nucleoprep packing (Macherey & Nagel GmbH & Co, Düren, Germany), by applying a linear gradient of 15-70% solvent B (mixture of acetonitrile and solvent A, 8:2 v/v) in solvent A over 60 min at a 20 ml/min flow rate. The purification was monitored at 214 nm (UV detector K2501, Knauer, Berlin, Germany). The suitable fractions were pooled and freeze dried. The overall isolated yields (from 20% to 30%) were in concordance with the observed synthesis yields deducted from the crude's HPLC analysis.

Conjugation.

The Cy5 conjugation was operated in a 0.1 M Phosphate buffer pH=6, using 1.2 equivalent of the correspondent maleimide derivative (InvitroGen) in the presence of 1.5 equivalent of TCEP (Tris(2-carboxyethyl)phosphine) per mole of cysteine residue. The labeled peptides were purified after 30 minutes of coupling reaction by RP-HPLC on a nucleosil 5 µm C18 300 Å semi-preparative column, using a linear gradient of 15-40% acetonitrile in solvent A over 20 min at a 6 ml/min flow rate. The purity was checked according the former described HPLC analytical method. The exact concentration was determined by quantitative amino acid analysis (Hitachi, L-8800 analyzer), giving from 50% to 60% conjugation yield.

Electrospray Ionisation Mass Spectrometry.

Mass spectrometry was carried out on a quadrupole-TOF Micro mass spectrometer (Waters) equipped with a Z-spray API source and calibrated with a phosphoric acid calibration solution. Capillary, sample cone and extraction cone voltages were set at 3 kV, 40V and 10V, respectively. Source and desolvation temperatures were set at 80 and 250° C., respectively. Data were acquired by scanning over the m/z range 150-2000 at a scan rate of 1 s and an interscan delay of 0.1 s. Peptides were dissolved in a mixture of water/methanol/acetic acid 49.5/49.5/1 v/v/v at a concentration of 1 µg/µl and analysed in positive-ion mode by infusion at a flow rate of 5 µl/min. About fifty spectra were combined and the resultant raw multicharged spectra were processed using the MaxEnt1 deconvolution algorithm embedded in the Masslynx software. Given the deconvolution process of MaxEnt1, applied to the charged molecules (the Cy5 moiety is positively charged), final characterization was consistent with the expected masses: Cy5-labeled MUB40-1: experimental 5549,740—expected 5550,115; Cy5-labeled MUB40-2: experimental 5447,472—expected 5447,933; Cy5-labeled MUB40-3: experimental 5588,273—expected 5589,170; Cy5-labeled MUB40-4: experimental 5501, 778—expected 5502,093. Characterization data is provided in FIGS. 18, 19, 20 and 21.

Biochemical Characterization and Biological Properties
Analytical Gel Filtration.

25 µg of biot-$MUB_{70}$ was applied with a flow rate of 0.2 ml/min to a Superdex™ 5/150 column (Tricorn™) (GE Healthcare, Uppsala, Sweden) that was equilibrated with 5 CV of gel filtration buffer (25 mM TRIS, 150 mM NaCl, pH 7.5) at 4° C. before use. Standard proteins from the gel filtration calibration kit (ferritin, aldolase, ovalbumin, ribonuclease A, aprotinin; GE Healthcare, Uppsala, Sweden) were used for calibration. As control biot-$MUB_{70}$ was visualized on 10% SDS-PAGE gel stained by Coomassie.

Colonic Tissue Collection.

Ex vivo human colon samples were obtained from Dr. E. Labruyère (Institut Pasteur) and tissue processing was performed as described previously [27] and stored in serum free RMPI media (surgical procedure is described herein). Human mucinous carcinoma formamide fixed samples were obtained from Dr. T. Lazure (Hôpitaux Universitaires Paris-Sud, Kremlin-Bicêtre) and Pr. I. Sobhani (Hôpital Henri Mondor, Créteil). Rabbit colon and ileum samples were collected on naïve New Zealand white rabbits weighting 2.5-3 kg and fixed in PFA 3%. Same procedure was applied on intestine samples collected on guinea pigs (Charles River) and C57/B6 mice (Janvier).

Cell Culture.

Hela cells were grown in DMEM medium supplemental with 10% FCS. HT-29 MTX colonic epithelial cells [28] were grown to confluency in 24-well tissue culture plates in RPMI medium supplemented with 10% FCS and 1% essential amino acids. Mucus production in HT-29 MTX cells was observed after 21 days. Cell viability was determined by staining with Sytox Green (Invitrogen) as described by the manufacturer. Sytox Green only penetrates into and stains the DNA of non-viable cells. As a positive control, cells were killed by incubation in 3% PFA for 15 min (data not shown). Fluorescence was measured using a FACS flow cytometer (BD systems) recording at least 10,000 events. Data were analysed with CellQuest Pro software (BD Biosciences), and expressed as percentage survival.

Antibodies and $MUB_{70}$ Probes.

For immunofluorescence assay mouse α-MUC2 pAbs (Santa Cruz sc-15334) was diluted 1:1000 and FITC-conjugated rabbit anti-mouse was diluted 1:2000. Host cells were detected with DAPI (nuclei, red) or using Phalloidin-Rhodamine red X (RRX)-conjugated donkey anti-mouse antibodies (Jackson Immunoresearch Antibodies) as an actin marker (stained red); both were used at a final dilution of 1:1000. Cy5-$MUB_{70}$ (1 mg/mL solution) was diluted 1:1000.

For dot blot assay, goat α-MUC2 pAbs (sc-13312, Santa Cruz), mouse α-MUC5ac (Abcam), mouse α-MUC5b mAbs (Abcam), mouse α-MUC6 mAbs (sc-33668, Santa Cruz), mouse α-lactoferrin mAbs (sc-52048, Santa Cruz) and rabbit α-FCGBP pAbs (Sigma-Aldrich) antibodies were used at a 1:100 dilution. Corresponding HRP-Conjugated antibodies were used at a 1:1000 dilution. For staining living HT-29 MTX cells and on human colon ex vivo model, Cy5-$MUB_{70}$ was incubated (1 µg/mL) in a serum starved culture medium (DMEM and RPMI respectively) for two hours at 37° C. prior observation.

Mucus Collection.

In order to perform a pulldown assay, soluble human colonic mucus extracts were initially obtained from HT-29 MTX cell secretion product (as described in [29]). Briefly, mucus was collected using cold PBS. After sonication and centrifugation (14000 rpm, 30 min), the supernatant containing the soluble mucus fraction was lyophilized (Labologic, Freeze Dryer). Eight independent batches of human mucus were processed.

Deglycosylation, Desialylation.

Mucus collected from HT-29 MTX (see above) was chemically deglycosylated using a GlycoProfile IV chemical deglycosylation kit (Sigma-Aldrich). Each treatment was performed on two independent samples. 4 mg of lyophilized mucus were processed per batch as recommended by the manufacturer. Desialylation and desulfatation were performed on 2 mg lyophilized mucus batches by adding respectively 1 mU/mL of *C. perfringens* neuraminidase (Neu1) (Sigma-Aldrich) in PBS 50 mM pH=6 and *A. aerogenes* sulfatase in TrisHCl 50 mM pH=7.25, KCl 100 mM and 10 mM $MgCl_2$. Reaction mixtures were incubated 2 h at 37° C.

Pulldown Assay.

Pulldown assays were performed in the presence of 600 µg biot-$MUB_{70}$ bound to 500 µL Avidin-agarose beads (Thermo Scientific) in a Phosphate Buffer pH=8 buffer for 1 h at 4° C. After 3 washes, 10 mg soluble human colonic mucus extract were incubated with the loaded beads for 2 h at 4° C. After 3 washes, beads were boiled in the presence of 1× Laemli buffer. As a negative control, Avidin-agarose beads were loaded with 15 µg biotin (Sigma-Aldrich) and processed using the same procedure. Experiments were performed on two independent occasions.

Dot Blot Assay.

Soluble mucus components used in pulldown assays (input and output) were transferred to nitrocellulose membranes (Invitrogen), which were blocked in PBS/5% milk and further incubated with the primary antibodies diluted in PBS/1% milk/0.01% Tween20 (Sigma-Aldrich) overnight. Membranes were washed in PBS three times, then incubated with secondary antibodies for 1 hr before washing. Antibody binding was detected with chemiluminescence (ECL kit, GE Healthcare).

Tissue Immunostaining.

Following PFA 4% or Carnoy fixation, as indicated, samples were washed in PBS, incubated at 4° C. in PBS containing 12% sucrose for 90 min, then in PBS with 18% sucrose overnight, and frozen in OCT (Sakura) on dry ice. 7 µm sections were obtained using a cryostat CM-3050 (Leica).

Fluorescence Microscopy.

Fluorescent labeled tissues and cells were observed using a widefield epifluorescent microscope (Zeiss Definite Focus), laser-scanning confocal microscope (Leica TCS SP5) or a two-photons confocal microscope (Zeiss LSM710), as indicated. Image analysis was performed using Axovision, ImageJ, Zen 2008 SP 1.1 (Zeiss) and Imaris softwares as indicated.

Cleavage from the Resin.

Cleavage from the solid support and deprotection of the amino acid side chains were accomplished in one step by treatment with 92.5:2.5:2.5:2.5 mixture of TFA (Applied Biosystems), ethanedithiol, triisopropylsilane (Sigma-Aldrich) and water for 3 h at room temperature. After filtration of the resin, the cleavage mixture was poured into ice-cold diethyl ether. The precipitate was recovered by centrifugation, washed three times, dried, resuspended in a mixture of aqueous acetic acid and acetonitrile and lyophilised. (cleavage yield 76%).

HPLC Analysis.

Analysis of crude mixtures and purity control of the final peptides were performed by RP-HPLC on an Agilent (Santa Clara, Calif., USA) 1100 Series liquid chromatograph and monitored with a photodiode array detector by absorbance at 230 nm, according to both following methods a or b. A linear gradient (from a/30% to 40% or b/15% to 40%) of B (acetonitrile) in aqueous solvent A (a/0.08% aqueous TFA, pH 2 or b/50 mM ammonium acetate, pH 6.5) over 20 min was applied at a 0.35 ml/min flow rate on a Symmetry300 C18 3.5 µm 2.1×100 mm column (Waters, Manchester, UK). LC-MS data were obtained using a Waters Alliance 2695 system comprising a 2487 dual absorbance detector and coupled with a TOF-MS detector (Waters Q-TOF Micro) with the following eluents: A: water containing 0.05 formic acid and 0.04% TFA, B: solution of acetonitrile containing 0.025% formic acid. Data acquisition and process are described bellow.

Three-Step Purification.

Solubilisation of quantitative amounts of crude peptides was achieved by mixing the lyophilised material in glacial acetic acid and rapidly diluting with water so that the final concentrations were 20 mg/ml of peptide in 20% aqueous acetic acid. This material (loading 150 mg per run) was directly purified by RP-MPLC (AP-100/200 flash, Armen Instrument, Saint Ave, France) on a preparative column (26×313 mm) packed with 100 Å 20 µm C18 Nucleoprep packing (Macherey & Nagel GmbH & Co, Düren, Germany), by applying a linear gradient (0.5%/min) of 30-60% solvent B (mixture of acetonitrile and solvent A, 8:2 v/v) in solvent A (0.08% aqueous TFA) over 60 min at a 20 ml/min flow rate. Preserving acidic environment prevent dimerisation. The purification was monitored at 214 nm (UV detector K2501, Knauer, Berlin, Germany). Suitable fractions were pooled and lyophilised. (Yield 16.2%). This material was solubilised in water by adding a small amount of aqueous ammoniac in order to raise a pH of 7.5, with 2.5 equivalents of TCEP, then subjected to a second step of purification using a linear gradient (0.4%/min) of 15-40% solvent B (mixture of acetonitrile and solvent A, 8:2 v/v) in solvent A (50 mM ammonium acetate, pH6.5) over 60 min at a 20 ml/min flow rate. In this neutral pH conditions, dimerisation occurred during the run and was led to completion before lyophilisation of the suitable fractions. (Yield 49%). The resultant dimeric peptide enriched mixture was submitted to a third step of purification by applying the first step procedure in the same acidic conditions. The retention time of the dimeric form of the target peptide was shifted about four minutes as compared to the monomeric form and the associated truncated peptides. (Yield 39%) Overall isolated unlabeled peptide yield: 2% (to be compared with 25% observed yield from HPLC analysis).

Conjugation.

Biotin and Cy5 conjugation were operated in water upon the dimeric form of the MUB peptide using the correspondent maleimide derivatives in the presence of 3 equivalents of TCEP per mole of cysteine residue. pH was adjusted to 8 with aqueous ammoniac solution. The biotinylated peptide was obtained after addition of 2 equivalents of maleimide-PEG2-biotin (Pierce, Rockford, Ill., USA). The cy5 labeling was achieved by addition of 1.2 equivalent of Cy5 Mono Maleimide (InvitroGen). Both conjugates were purified after 30 minutes of coupling reaction by RP-HPLC on a nucleosil 5 µm C18 300 Å semi-preparative column, using a linear gradient (0.75%/min) of 30-45% acetonitrile in 0.08% aqueous TFA over 20 min at a 6 ml/min flow rate. The purity was checked according the former described HPLC analytical method. The exact concentration of the purified conjugates was determined by quantitative Amino Acid Analysis; giving 69% and 20% conjugation yields for the biotinylated and the cy5-labeled products, respectively. Both constructs are resuspended in a 0.1 M Phosphate buffer pH=8, containing 0.15 M NaCl.

Electrospray Ionisation Mass Spectrometry.

Mass spectrometry was carried out on a quadrupole-TOF Micro mass spectrometer (Waters) equipped with a Z-spray API source and calibrated with a phosphoric acid calibration solution. Capillary, sample cone and extraction cone voltages were set at 3 kV, 40V and 10V, respectively. Source and desolvation temperatures were set at 80 and 250° C., respectively (raised to 120 and 400.0 in the higher flow rate conditions of LC). Data were acquired by scanning over the m/z range 150-2000 at a scan rate of 1 s and an interscan delay of 0.1 s. Lyophilised crude and purified products were dissolved in a mixture of water/methanol/acetic acid 49.5/49.5/1 v/v/v at a concentration of 1 µg/µl and analysed in positive-ion mode by infusion at a flow rate of 5 µl/min. Three hundred spectra were combined and the resultant raw multicharged spectra were processed using the MaxEnt 1 deconvolution algorithm embedded in the Masslynx software. LC/MS data were obtained by selecting and combining spectra of separate peaks and shoulders of the Total Ionic Current chromatograms. Final characterization was consistent with the expected mass: biotinylated MUB (blot-MUB$_{70}$): experimental 8755,374—expected 8755,468; Cy5-labeled MUB: experimental 9009,565—expected 9009,797.

Colon Explants Surgical Collection.

In summary, human colon explant preparation Segments of human colon (ascending, descending and sigmoid colon) were obtained from fully informed patients undergoing surgery for colon carcinoma and were analyzed anonymously. Patient written consent was obtained, according to the French bioethics law. None of the patients had undergone radiotherapy or chemotherapy. According to the pathologist's examination rules for the longitudinally bisected colon, a healthy segment of tissue which was distant from the tumour region and devoid of metastatic cells was removed. Tissues were processed according to the French Government guidelines for research on human tissues and the French Bioethics Act, with the authorization n°RBM 2009-50.

Two-Photons Microscopy.

Two-photons microscopy imaging of live healthy human colonic segment was performed using a commercial laser-scanning microscope (LSM710, Meta, Zeiss, Germany). Tissue autofluorescence and Cy5-MUB$_{70}$ (1 µg·ml$^{-1}$) were detected using multiphoton excitation (MPE, red) and collagen was detected using second harmonic generation (SHG, green). All samples were imaged immediately following tissue dissection. Illumination of samples for both MPE and SHG was accomplished using a TI: sapphire femtosecond laser (140 fs, 90 Mhz) tunable from 690 to 1040 nm (Cameleon ultra I, Coherent, inc). Excitation was performed using an output wavelength of 820 nm. Beam was focused onto samples using a ZEISS Plan-apochromat 20× objective, 1-NA water-immersion (Axial resolution are; Rxy=0.64 µm, Rz=5 µm). Both MPE and SHG were collected in a back-scattering geometry using the nondescanned detection. Detection bandwidth of MPE and SHG signals were respectively 570-610 nm (pseudocolored red) and 300-480 (pseudocolored green). Two dimensional (x,y plane) images (512×512 pixels per frame, each image was acquired in 6.71 seconds) were acquired from various depths (z increment of 3 µm). Acquisitions were performed with Zen 2008 SP 1.1 software acquisition package developed by ZEISS. Imaris software (http://www.bitplane.com) was used to prepare images.

Production of MUB70-SNAP in S2 Insect Cells

MUB70 Gene Synthetic Synthesis.

The synthesis of the gene corresponding to MUB70 was performed by Genecust. This sequence include the EcorV/SmaI restriction sites. The gene sequence is:

(SEQ ID NO: 66)
tcgcgaggatccggt<u>gatatc</u>gttcacgttcaatacattgatggtgaaac tgaccagatgctgcgtcaggatgatttggacggctacacggatgaaacga ttccttacagcacggctgaaggcatcaagaagtttgaaggcgacggttat gaactgttcaaggacaacttcccagctggtgagaagttcgataacgatga caccaacgatcaattctacacggtaatcttcaagcaccatcgtgg<u>cccgg</u>

<u>g</u>agggcccaagctt

MUB70 Gene Cloning into pDeSNAPUniv Shuttle Vector

The MUB70 DNA fragment and the pDeSNAPUniv shuttle vector (described in patent application WO2012/076715) were digested using the XmaI and EcorV desphosphorylated restriction enzymes prior cloning into E. coli DH5alpha host bacteria. The resulting sequenced construct was further digested using the BgIII and AgeI restriction enzyme for a subsequent cloning in the pMT/BIP/V5-HisA plasmid digested with the same enzymes. The resulting construct was transformed in SURE2 bacteria (Stratagene) and left 5 days at room temperature. Transformed bacteria were grown in LB medium in the presence of Ampicillin (100 ∣ g/mL) at 28° C.

S2 Insect Cell Transformation

S2 insect cells (Drosophila) were co-transfected by the resulting pMT/BIP/SnapUniv-MUB70 plasmid and pCO-Blast (encoding for a Blasticidine resistance gene) using a Qiagen Effectène kit. A stable cell line was further obtained by a series of successive passages (at least 7, twice a week) in the presence of 10 ∟ g/mL Blasticidine. As a production control test, 5 µM of Cadium chloride was added for 10 days in the S2 cell culture medium. The presence of MUB70-SNAP in the supernatant was analysed by Western blot using an anti-SNAP antibody.

MUB70-SNAP Production in S2 Cells

The transfect S2 cells were grown in a Insect Xpress liquid media (1 L) containing 10 ∟ g/mL Blasticidine. When the culture reached 9. 106 cells/mL The protein production induction was activated by the addition of 5 µM CdCl2 for 11 days. The supernatant was harvested by centrifugation (6000 rpm, 30 min) and concentrated 10 times on a Vivaflow 200 system and further dialysed in PBS containing 0.5 M NaCl and 5 mM Imidazole. The first affinity purification step was performed on a Talon beads. The elution step was performed in the presence of 200 mM Imadazole. The second purification step was performed by gel filtration on a HiLoad 16/60 Superdex 75 column (GE Healthcare) equilibrated with a 20 mM Tris pH 8 buffer containing 200 mM NaCl. The flowrate was 1 mL/min. A series of two successive runs were performed allowing a purity >95% to be reach

B. Results and Discussion

Identification of MUB$_{70}$ in *L. reuteri* AF120104 Protein Sequence.

MUB$_{70}$ was initially identified in Mucin Binding Proteins (MucBP), associated with the well-characterized Mucin Binding Domains (MucBD, PFAM 06458). However, this domain was described as being present in some but not all proteins of this family [26], reflecting the diversity of MucBP sequences and sizes (FIG. 1A). Shorter MucBP do not contain MUB$_{70}$ (i.e. *L. plantarum* Ip-1229 sequence [30], (FIG. 1A). The MUB$_{70}$ sequence could not be associated with a PFAM known homologous domain, thus its function remained unknown [26]. The sequence was named MUB$_{70}$ as its minimum conserved sequence among *Lactobacillus* strains is 70 amino acids. MUB$_{70}$ has been observed to be repeated from 1 to 18 times in different *L. reuteri* cell-surface proteins [26]. In *L. Reuteri* AF120104 cell-surface precursor protein, MUB$_{70}$ homologous sequences are repeated 13 times (SEQ ID NO: 4 to SEQ ID NO: 15), as described by Roos and co-workers [25] (FIG. 1B). Sequence comparison was performed between these sequences showing that repeats #7 and #9 are identical and are the most conserved sequences among others (Table 1). MUB$_{70}$ repeat #7 sequence possesses 23% identity with AF120104 homologous proteins MUB$_{70}$ domains in other *lactobacillus* strains (*L. gasseri, L. johnsonii, L. fermentum* and *L. delbrueckii*) (FIG. 10). This peptide (MUB$_{70}$ repeat #7) was selected as a model for chemical synthesis.

Synthesis of Cy5-MUB$_{70}$ and Biot-MUB$_{70}$.

Despite considerable evolution in the field, straight chemical synthesis of long peptide chains remains a difficult task. Considering Solid Phase Peptide Synthesis, initiated by Merrifield [31], most of the deprotection and coupling difficulties are related to inter or intra-molecular hydrogen bonds occurring over the synthesis. N-alkylated amino-acids such as Dmb/Hmb [32] or pseudoproline [33] have been more recently developed to overcome the aggregation propensity of the protected peptide chain anchored on the resin. Here, the presence of hydroxyl amino acids into MUB$_{70}$ sequence has provided the opportunity to introduce several properly spaced pseudoproline dipeptides. A single cystein was incorporated at the N-terminus to allow N-terminal specific labeling (FIG. 5). Using a classical Fmoc/tBu methodology (Strategy 2, FIG. 5) [34], a first synthesis at a 100 μmolar scale was achieved, from a polystyrene-based resin. The peptide-resin was processed with a TFA cleavage solution and the resulting crude product (weight yield 66%) was analyzed by HPLC and LC-MS in acid conditions. A 0.5%/min gradient of acetonitrile in acidic buffer was applied on a RP C18 Symmetry column (Waters) and the low pH of the injected sample therefore preserved to prevent oxidation of the cystein residue. In these conditions, the target peptide was detected as a major peak (around 8% by area integration) in a quite complex chromatogram (FIG. 6). Moreover, MS analysis of this major peak revealed the presence of a complex mixture of similar peptides with a mass deviation of −18 or +67, reflecting the presence of aspartimide and piperidine by-products in a mostly significant amount. Aspartimide formation [35] and subsequent base-catalyzed ring-opening during Fmoc-SPPS has been described to be strongly dependent of the previous coupled amino-acid [36] in relation with the global mixing time of the Asp-containing peptide resin in the FMOC deprotection solution [37]. Indeed MUB$_{70}$ sequence accumulates eight highly sensitive occurrences (3 Asp-Gly, 2 Asp-Asn, 2 Asp-Asp, 1 Asp-Thr), among which Asp-Gly sequences are particularly prone to aspartimide formation. A systematic protection of each glycine amide moiety occurring before an Asp derivative coupling was achieved by coupling Fmoc-Asp(OtBu)-(Dmb) Gly-OH dipeptides (Strategy 2, FIG. 5), namely in position 29, 50 and 63 in reference to the C-terminus [38]. As a result the disaggregation of the peptide chain was improved and accordingly the deprotection and coupling efficiency (FIG. 5I). The resulting resin was processed and the crude was analyzed by LC-MS according to the same protocol. Although the weight yields calculated from the crude products were similar (65%) the target peptide peak area integration was increased from 8% to 25% (FIG. S2B).

Figure 6A:
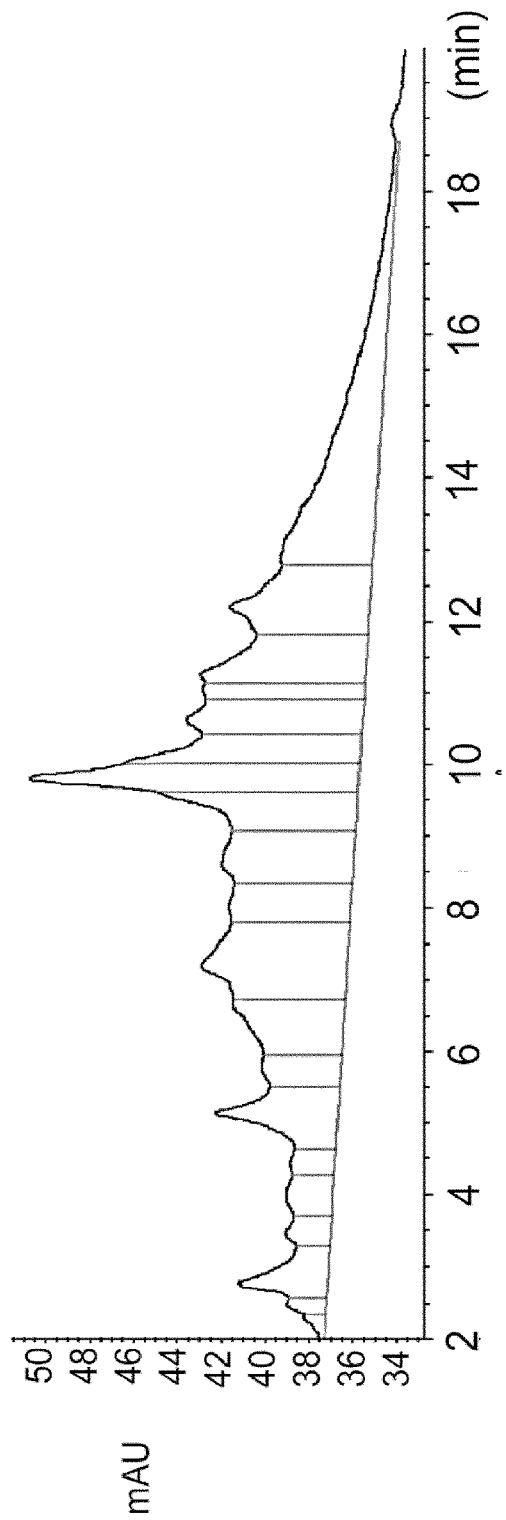
Figure 6B:
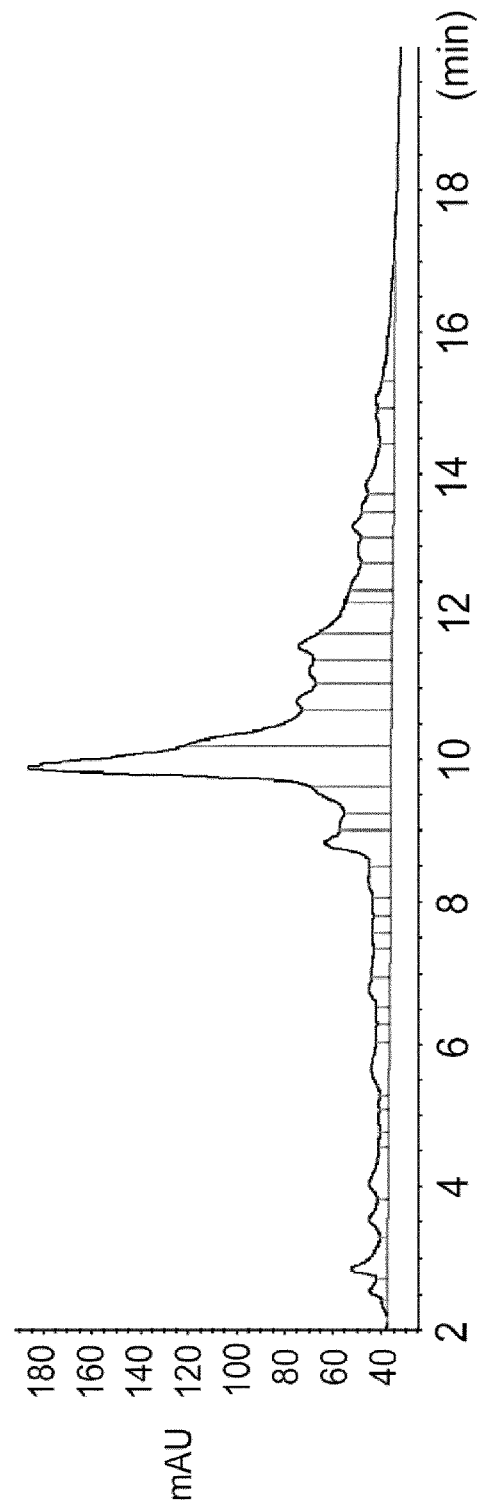
Figure 6C:
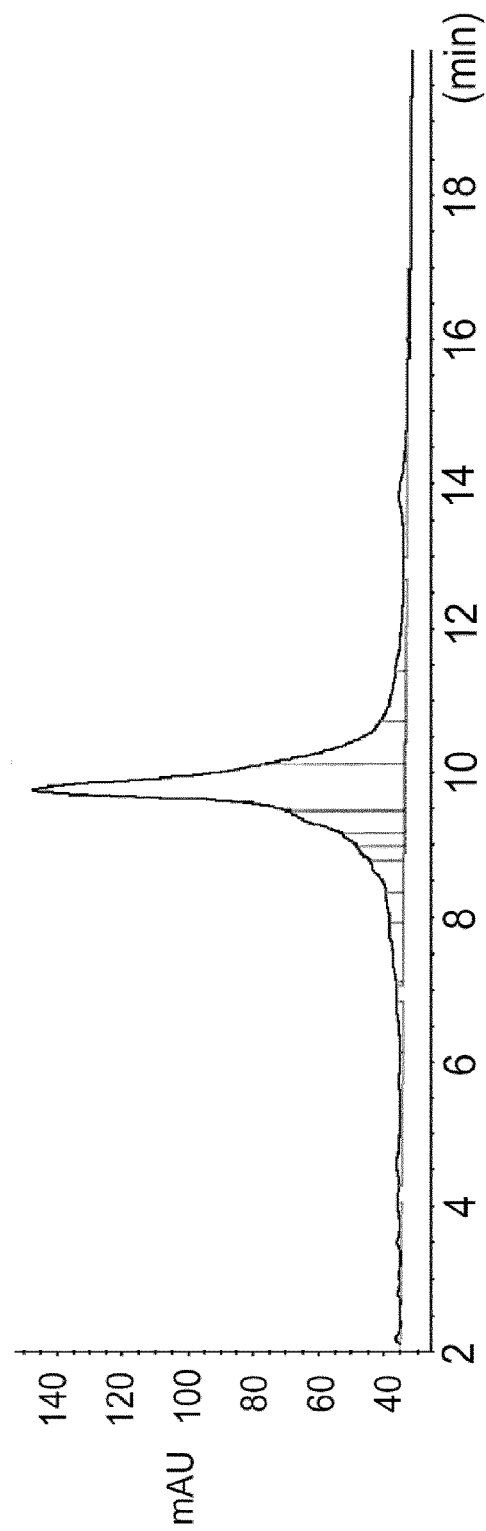
Figure 6D:
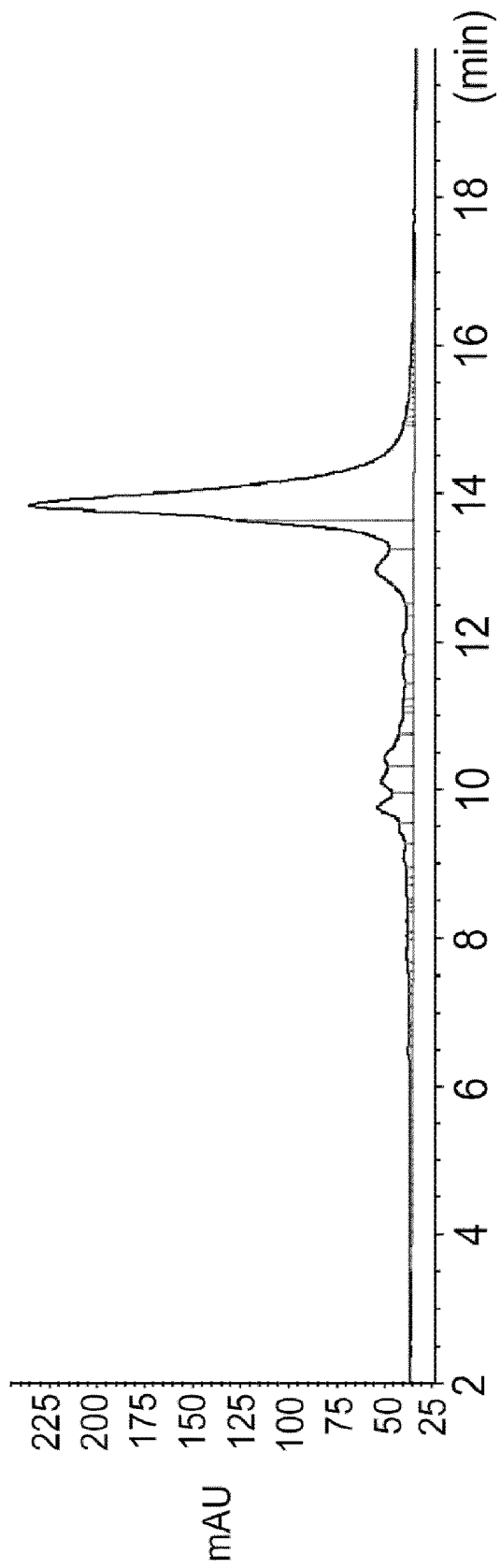
Figure 6E:
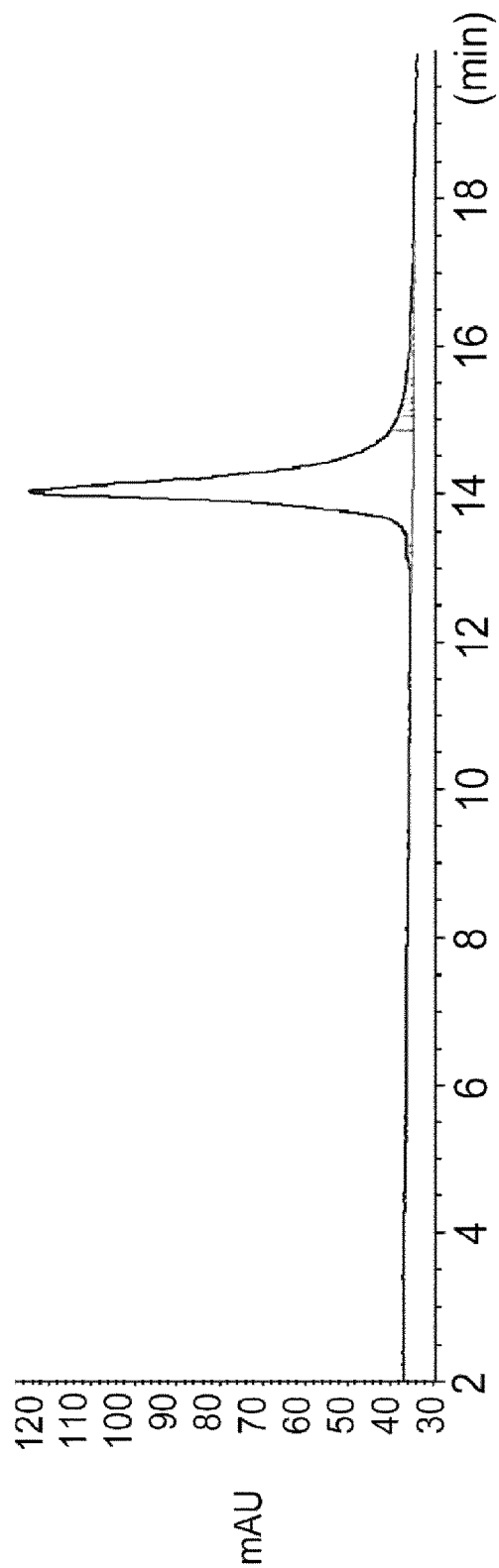

A first RP-MPLC purification protocol was applied in acidic environment (pH=2) in order to maintain the peptide in its reduced form. The remaining aspartimide and piperidine side products (FIG. 6C) were shown to be well separated when analyzed by RP-HPLC in neutral conditions, using 50 mM ammonium acetate (pH6.5) as aqueous buffer (data not shown). Despite the presence of 2.5 equivalents of TCEP as reductive agent into the loaded mixture, scaling up this protocol through a second RP-MPLC purification step revealed the high propensity of this material to dimerize in acetonitrile containing solution. Moreover, oxidation of the sulfhydryl moiety occurred along the run and was led to completion before lyophilization. RP analysis at pH=2 of the resulting partially purified material showed a significant shift between both dimer and monomer-associated truncated peptides retention times (FIG. 6D). Consequently a last RP-MPLC purification step was achieved by repeating the former protocol to yield the MUB dimeric form with above 90% purity (FIG. 2A).

To summarize, improvement of the synthesis by the incorporation of Dmb and pseudoproline dipeptides, followed by a three steps purification process were combined to isolate the target peptide (FIG. 6E) as covalent dimer with an overall weight yield of 2%. Monomer recovery and simultaneous conjugation of biotin or fluorophore via the maleimide derivatives are described in Methods.

Biochemical Properties of MUB$_{70}$.

Figure 7A:
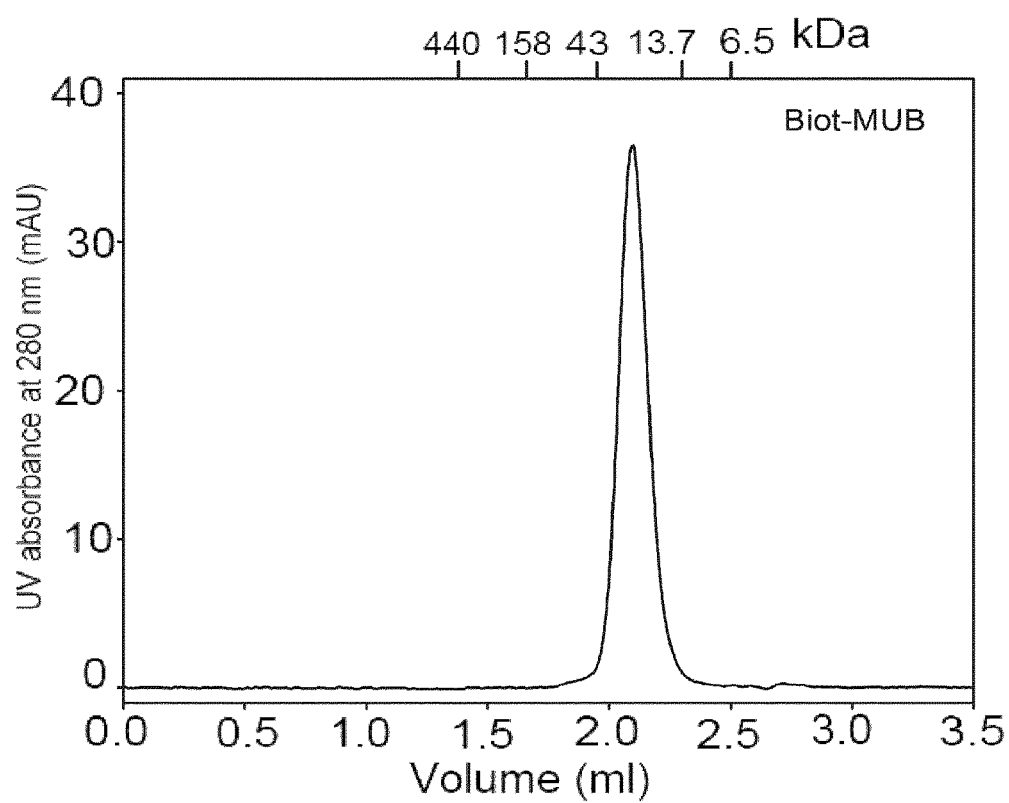
Figure 7B:
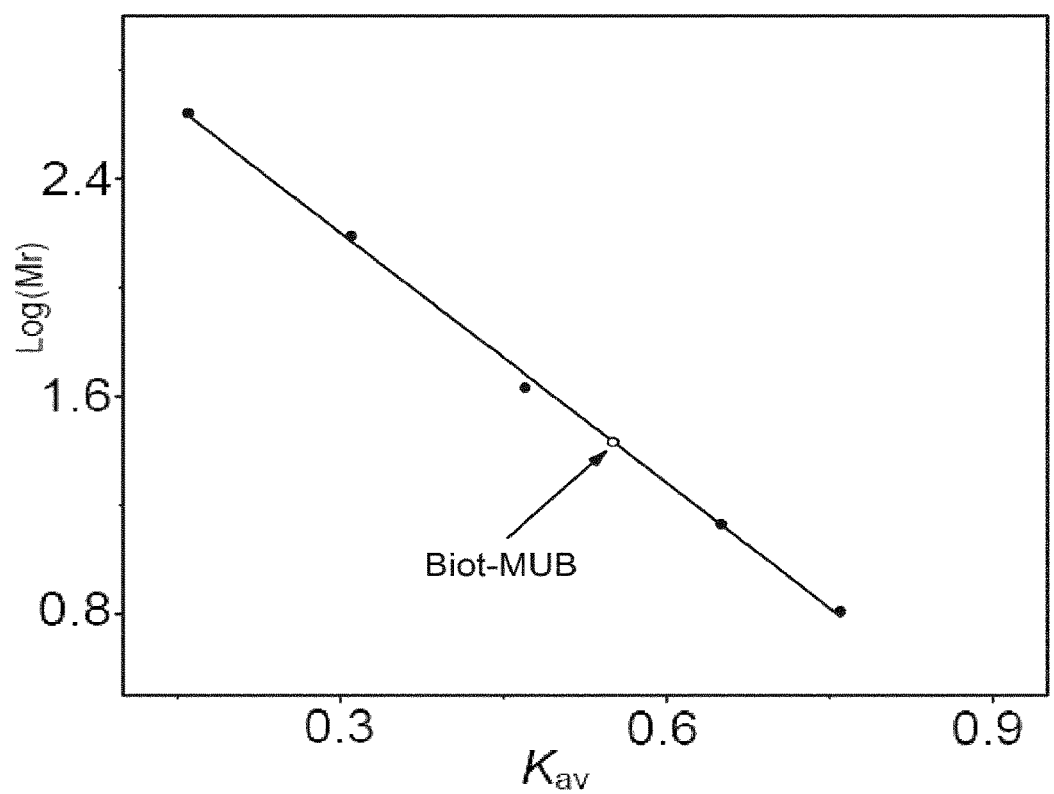
Figure 7C:
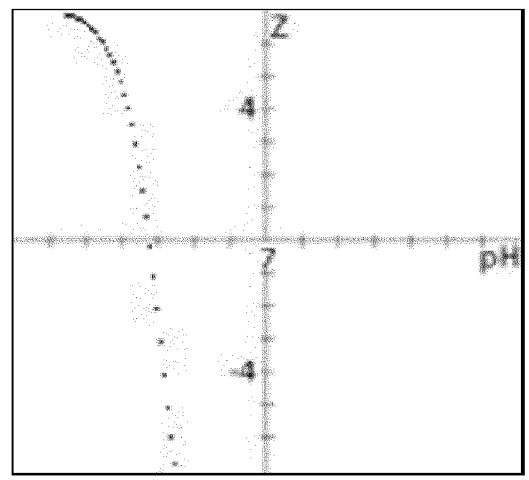
Figure 7D:
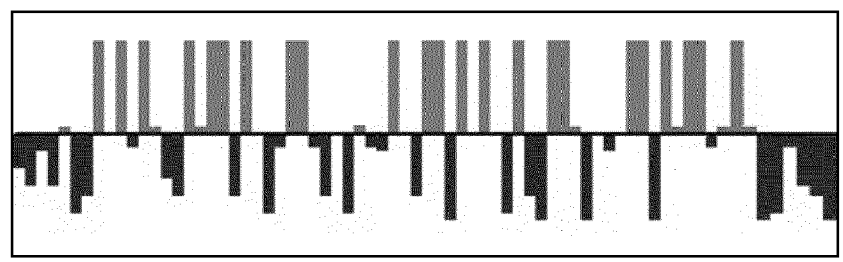

MUB$_{70}$ is predicted to be a negatively charged peptide at a pH higher than 4 (net charge at pH=7 is −12.9), (FIG. 7C) even though the surface charge of MUB$_{70}$ is still unknown. No specific hydrophobic domain was predicted through a Kyte-Doolittle analysis of MUB$_{70}$ (FIG. 7D). This result is consistent with its high solubility in a phosphate buffer at pH=8 (see Methods). The theoretical molecular weight (MW) of a biotinylated MUB$_{70}$ (biot-MUB$_{70}$) is 8.8 kDa. However when migrating on a SDS-PAGE gel, the apparent MW is around 28 kDa and this result is independent from the pH, which seems to indicate a stable oligomerization of biot-MUB$_{70}$ (FIG. 2B). This observation was confirmed with the fluorescent Cy5-MUB$_{70}$ compound (data not shown). In order to confirm the predicted trimeric organization of MUB$_{70}$, an analytical gel filtration was performed on biot-MUB$_{70}$ in order to determine its quaternary structure. The elution profile was recorded at 280 nm. At 0.1 and 1 mg/ml, biot-MUB$_{70}$ gave a single peak at an elution volume of 2.1 ml (FIG. 2C and FIGS. 7A and 7B). The molecular mass was determined to be 27.9 kDa, proposing that biot-MUB$_{70}$, with a theoretical mass of 8.8 kDa, exists as trimer in phosphate buffer.

Cell Toxicity of MUB$_{70}$.

Figure 8A:
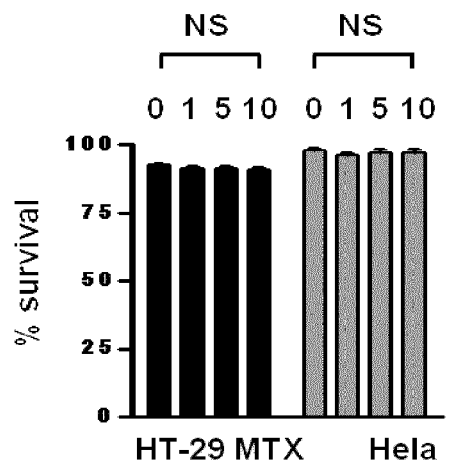

As Cy5-MUB$_{70}$ was envisaged to be used on living cells and organs, its cell-toxicity has been evaluated. This probe was incubated on differentiated HT-29 MTX and on Hela cells as cell viability was assessed using a Sytox Green assay (see Methods). Incubating MUB$_{70}$ (1 μg/mL) for up to 10 h in a serum starved media do not affect significantly cell viability (Student test, NS, p>0.05, n=3) (FIG. 8A). This result was consistent with the hydrophilic property of $MUB_{70}$ (FIG. 7D) which does not allow cell penetration. The absence of intracellular fluorescent signal upon exposure of different living cell types (phagocytic and non-phagocytic cells) exposed to Cy5-$MUB_{70}$ (1 µg/mL in a serum free media) (i.e. human epithelial cells, human myeloid cells, human ES cells, mouse dendritic cells, data not shown) was also confirmed.

Specific Staining of Human, Rabbit and Guinea Pig Colonic Mucus Using Cy5-$MUB_{70}$.

Figure 8B:
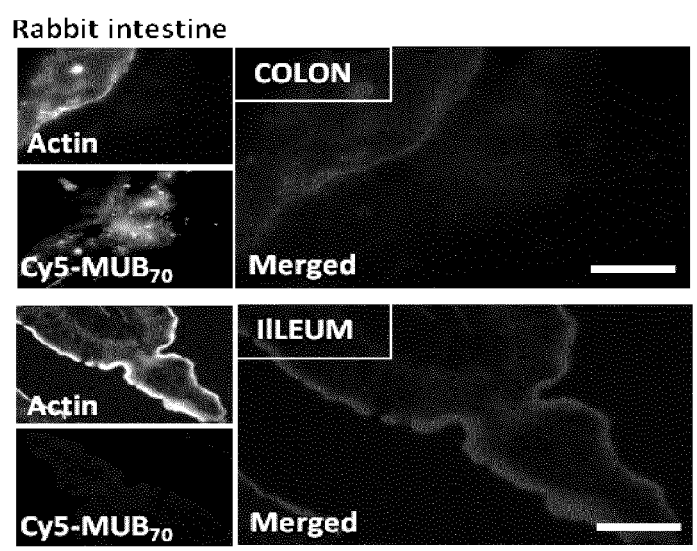
Figure 8C:
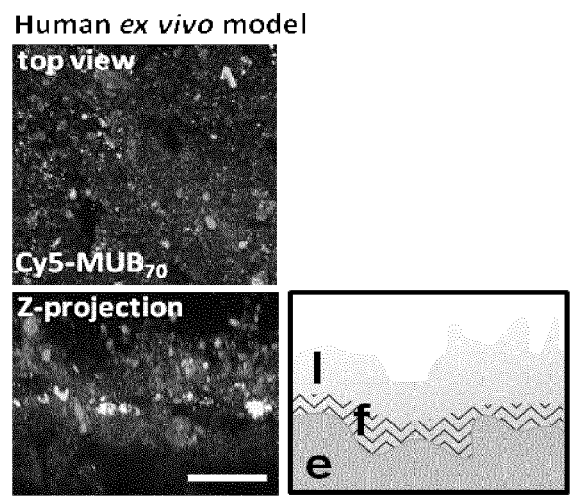

Cy5-$MUB_{70}$ was incubated on living differentiated HT-29 MTX human epithelial colonic cells, which have the property to constitutively produce a mucus layer after differentiation (see Methods). As observed using a live epifluorescent microscope, Cy5-$MUB_{70}$ was binding the mucus layer at the surface of the cells. A Z-projection observation allowed the visualization of fluorescent mucus patches, typical of mucus aggregates produced by differentiated HT-29 MTX cells [28], as cells remained unstained (FIG. 3A). This result demonstrates that $MUB_{70}$ is a new Mucus Binding Domain (MUcBD). This observation was confirmed by incubating Cy5-$MUB_{70}$ on human colon explants. As shown in FIG. 3B, the mucus layer, observed using a two-photons microscope, is stained heterogeneously on the whole width (estimated around 1000 µm) as the epithelium and lamina propria remain unstained. Proportion of mucus stained by Cy5-$MUB_{70}$ might depend on Cy5-$MUB_{70}$ concentration and on the thickness of the mucus layer, as thinner layers could be stained until epithelium surface (FIG. 8C). Staining kinetic analysis indicates that Cy5-$MUB_{70}$ is widely detected after 90 min onto a 1 mm thick mucus layer (FIG. 4D).

Figure 8D:
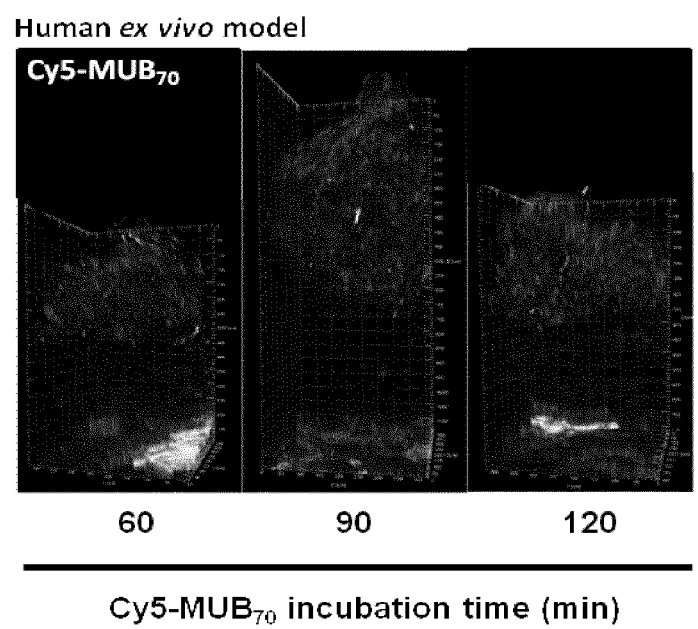

Different animal models were used to confirm this result: rabbit, guinea pig and mouse colon were tested. Interestingly colonic mucus staining using Cy5-$MUB_{70}$ was confirmed on rabbit and guinea pig models (FIG. 11A and FIG. 11B). However, mouse colonic mucus was not stained applying the same procedure (FIG. 11C), which indicates major differences in its composition compared to human. The specific colonic mucus binding property of Cy5-$MUB_{70}$ was confirmed on the rabbit model, as negative results were obtained on ileal mucus samples (FIG. 8D). These results rule out the possibility of a specific trapping of Cy5-$MUB_{70}$ in mucus layers and as a control, Cy5 fluorophore does not have the property to bind human mucus (FIG. 10A). As a conclusion, these results suggest that Cy5-$MUB_{70}$ interacts with a colonic mucus secreted specific component present in human, rabbit and guinea pig but not in mouse.

Biot-$MUB_{70}$ Binds Specifically to Glycosylated Muc2 from Colonic Mucus.

In order to identify a $MUB_{70}$ ligand present in the soluble extracts of human colonic mucus, biot-$MUB_{70}$, a biotinylated form of $MUB_{70}$, was synthesized (see Methods) in order to perform pulldown assays. Biot-$MUB_{70}$ was incubated with avidin beads and further with human colonic mucus extracts (produced in vitro from differentiated HT-29 MTX cells, see Methods). Biotin only was used as a negative control. Following initial attempts aimed at separating eluted proteins on SDS-page gel, Coomassie staining did not allow the identification of any specific protein (data not shown). A dot blot assay was then performed, focusing on secreted mucins, which are the major components of colonic mucus. Muc2 was immunodectected in the eluted fraction, and not in the negative control, and Muc5ac, Muc5b or Muc6, all detected in the input were absent from the eluted fraction (FIG. 4A). This result was confirmed by immunofluorescence colocalization detection of Muc2 and Cy5-$MUB_{70}$ on human colon mucus purified from ex vivo samples (FIG. 4B) and fixed purified human mucus and rabbit colon samples (FIGS. 9A and 9B). Processing a chemical deglycosylation step on the soluble mucus extract (see Methods) prior to pulldown assay abolished the interaction between Muc2 and biot-$MUB_{70}$ (FIG. 4A). It was specifically demonstrated that desulfatation (glycosylsulfatase) but not desialylation (neuramidase) lead to a loss of this interaction (FIG. 4A), highlighting the role of sulfate groups found specifically on human colonic mucus [12] in the binding of $MUB_{70}$. This result could explain the differential staining observed on rabbit ileal and colonic mucus (see above and FIG. 8B) as Muc2—expressed and secreted in both organs—possesses differential glycosylation patterns [9] [12]. As a conclusion, $MUB_{70}$ binds sulfated Muc2 oligosaccharides in colonic mucus thus exploiting its specific glycosylation profile. As a control, considering that Muc2 has been recently shown to bind covalently Fcα-binding-protein (FCGBP) [39], the role of this partner of Muc2 in the association with $MUB_{70}$ was analyzed. As FCGBP binds a specifically to the biotin-conjugated avidin beads moiety (FIG. 10B), it was not possible to directly exclude a role of this protein in the Muc2/$MUB_{70}$ interaction. However, indirectly, after deglycosylation, as an abolishment of the Muc2/$MUB_{70}$ interaction was observed (see above, FIG. 4A) it was not the case of FCGBP binding to biotin (FIG. 8B). In addition, the colon-versus-ileum specificity of mucus $MUB_{70}$ binding observed in rabbit samples (FIG. 8B) excludes any role of FCGBP. These results suggest no specific role of FCGBP in the Muc2/$MUB_{70}$ interaction.

Cy5-MUB70 is a New Specific Marker for Colonic Mucinous Carcinomas.

As colonic mucinous carcinomas are characterized by abnormal overproduction of Muc2 in the colon mucosa (40), the inventors have hypothesized that Cy5-MUB70 could be used as a novel fluorescent marker for the diagnosis of this pathology. They have demonstrated, on five different samples collected from patients diagnosed with colonic mucinous carcinomas, that a specific staining was observed within the mucus accumulation areas (a representative sample is shown in FIG. 24B). As shown previously on a healthy colon (FIG. 3B), the luminal mucus secreted fraction is detected by Cy5-$MUB_{70}$ (FIG. 24A, top panel). As a control, no mucosal staining was observed in the colonic mucosa in healthy colon tissues originating from the same patients (FIG. 24A, lower panel). Interestingly, the inventors have shown that goblet cells are not recognized by Cy5-$MUB_{70}$. This observation might be the consequence of a higher level of mucus compaction, resulting in a lower accessibility for $MUB_{70}$ to bind Muc2. In colonic mucinous carcinomas (FIG. 24B), the fluorescent signal observed with Cy5-MUB70 (red) colocalizes with the presence of Muc2 (green) in the pathologic extensive mucus accumulation observed within the colonic mucosa and associated with tumor cells. Cy5-$MUB_{70}$ has been validated as a potent innovative diagnostic tool for colonic mucinous carcinoma detection and might be optimized with alternative markers (e.g. biotin) for practical clinical applications.

C. Conclusion

As a summary of the experiments described here-above, the synthesized *L. reuteri* MUBAD or $MUB_{70}$ is a new Mucus Binding Domain (MUcBD) which possesses oligomerisation properties which might contribute to the anchoring of these commensal bacteria in the colonic mucus layer. Chemically synthesized $MUB_{70}$ is a novel specific colonic mucus marker interacting with the sulfated moiety of Muc2 oligosaccharides, known as the main component of this epithelium surface protective layer. $MUB_{70}$ trimerisation property is believed to contribute to its interaction with Muc2 found in human, rabbit and guinea pig colonic mucus, not in mouse model. Conjugating $MUB_{70}$ with a fluorescent dye (i.e. Cy5) enables the provision of a new generation physiological probe allowing direct observation of colonic mucus in ex vivo and in vivo live imaging approaches, beyond classical immunofluorescence techniques. Furthermore, as mucins (including Muc2) expression and glycosylation modifications are frequently observed in mucinous carcinomas and IBD, targeting Muc2 with $MUB_{70}$ provides promising innovative approaches to develop new diagnostic tools.

The inventors have further synthesized shorter probes identified as $MUB_{40}$ probes herein, displaying the same properties than the $MUB_{70}$ probe. In particular, the $MUB_{40}$-Cy5#1 probe has proven to be a functional human mucus-binding peptide, additionally possessing globlet-cells binding properties in comparison with $MUB_{70}$-Cy5. This development exemplifies the pertinence of small probes encompassing the sequence(s) disclosed herein for the purpose of the invention.

The invention provides a solution for imaging living cells and organs, which requires innovative specific, efficient and well-tolerated fluorescent probes targeting cellular components and provides tools allowing to perform dynamic analysis of cell(s) and tissue(s) adaptation to environmental cues.

According to a particular embodiment of the invention, a novel non-toxic fluorescent marker of 70 amino acid peptide of unknown function frequently associated to MUB domains, named $MUB_{70}$, allowing specific fluorescent staining of human colonic mucus was identified, characterized and synthesized. In humans, the colonic mucus layer is on the average 500 µm thick and composed of different secreted gel-forming mucins (Muc2, Muc5ac, Muc5b, Muc6). Fluorescent peptide markers of 40 amino acids, named $MUB_{40}$ were also identified, characterized and synthesized. Muc2 is the most abundant secreted mucin forming the backbone of this cell surface protective layer. The synthesized peptide is highly conserved among *Lactobacillus* strains. Its chemical synthesis was achieved using the human commensal bacterium *L. reuteri* AF120104 protein as a template.

The synthesized Cy5-$MUB_{70}$ conjugated probe specifically stained colonic mucus, on fixed human, rabbit and guinea pig tissues, but not on murine tissues, indicating that the later shows significant difference in the composition of its colonic mucus. It was also shown that this probe also stained the mucus produced by cultured human colonic cells (HT29-MTX) and by human colonic tissue explants. As demonstrated using a biotinylated derivative of $MUB_{70}$, this peptide specifically binds to the glycoprotein Muc2, through its glycosylated moiety.

Hence Cy5-$MUB_{70}$ and Cy5-$MUB_{40}$ series are novel, specific fluorescent markers for mammalian colonic mucus that can be used for live imaging analysis and as marker for diagnostic and prognosis of mucinous carcinomas and IBD.

The chemical synthesis of fluorescent conjugated Cy5-$MUB_{70}$ and Cy5-$MUB_{40}$ series markers allowed the construction of a new generation of specific markers of mucus, especially colonic mucus, in particular carcinoma(s) colonic mucus, that might be used as a probes for live experimental imaging of the colon. In addition, further developments are anticipated in IBD and mucinous carcinomas to envision more accurate diagnostic and prognostic tools.

The inventors have shown, interestingly, that MUB70 is not toxic for living cells as it has no cell penetration property, allowing its specific localization in the mucus layer located on the epithelium surface. They also have proven the efficiency of the probes of the invention for investigating the colonic mucinous carcinoma. Muc2 expression is up-regulated in mucinous carcinomas affecting various organs, including the lung, the stomach, the breast, the prostate, and the bile ducts. Hence, targeting Muc2 with $MUB_{70}$, as observed on human colonic mucinous carcinomas, is anticipated to provide promising innovative approaches to develop new prognosis and diagnostic tools on various mucinous carcinomas.

The invention has also proven to be useful for the monitoring of neutrophile degranulation events, in particular by using $MUB_{70}$ and/or $MUB_{40}$ polypeptides or polypeptides sharing identity with $MUB_{70}$ and/or $MUB_{40}$ polypeptides, or fragments thereof, for labelling neutrophile granule(s). As illustrated in FIG. 31, the inventors have demonstrated the efficiency of all synthesized $MUB_{70}$ and $MUB_{40}$ polypeptides to this end: in the experiment corresponding to FIG. 31, and although a brighter signal was obtained with Cy5-MUB40-1 and Cy5-MUB40-4 probes, PMN granules were found to be efficiently stained on fixed cells with Cy5-MUB40-1, Cy5-MUB40-2, Cy5-MUB40-3 Cy5-MUB40-4, as compared to staining obtained with Cy5-MUB70.

BIBLIOGRAPHY

1. Bergstrom, K. S., et al., *Muc2 protects against lethal infectious colitis by disassociating pathogenic and commensal bacteria from the colonic mucosa*. PLoS Pathog. 6(5): p. e1000902.
2. Rubinstein, A. and B. Tirosh, *Mucus gel thickness and turnover in the gastrointestinal tract of the rat: response to cholinergic stimulus and implication for mucoadhesion*. Pharm Res, 1994. 11(6): p. 794-9.
3. Marteyn, B., et al., *Modulation of Shigella virulence in response to available oxygen in vivo*. Nature, 2010. 465 (7296): p. 355-8.
4. Marteyn, B., et al., *Breathing life into pathogens: the influence of oxygen on bacterial virulence and host responses in the gastrointestinal tract*. Cell Microbiol, 2010.
5. Johansson, M. E., J. M. Larsson, and G. C. Hansson, *The two mucus layers of colon are organized by the MUC2 mucin, whereas the outer layer is a legislator of host-microbial interactions*. Proc Natl Acad Sci USA. 108 Suppl 1: p. 4659-65.
6. Wong, W. M., R. Poulsom, and N. A. Wright, *Trefoil peptides*. Gut, 1999. 44(6): p. 890-5.
7. Lesuffleur, T., A. Zweibaum, and F. X. Real, *Mucins in normal and neoplastic human gastrointestinal tissues*. Crit Rev Oncol Hematol, 1994. 17(3): p. 153-80.
8. Tytgat, K. M., et al., *Biosynthesis of human colonic mucin: Muc2 is the prominent secretory mucin*. Gastroenterology, 1994. 107(5): p. 1352-63.
9. Karlsson, N. G., et al., *Molecular characterization of the large heavily glycosylated domain glycopeptide from the rat small intestinal Muc2 mucin*. Glycoconj J, 1996. 13(5): p. 823-31.
10. Allen, A., D. A. Hutton, and J. P. Pearson, *The MUC2 gene product: a human intestinal mucin*. Int J Biochem Cell Biol, 1998. 30(7): p. 797-801.

11. van Klinken, B. J., et al., *Gastrointestinal expression and partial cDNA cloning of murine Muc2*. Am J Physiol, 1999. 276(1 Pt 1): p. G115-24.
12. Robbe, C., et al., *Evidence of regio-specific glycosylation in human intestinal mucins: presence of an acidic gradient along the intestinal tract*. J Biol Chem, 2003. 278(47): p. 46337-48.
13. Schultsz, C., et al., *The intestinal mucus layer from patients with inflammatory bowel disease harbors high numbers of bacteria compared with controls*. Gastroenterology, 1999. 117(5): p. 1089-97.
14. Shaoul, R., et al., *Colonic expression of MUC2, MUC5AC, and TFF1 in inflammatory bowel disease in children*. J Pediatr Gastroenterol Nutr, 2004. 38(5): p. 488-93.
15. Faure, M., et al., *The chronic colitis developed by HLA-B27 transgenic rats is associated with altered in vivo mucin synthesis*. Dig Dis Sci, 2004. 49(2): p. 339-46.
16. Lau, S. K., L. M. Weiss, and P. G. Chu, *Differential expression of MUC1, MUC2, and MUC5AC in carcinomas of various sites: an immunohistochemical study*. Am J Clin Pathol, 2004. 122(1): p. 61-9.
17. Mesquita, P., et al., *Coordinated expression of MUC2 and CDX-2 in mucinous carcinomas of the lung can be explained by the role of CDX-2 as transcriptional regulator of MUC2*. Am J Surg Pathol, 2004. 28(9): p. 1254-5.
18. Strugala, V., P. W. Dettmar, and J. P. Pearson, *Thickness and continuity of the adherent colonic mucus barrier in active and quiescent ulcerative colitis and Crohn's disease*. Int J Clin Pract, 2008. 62(5): p. 762-9.
19. Khattab, A. Z., W. A. Nasif, and M. Lotfy, *MUC2 and MUC6 apomucins expression in human gastric neoplasm: an immunohistochemical analysis*. Med Oncol.
20. Mukhopadhyay, P., et al., *Mucins in the pathogenesis of breast cancer: implications in diagnosis, prognosis and therapy*. Biochim Biophys Acta. 1815(2): p. 224-40.
21. Zhang, S., et al., *Expression of potential target antigens for immunotherapy on primary and metastatic prostate cancers*. Clin Cancer Res, 1998. 4(2): p. 295-302.
22. Park, S. Y., et al., *Expression of MUC1, MUC2, MUC5AC and MUC6 in cholangiocarcinoma: prognostic impact*. Oncol Rep, 2009. 22(3): p. 649-57.
23. Travo, A., et al., *IR spectral imaging of secreted mucus: a promising new tool for the histopathological recognition of human colonic adenocarcinomas*. Histopathology. 56(7): p. 921-31.
24. Ouwehand, A. C., et al., *Assessment of adhesion properties of novel probiotic strains to human intestinal mucus*. Int J Food Microbiol, 2001. 64(1-2): p. 119-26.
25. Roos, S. and H. Jonsson, *A high-molecular-mass cell-surface protein from Lactobacillus reuteri 1063 adheres to mucus components*. Microbiology, 2002. 148 (Pt 2): p. 433-42.
26. Boekhorst, J., et al., *Comparative analysis of proteins with a mucus-binding domain found exclusively in lactic acid bacteria*. Microbiology, 2006. 152 (Pt 1): p. 273-80.
27. Bansal, D., et al., *An ex-vivo human intestinal model to study Entamoeba histolytica pathogenesis*. PLoS Negl Trop Dis, 2009. 3(11): p. e551.
28.
29. Huet, G., et al., *Characterization of mucins and proteoglycans synthesized by a mucin-secreting HT-29 cell subpopulation*. J Cell Sci, 1995. 108 (Pt 3): p. 1275-85.
30. Pretzer, G., et al., *Biodiversity-based identification and functional characterization of the mannose-specific adhesin of Lactobacillus plantarum*. J Bacteriol, 2005. 187(17): p. 6128-36.
31. Merrifield, R. B., *Solid Phase Peptide Synthesis. I. The Synthesis of a Tetrapeptide*. Journal of the American Chemical Society, 1963. 85(14): p. 2149-2154.
32. Johnson, T., M. Quibell, and R. C. Sheppard, *N,O-bisFmoc derivatives of N-(2-hydroxy-4-methoxybenzyl)-amino acids: useful intermediates in peptide synthesis*. J Pept Sci, 1995. 1(1): p. 11-25.
33. Wohr, T., *Pseudo-prolines as a solubilizing, structure-disrupting protection technique in peptide synthesis*. Journal of the American Chemical Society, 1996. 118(39): p. 9218-9227.
34. Chan, C. C. a. P. D. W., *Fmoc Solid Phase Peptide Synthesis. A Practical Approach*. Oxford University Press, Oxford., 2000.
35. Mergler, M., et al., *The aspartimide problem in Fmoc-based SPPS. Part I*. J Pept Sci, 2003. 9(1): p. 36-46.
36. Lauer, J. L., C. G. Fields, and G. B. Fields, *Sequence dependence of aspartimide formation during 9-fluorenylmethoxycarbonyl solid-phase peptide synthesis*. Letters in Peptide Science, 1995. 1: p. 197-205.
37. Quibell, M., et al., *Suppression of piperidine-mediated side product formation for Asp(Obu(T))-containing peptides by the use of N-(2-Hydroxy-4-Methoxybenzyl) (Hmb) backbone amide protection*. Journal of the Chemical Society-Chemical Communications, 1994. 20: p. 2343-2344.
38. Cardona, V., et al., *Application of Dmb-Dipeptides in the Fmoc SPPS of Difficult and Aspartimide-Prone Sequences*. International Journal of Peptide Research and Therapeutics, 2008. 14(4): p. 285-292.
39. Johansson, M. E., K. A. Thomsson, and G. C. Hansson, *Proteomic analyses of the two mucus layers of the colon barrier reveal that their main component, the Muc2 mucin, is strongly bound to the Fcgbp protein*. J Proteome Res, 2009. 8(7): p. 3549-57.
40. Travo, A., Piot, O., Wolthuis, R., Gobinet, C., Manfait, M., Bara, J., Forgue-Lafitte, M. E., and Jeannesson, P. (2010) IR spectral imaging of secreted mucus. A promising new tool for histopathological recognition of human colonic adenocarcinomas. *Histopathology* 56, 921-931
41. Coïo Yves-Marie, Baleux Françoise, Poyraz Ömer, Thibeaux Roman, Labruyere Elisabeth, Chretien Fabrice, Sobhani Iradj, Lazure Thierry, Wyplosz Benjamin, Schneider Gunter, Mulard Laurence, Sansonetti Philippe J., Marteyn Benoit S., (2012) Design of a specific colonic mucus marker using a human commensal bacterium cell surface domain, *The Journal of Biological Chemistry* 287 (19) 15916-15922

The invention claimed is:

1. An isolated nucleic acid molecule that comprises an open reading frame that encodes a polypeptide consisting of:
   a) SEQ ID NO: 3 having an additional cysteine residue at the N-terminus,
   b) a fragment of SEQ ID NO: 3, wherein the fragment has an additional cysteine residue at the N-terminus, and wherein the fragment has a length of at least 20 contiguous amino acid residues,
   c) a variant of SEQ ID NO: 3, wherein the variant has an additional cysteine residue at the N-terminus and has at least 85% identity with SEQ ID NO: 3, or
   d) a variant of a fragment of SEQ ID NO: 3, wherein the variant of the fragment has an additional cysteine residue at the N-terminus, has a length of at least 20 contiguous amino acid residues, and has at least 85% identity with the fragment of SEQ ID NO: 3.

2. The isolated nucleic acid molecule according to claim 1, wherein the polypeptide consists of:
   a) SEQ ID NO: 58 having an additional cysteine residue at the N-terminus,
   b) SEQ ID NO: 59 having an additional cysteine residue at the N-terminus,
   c) SEQ ID NO: 60 having an additional cysteine residue at the N-terminus,
   d) SEQ ID NO: 61 having an additional cysteine residue at the N-terminus,
   e) a sequence having at least 85% identity with SEQ ID NO: 58 and having an additional cysteine residue at the N-terminus,
   f) a sequence having at least 85% identity with SEQ ID NO: 59 and having an additional cysteine residue at the N-terminus,
   g) a sequence having at least 85% identity with SEQ ID NO: 60 and having an additional cysteine residue at the N-terminus, or
   h) a sequence having at least 85% identity with SEQ ID NO: 61 and having an additional cysteine residue at the N-terminus.

3. The isolated nucleic acid molecule according to claim 1, wherein the nucleic acid molecule comprises a variant of SEQ ID NO: 66.

4. A recombinant vector comprising a nucleic acid molecule that comprises an open reading frame that encodes a polypeptide consisting of:
   a) SEQ ID NO:3,
   b) a fragment of SEQ ID NO: 3 having a length of at least 20 contiguous amino acid residues,
   c) a variant of SEQ ID NO: 3 having at least 85% identity with SEQ ID NO: 3, or
   d) a variant of a fragment of SEQ ID NO: 3 having a length of at least 20 contiguous amino acid residues and having at least 85% identity with the fragment.

5. The vector according to claim 4, wherein the vector is a plasmid.

6. The vector according to claim 4, wherein the vector is a 6-methylguanine-DNA-methyltransferase enzyme (MGMT)-based vector.

7. A recombinant vector comprising a nucleic acid molecule encoding in a single open reading frame, from 5' to 3':
   a) a peptidic secretion signal which is functional in insect cells,
   b) a 6-methylguanine-DNA-methyltransferase enzyme or a mutant or a fragment thereof having at least 80% of catalytic activity of native 6-methylguanine-DNA-methyltransferase enzyme, and c) a polypeptide consisting of:
   i) SEQ ID NO:3,
   ii) a fragment of SEQ ID NO: 3 having a length of at least 20 contiguous amino acid residues,
   iii) a variant of SEQ ID NO: 3 having at least 85% identity with SEQ ID NO: 3, or
   iv) a variant of a fragment of SEQ ID NO: 3 having a length of at least 20 contiguous amino acid residues and having at least 85% identity with the fragment.

8. The vector according to claim 7, wherein the encoded peptidic secretion signal is functional in S2 Drosophilia insect cells.

9. A recombinant cell or a population of recombinant cells comprising a nucleic acid molecule according to claim 1.

10. A recombinant cell or population of recombinant cells comprising a vector according to claim 4.

11. The recombinant cell or population of recombinant cells according to claim 10, wherein the cells are transfected with the vector.

12. The recombinant cell or population of recombinant cells according to claim 11, wherein the cells are S2 Drosophilia insect cells.

13. A method for producing a polypeptide, comprising:
   a. transfecting a vector according to claim 4 in a cell,
   b. culturing the cell to form a cell culture containing the polypeptide, and
   c. recovering the polypeptide from the cell culture.

14. A method according to claim 13, wherein the vector is a MGMT-based vector and the cell is a S2 Drosophilia insect cell.

15. The vector according to claim 4, wherein the polypeptide consists of:
   a) a fragment of SEQ ID NO: 3 consisting of SEQ ID NO: 58, SEQ ID NO: 59, SEQ ID NO: 60, or SEQ ID NO: 61 or
   b) a sequence having at least 85% identity with SEQ ID NO: 58, SEQ ID NO: 59, SEQ ID NO: 60, or SEQ ID NO: 61.

16. The vector according to claim 4, wherein the polypeptide is a variant of SEQ ID NO: 3 having at least 85% identity with SEQ ID NO: 3, or a variant of a fragment of SEQ ID NO: 3 having a length of at least 20 contiguous amino acid residues and having at least 85% identity with the fragment, and wherein the polypeptide has an additional cysteine residue at the N-terminus.

17. The vector according to claim 4, wherein the nucleic acid molecule consists of SEQ ID NO: 66.

* * * * *

SEQUENCE LISTING

<160> NUMBER OF SEQ ID NOS: 89

<210> SEQ ID NO 1
<211> LENGTH: 60
<212> TYPE: PRT

```
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Asp or Asn
<220> FEATURE:
<221> NAME/KEY: MOD_RES
<222> LOCATION: (6)..(38)
<223> OTHER INFORMATION: Any amino acid and this region may encompass 2
      to 33 residues wherein some positions may be absent
<220> FEATURE:
<221> NAME/KEY: MOD_RES
<222> LOCATION: (41)..(51)
<223> OTHER INFORMATION: Any amino acid and this region may encompass 2
      to 11 residues wherein some positions may be absent
<220> FEATURE:
<221> NAME/KEY: MOD_RES
<222> LOCATION: (52)..(52)
<223> OTHER INFORMATION: Phe or Tyr
<220> FEATURE:
<221> NAME/KEY: MOD_RES
<222> LOCATION: (54)..(55)
<223> OTHER INFORMATION: Any amino acid and this region may encompass 1
      to 2 residues wherein some positions may be absent
<220> FEATURE:
<221> NAME/KEY: MOD_RES
<222> LOCATION: (57)..(59)
<223> OTHER INFORMATION: Any amino acid and this region may encompass 1
      to 3 residues wherein some positions may be absent

<400> SEQUENCE: 1

Val Xaa Tyr Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Gly Tyr Xaa Xaa Xaa Xaa Xaa Xaa Xaa
            35                  40                  45

Xaa Xaa Xaa Xaa Asp Xaa Xaa Asp Xaa Xaa Xaa Gln
        50                  55                  60

<210> SEQ ID NO 2
<211> LENGTH: 68
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Asp or Asn
<220> FEATURE:
<221> NAME/KEY: MOD_RES
<222> LOCATION: (6)..(28)
<223> OTHER INFORMATION: Any amino acid and this region may encompass 1
```

```
     to 23 residues wherein some positions may be absent
<220> FEATURE:
<221> NAME/KEY: MOD_RES
<222> LOCATION: (30)..(30)
<223> OTHER INFORMATION: Ser or Thr
<220> FEATURE:
<221> NAME/KEY: MOD_RES
<222> LOCATION: (32)..(41)
<223> OTHER INFORMATION: Any amino acid and this region may encompass 1
     to 10 residues wherein some positions may be absent
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (46)..(55)
<223> OTHER INFORMATION: Any amino acid and this region may encompass 1
     to 10 residues wherein some positions may be absent
<220> FEATURE:
<221> NAME/KEY: MOD_RES
<222> LOCATION: (56)..(56)
<223> OTHER INFORMATION: Phe or Tyr
<220> FEATURE:
<221> NAME/KEY: MOD_RES
<222> LOCATION: (58)..(59)
<223> OTHER INFORMATION: Any amino acid and this region may encompass 1
     to 2 residues wherein some positions may be absent
<220> FEATURE:
<221> NAME/KEY: MOD_RES
<222> LOCATION: (61)..(63)
<223> OTHER INFORMATION: Any amino acid and this region may encompass 1
     to 3 residues wherein some positions may be absent
<220> FEATURE:
<221> NAME/KEY: MOD_RES
<222> LOCATION: (65)..(67)
<223> OTHER INFORMATION: Any amino acid

<400> SEQUENCE: 2

Val Xaa Tyr Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Tyr Xaa Thr Xaa
                20                  25                  30

Xaa Xaa Xaa Xaa Xaa Xaa Xaa Xaa Gly Tyr Xaa Leu Xaa Xaa Xaa
            35                  40                  45

Xaa Xaa Xaa Xaa Xaa Xaa Xaa Xaa Asp Xaa Xaa Asp Xaa Xaa Xaa Gln
    50                  55                  60

Xaa Xaa Xaa Val
65

<210> SEQ ID NO 3
<211> LENGTH: 70
<212> TYPE: PRT
<213> ORGANISM: Lactobacillus reuteri
<220> FEATURE:
<223> OTHER INFORMATION: MUB70

<400> SEQUENCE: 3

Val His Val Gln Tyr Ile Asp Gly Glu Thr Asp Gln Met Leu Arg Gln
1               5                   10                  15

Asp Asp Leu Asp Gly Tyr Thr Asp Glu Thr Ile Pro Tyr Ser Thr Ala
                20                  25                  30

Glu Gly Ile Lys Lys Phe Glu Gly Asp Gly Tyr Glu Leu Phe Lys Asp
            35                  40                  45

Asn Phe Pro Ala Gly Glu Lys Phe Asp Asn Asp Thr Asn Asp Gln
    50                  55                  60

Phe Tyr Thr Val Ile Phe
65                  70
```

```
<210> SEQ ID NO 4
<211> LENGTH: 71
<212> TYPE: PRT
<213> ORGANISM: Artificial Sequence
<220> FEATURE:
<223> OTHER INFORMATION: Description of Artificial Sequence: Synthetic
      MUB70 polypeptide

<400> SEQUENCE: 4

Cys Val His Val Gln Tyr Ile Asp Gly Glu Thr Asp Gln Met Leu Arg
1               5                   10                  15

Gln Asp Asp Leu Asp Gly Tyr Thr Asp Glu Thr Ile Pro Tyr Ser Thr
            20                  25                  30

Ala Glu Gly Ile Lys Lys Phe Glu Gly Asp Gly Tyr Glu Leu Phe Lys
        35                  40                  45

Asp Asn Phe Pro Ala Gly Glu Lys Phe Asp Asn Asp Thr Asn Asp
    50                  55                  60

Gln Phe Tyr Thr Val Ile Phe
65                  70

<210> SEQ ID NO 5
<211> LENGTH: 180
<212> TYPE: PRT
<213> ORGANISM: Lactobacillus reuteri
<220> FEATURE:
<223> OTHER INFORMATION: MUB200

<400> SEQUENCE: 5

Ile Asn Val Val Tyr Val Ala Asp Thr Gln Glu Ala Ala Ile Ser Phe
1               5                   10                  15

Tyr Asp Glu Thr Asp His Lys Pro Leu Asn Asp Gln Thr Ile Gln Leu
            20                  25                  30

Thr Gly Lys Thr Gly Glu Lys Ile Ser His Thr Glu Ala Asn Gln Thr
        35                  40                  45

Leu Ala Lys Leu Gly Lys Gln Gly Tyr Val Val Asp Gln Asn Thr Phe
    50                  55                  60

Ala Asp Asp Ala Thr Tyr Asp Asn Asp Thr Gln Ala Pro Gln Glu Phe
65                  70                  75                  80

Thr Ile Tyr Leu Lys His Asp Thr Thr His Thr Asp Ala Thr Ser Ser
                85                  90                  95

Lys Ala Asp Gln Lys Thr Val Ser Glu Thr Ile His Tyr Val Tyr Lys
            100                 105                 110

Asp Gly Val Asn Ala Asn Lys Pro Val Ala Asp Ala Asn Thr Thr
        115                 120                 125

Val Thr Phe Lys Arg Gly Tyr Thr Thr Asp Lys Val Thr Gly Lys Ile
    130                 135                 140

Val Ser Tyr Asp Pro Trp Thr Val Asp Gly Lys Gln Ala Asp Ser Lys
145                 150                 155                 160

Thr Phe Asp Ala Val Lys Ser Pro Val Ile Ala Gly Tyr Thr Ala Asp
                165                 170                 175

Gln Ala Glu Val
            180

<210> SEQ ID NO 6
<211> LENGTH: 183
<212> TYPE: PRT
<213> ORGANISM: Lactobacillus reuteri
<220> FEATURE:
```

<223> OTHER INFORMATION: MUB200

<400> SEQUENCE: 6

```
Thr Val Tyr Tyr Thr Ala Asp Thr Gln Glu Ala Ala Ile Asn Phe Tyr
1               5                   10                  15
Asp Glu Thr Gly His Lys Leu Leu Asp Asn Gln Thr Ile His Leu Thr
                20                  25                  30
Gly Lys Thr Gly Glu Lys Val Asp Arg Thr Gln Ala Asp Gln Thr Leu
            35                  40                  45
Ala Asp Leu Val Lys Gln Gly Tyr Val Leu Asp Lys Glu Asn Thr Ala
        50                  55                  60
Lys Ala Phe Pro Ala Asp Ala Val Tyr Asp Asn Asn Gln Thr Pro
65                  70                  75                  80
Gln Glu Phe Thr Ile Tyr Leu Lys His Gly Thr Thr His Thr Asp Ala
                85                  90                  95
Thr Ser Ser Lys Ala Asp Gln Lys Thr Val Ser Glu Thr Ile His Tyr
            100                 105                 110
Val Tyr Lys Asp Gly Val Asn Ala Asn Lys Pro Val Ala Asp Asp Ala
        115                 120                 125
Asn Thr Thr Val Thr Phe Lys Arg Gly Tyr Thr Thr Asp Lys Val Thr
    130                 135                 140
Gly Lys Ile Val Ser Tyr Asp Pro Trp Thr Val Asp Gly Lys Gln Ala
145                 150                 155                 160
Asp Ser Lys Thr Phe Asp Ala Val Lys Ser Pro Val Ile Ala Gly Tyr
                165                 170                 175
Thr Ala Asp Gln Ala Glu Val
            180
```

<210> SEQ ID NO 7
<211> LENGTH: 174
<212> TYPE: PRT
<213> ORGANISM: Lactobacillus reuteri
<220> FEATURE:
<223> OTHER INFORMATION: MUB200

<400> SEQUENCE: 7

```
Thr Val Tyr Tyr Thr Ala Asp Thr Gln Glu Ala Ala Ile Asn Phe Tyr
1               5                   10                  15
Asp Glu Thr Gly His Lys Leu Leu Asp Asn Gln Thr Ile His Leu Thr
                20                  25                  30
Gly Lys Thr Gly Glu Lys Val Asp Arg Thr Gln Ala Asp Gln Thr Leu
            35                  40                  45
Ala Glu Leu Glu Lys Gln Gly Tyr Val Leu Asp Glu Asn Asn Thr Lys
        50                  55                  60
Leu Gly Phe Pro Ser Asn Ala Ala Tyr Asp Asp Asp Val Lys Pro
65                  70                  75                  80
Gln Glu Phe Thr Ile Tyr Leu Lys His Gly Met Thr His Thr Asp Ala
                85                  90                  95
Thr Asp Lys Asn Ala Glu Gln Lys Ile Val Thr Glu Thr Ile His Tyr
            100                 105                 110
Val Tyr Glu Asn Asn Gln Thr Ala Lys Thr Asp Tyr Thr Ser Ala Val
        115                 120                 125
Asp Phe Lys Arg Gly Tyr Thr Thr Asp Asn Val Thr His Lys Ile Ile
    130                 135                 140
Ser Tyr Asp Pro Trp Met Val Ser Ser Lys Lys Phe Gly Phe Val Lys
145                 150                 155                 160
```

Ser Pro Ala Ile Glu Gly Tyr Thr Pro Asn His Ser Gln Ile
            165                 170

<210> SEQ ID NO 8
<211> LENGTH: 172
<212> TYPE: PRT
<213> ORGANISM: Lactobacillus reuteri
<220> FEATURE:
<223> OTHER INFORMATION: MUB200

<400> SEQUENCE: 8

Thr Val Val Tyr Val Gly Asn Ala Gln Glu Ala Gln Ala Ile Phe Tyr
1               5                   10                  15

Asp Glu Thr Thr Gly Lys Glu Ile Ser Gly Thr Arg Glu Ile Ala Thr
            20                  25                  30

Gly Lys Thr Asp Glu Thr Ile Ser Phe Thr Lys Asp Pro Asn Glu Val
        35                  40                  45

Val Lys Glu Leu Glu Lys Gln Gly Tyr Val Phe Asp Lys Asp Asn Ala
    50                  55                  60

Lys Asn Asn Val Phe Val Ala Gly Thr Ala Tyr Asp Lys Asn Ser Glu
65                  70                  75                  80

Val His Gln Tyr Phe Lys Tyr Leu Lys His Gly His Ala Thr Val
                85                  90                  95

Thr Pro Asp Gln Asp Pro Gln Lys Gly Gln Lys Thr Val Thr Gln Thr
            100                 105                 110

Ile Lys Tyr Glu Tyr Ala Asp Gly Thr Ala Thr Gly Leu Ala Asp Asn
        115                 120                 125

Val Gln Thr Leu Thr Phe Lys Arg Thr Gly Asp Lys Asp Leu Val Thr
    130                 135                 140

His Glu Val Thr Trp Pro Asp Trp Ser Thr Val Ala Gly Gln Gln Thr
145                 150                 155                 160

Ser Val Val Thr Ser Pro Ala Leu Lys Gly Tyr Thr
                165                 170

<210> SEQ ID NO 9
<211> LENGTH: 183
<212> TYPE: PRT
<213> ORGANISM: Lactobacillus reuteri
<220> FEATURE:
<223> OTHER INFORMATION: MUB200

<400> SEQUENCE: 9

Thr Tyr Val Val Lys Tyr Asn Ala Asp Val Gln His Ala Val Ile Asn
1               5                   10                  15

Tyr Ile Asp Gly Glu Ser Asp Glu Ile Leu His Thr Asp Lys Val Asn
            20                  25                  30

Gly His Ser Asp Glu Lys Ile Asn Tyr Ser Thr Ala Asp Met Ile Lys
        35                  40                  45

Gln Leu Glu Ala Lys Gly Tyr Glu Leu Phe Lys Asp Asn Phe Pro Ala
    50                  55                  60

Gly Glu Lys Phe Asp Asn Asp Thr Asn Asp Gln Phe Tyr Thr Val
65                  70                  75                  80

Ile Phe Lys His His Arg Glu Asn Val Asp Pro Asn His Ser Ser Ala
                85                  90                  95

Asp Gly Thr Lys Gly Thr Lys Thr Leu Thr Glu Thr Val His Tyr Lys
            100                 105                 110

Tyr Ala Asn Gly Thr Lys Ala Ala Glu Asp Gln Thr Ala Gln Val Thr

```
                115                 120                 125
Phe Thr Arg Asn Gly Val Leu Asp Asp Val Thr Gly Ile Val Ala Trp
    130                 135                 140
Gly Lys Trp Asn Glu Ala Ser Gln Ser Tyr Lys Ala Leu Thr Ser Pro
145                 150                 155                 160
Thr Ile Ala Gly Tyr Ala Pro Ser Glu Val Val Lys Arg Ser Ser
                165                 170                 175
Asn Ser Asp Ala Glu Gln Gly
            180
```

```
<210> SEQ ID NO 10
<211> LENGTH: 183
<212> TYPE: PRT
<213> ORGANISM: Lactobacillus reuteri
<220> FEATURE:
<223> OTHER INFORMATION: MUB200

<400> SEQUENCE: 10

Thr Leu Thr Val Ile Tyr Thr Ala Asp Ala Gln Lys Val His Val Gln
1               5                   10                  15
Tyr Ile Asp Gly Glu Thr Asp Gln Met Leu Arg Gln Asp Asp Leu Asp
                20                  25                  30
Gly Tyr Thr Asp Glu Thr Ile Pro Tyr Ser Thr Ala Glu Gly Ile Lys
            35                  40                  45
Lys Phe Glu Gly Asp Gly Tyr Glu Leu Phe Lys Asp Asn Phe Pro Ala
    50                  55                  60
Gly Glu Lys Phe Asp Asn Asp Lys Asn Asp Gln Thr Tyr Thr Val
65                  70                  75                  80
Ile Phe Lys His His Arg Glu Asn Val Asp Pro Asn His Ser Ser Ala
                85                  90                  95
Asp Gly Thr Lys Gly Thr Lys Thr Leu Thr Glu Thr Val His Tyr Lys
                100                 105                 110
Tyr Ala Asp Gly Thr Lys Ala Ala Glu Asp Gln Thr Ala Gln Val Thr
            115                 120                 125
Phe Thr Arg Asn Gly Val Leu Asp Asp Val Thr Gly Ile Val Ala Trp
    130                 135                 140
Gly Lys Trp Asn Glu Ala Ser Gln Ser Tyr Lys Ala Leu Thr Ser Pro
145                 150                 155                 160
Thr Ile Ala Gly Tyr Thr Pro Ser Glu Val Val Lys Arg Ser Ser
                165                 170                 175
Asn Ser Asp Ala Glu Gln Gly
            180
```

```
<210> SEQ ID NO 11
<211> LENGTH: 183
<212> TYPE: PRT
<213> ORGANISM: Lactobacillus reuteri
<220> FEATURE:
<223> OTHER INFORMATION: MUB200

<400> SEQUENCE: 11

Thr Leu Thr Val Ile Tyr Thr Ala Asp Ala Gln Lys Val His Val Gln
1               5                   10                  15
Tyr Ile Asp Gly Glu Thr Asp Gln Met Leu Arg Gln Asp Asp Leu Asp
                20                  25                  30
Gly Tyr Thr Asp Glu Thr Ile Pro Tyr Ser Thr Ala Glu Gly Ile Lys
            35                  40                  45
```

Lys Phe Glu Gly Asp Gly Tyr Glu Leu Phe Lys Asp Asn Phe Pro Ala
    50                  55                  60

Gly Glu Lys Phe Asp Asn Asp Thr Asn Asp Gln Phe Tyr Thr Val
65                  70                  75                  80

Ile Phe Lys His His Arg Glu Asn Val Asp Pro Asn His Ser Ser Ala
                85                  90                  95

Asp Gly Thr Lys Gly Thr Lys Thr Leu Thr Glu Thr Val His Tyr Lys
                100                 105                 110

Tyr Ala Asn Gly Thr Lys Ala Ala Glu Asp Gln Thr Ala Gln Val Thr
            115                 120                 125

Phe Thr Arg Asn Gly Val Leu Asp Asp Val Thr Gly Ile Val Ala Trp
130                 135                 140

Gly Lys Trp Asn Glu Ala Ser Gln Ser Tyr Lys Ala Leu Thr Ser Pro
145                 150                 155                 160

Thr Ile Ala Gly Tyr Ala Pro Ser Glu Ala Val Val Lys Arg Ser Ser
                165                 170                 175

Asn Ser Asp Ala Glu Gln Gly
            180

<210> SEQ ID NO 12
<211> LENGTH: 183
<212> TYPE: PRT
<213> ORGANISM: Lactobacillus reuteri
<220> FEATURE:
<223> OTHER INFORMATION: MUB200

<400> SEQUENCE: 12

Thr Leu Thr Val Ile Tyr Thr Ala Asp Ala Gln Lys Val His Val Gln
1               5                   10                  15

Tyr Ile Asp Gly Glu Thr Asp Gln Met Leu Arg Gln Asp Asp Leu Asp
            20                  25                  30

Gly Tyr Thr Asp Glu Thr Ile Pro Tyr Ser Thr Ala Glu Gly Ile Lys
        35                  40                  45

Lys Phe Glu Gly Asp Gly Tyr Glu Leu Phe Lys Asp Asn Phe Pro Ala
    50                  55                  60

Gly Glu Lys Phe Asp Asn Asp Lys Asn Asp Gln Thr Tyr Thr Val
65                  70                  75                  80

Ile Phe Lys His His Arg Glu Asn Val Asp Pro Asn His Ser Ser Ala
                85                  90                  95

Asp Gly Thr Lys Gly Thr Lys Thr Leu Thr Glu Thr Val His Tyr Lys
                100                 105                 110

Tyr Ala Asp Gly Thr Lys Ala Ala Glu Asp Gln Thr Ala Gln Val Thr
            115                 120                 125

Phe Thr Arg Asn Gly Val Leu Asp Asp Val Thr Gly Ile Val Ala Trp
130                 135                 140

Gly Lys Trp Asn Glu Ala Ser Gln Ser Tyr Lys Ala Leu Thr Ser Pro
145                 150                 155                 160

Thr Ile Ala Gly Tyr Thr Pro Ser Glu Ala Val Val Lys Arg Ser Ser
                165                 170                 175

Asn Ser Asp Ala Glu Gln Gly
            180

<210> SEQ ID NO 13
<211> LENGTH: 183
<212> TYPE: PRT
<213> ORGANISM: Lactobacillus reuteri
<220> FEATURE:

<223> OTHER INFORMATION: MUB200

<400> SEQUENCE: 13

```
Thr Leu Thr Val Ile Tyr Thr Ala Asp Ala Gln Lys Val His Val Gln
1               5                   10                  15
Tyr Ile Asp Gly Glu Thr Asp Gln Met Leu Arg Gln Asp Asp Leu Asp
            20                  25                  30
Gly Tyr Thr Asp Glu Thr Ile Pro Tyr Ser Thr Ala Glu Gly Ile Lys
        35                  40                  45
Lys Phe Glu Gly Asp Gly Tyr Glu Leu Phe Lys Asp Asn Phe Pro Ala
    50                  55                  60
Gly Glu Lys Phe Asp Asn Asp Lys Asn Asp Gln Thr Tyr Thr Val
65                  70                  75                  80
Ile Phe Lys His His Arg Glu Asn Val Asp Pro Asn His Ser Ser Ala
                85                  90                  95
Asp Gly Thr Lys Gly Thr Lys Thr Leu Thr Glu Thr Val His Tyr Lys
            100                 105                 110
Tyr Ala Asp Gly Thr Lys Ala Ala Glu Asp Gln Thr Ala Gln Val Thr
        115                 120                 125
Phe Thr Arg Asn Gly Val Leu Asp Asp Val Thr Gly Ile Val Ala Trp
    130                 135                 140
Gly Lys Trp Asn Glu Ala Ser Gln Ser Tyr Lys Ala Leu Thr Ser Pro
145                 150                 155                 160
Thr Ile Ala Gly Tyr Thr Pro Ser Glu Ala Val Val Lys Arg Ser Ser
                165                 170                 175
Asn Ser Asp Ala Glu Gln Gly
            180
```

<210> SEQ ID NO 14
<211> LENGTH: 183
<212> TYPE: PRT
<213> ORGANISM: Lactobacillus reuteri
<220> FEATURE:
<223> OTHER INFORMATION: MUB200

<400> SEQUENCE: 14

```
Thr Leu Thr Val Ile Tyr Thr Ala Asp Ala Gln Lys Val His Val Gln
1               5                   10                  15
Tyr Ile Asp Gly Glu Thr Asp Gln Met Leu Arg Gln Asp Asp Leu Asp
            20                  25                  30
Gly Tyr Thr Asp Glu Thr Ile Pro Tyr Ser Thr Ala Glu Gly Ile Lys
        35                  40                  45
Lys Phe Glu Gly Asp Gly Tyr Glu Leu Phe Lys Asp Asn Phe Pro Ala
    50                  55                  60
Gly Glu Lys Phe Asp Asn Asp Lys Thr Asp Gln Thr Tyr Thr Val
65                  70                  75                  80
Ile Phe Lys His His Arg Glu Asn Val Asp Pro Asn His Ser Ser Ala
                85                  90                  95
Asp Gly Thr Lys Gly Thr Lys Thr Leu Thr Glu Thr Val His Tyr Lys
            100                 105                 110
Tyr Ala Asp Gly Thr Lys Ala Ala Glu Asp Gln Thr Ala Gln Val Thr
        115                 120                 125
Phe Thr Arg Asn Gly Val Leu Asp Asp Val Thr Gly Ile Val Ala Trp
    130                 135                 140
Gly Lys Trp Asn Glu Ala Ser Gln Ser Tyr Lys Ala Leu Thr Ser Pro
145                 150                 155                 160
```

Thr Ile Ala Gly Tyr Thr Pro Ser Glu Ala Val Val Lys Arg Ser Ser
            165                 170                 175

Asn Ser Asp Ala Glu Gln Gly
            180

<210> SEQ ID NO 15
<211> LENGTH: 183
<212> TYPE: PRT
<213> ORGANISM: Lactobacillus reuteri
<220> FEATURE:
<223> OTHER INFORMATION: MUB200

<400> SEQUENCE: 15

Thr Leu Thr Val Ile Tyr Thr Ala Asp Ala Gln Thr Ala Tyr Val Lys
1               5                   10                  15

Tyr Val Asp Asp Thr Thr Gly Glu Thr Leu Arg Gln Asp Asp Leu His
            20                  25                  30

Gly Tyr Thr Asp Glu Thr Ile Pro Tyr Ser Thr Ala Glu Gly Ile Lys
        35                  40                  45

Lys Phe Glu Gly Asp Gly Tyr Glu Leu Phe Lys Asp Asn Phe Pro Ala
    50                  55                  60

Gly Glu Lys Phe Asp Asn Asp Lys Thr Asp Gln Thr Tyr Thr Val
65                  70                  75                  80

Ile Phe Lys His His Arg Glu Asn Val Asp Pro Asn His Ser Ser Ala
                85                  90                  95

Asp Gly Thr Lys Gly Thr Lys Thr Leu Thr Glu Thr Val His Tyr Lys
            100                 105                 110

Tyr Ala Asp Gly Thr Lys Ala Ala Glu Asp Gln Thr Ala Gln Val Thr
        115                 120                 125

Phe Thr Arg Asn Gly Val Leu Asp Asp Val Thr Gly Ile Val Ala Trp
    130                 135                 140

Gly Lys Trp Asn Glu Ala Ser Gln Ser Tyr Lys Ala Leu Thr Ser Pro
145                 150                 155                 160

Thr Ile Ala Gly Tyr Thr Pro Ser Glu Ala Val Val Lys Arg Ser Ser
                165                 170                 175

Asn Ser Asp Ala Glu Gln Gly
            180

<210> SEQ ID NO 16
<211> LENGTH: 192
<212> TYPE: PRT
<213> ORGANISM: Lactobacillus reuteri
<220> FEATURE:
<223> OTHER INFORMATION: MUB200

<400> SEQUENCE: 16

Thr Val Val Tyr Val Gly Asp Pro Gln Glu Ala Gln Ala Ile Phe Tyr
1               5                   10                  15

Asp Glu Thr Thr Gly Lys Glu Ile Ser Asn Thr Arg Glu Ile Val Asn
            20                  25                  30

Gly Lys Thr Asp Glu Thr Ile Gly Phe Thr Lys Asp Pro Asn Glu Val
        35                  40                  45

Val Lys Glu Leu Glu Lys Gln Gly Tyr Val Phe Asp Lys Asp Asn Ala
    50                  55                  60

Asn Asn Asn Val Phe Ala Ala Gly Thr Thr Tyr Asp Lys Asn Ser Glu
65                  70                  75                  80

Val His Gln Tyr Phe Lys Tyr Tyr Phe Thr His Ala Thr Thr Ile Val

-continued

```
                    85                  90                  95
Thr Pro Asp Asn Pro Lys Thr Pro Ala Asp Val Leu Pro Asp Asn Pro
            100                 105                 110

Gly Lys Asn Tyr Pro Ser Gly Val Ala Lys Asp Asp Leu Asn Lys Thr
        115                 120                 125

Val Thr Arg Thr Ile Asn Ile Thr Thr Pro Asp Gly Lys Thr Gln Thr
    130                 135                 140

Ile Thr Gln Lys Ala Glu Phe Thr Arg Ser Ala Thr Val Asp Glu Val
145                 150                 155                 160

Thr Gly Glu Val Thr Tyr Gly Pro Trp Ser Lys Asn Val Val Leu Glu
                165                 170                 175

Ser Val Asp Val Pro Asn Ile Ser Gly Tyr Val Pro Ser Ala Ser Val
            180                 185                 190

<210> SEQ ID NO 17
<211> LENGTH: 10020
<212> TYPE: DNA
<213> ORGANISM: Lactobacillus reuteri
<220> FEATURE:
<223> OTHER INFORMATION: MUB
<220> FEATURE:
<221> NAME/KEY: CDS
<222> LOCATION: (121)..(9927)

<400> SEQUENCE: 17
ggaagattcg ctgcaattaa ctttaaagaa gttgcaacag caaatgccaa taattgttgg      60
ttgctgaatg aatgttgatt ttttcataat gcaaaaattt taagggagag ttttagtaat     120 atg gtc ggg aaa aac aat aat tat gta agg gaa agc aaa tct aat gag      168
Met Val Gly Lys Asn Asn Asn Tyr Val Arg Glu Ser Lys Ser Asn Glu
1               5                   10                  15 cat ttt caa cgg ttt gcg ctg cgc aaa ctg agc gtt ggg gtt gtc tcg      216
His Phe Gln Arg Phe Ala Leu Arg Lys Leu Ser Val Gly Val Val Ser
                20                  25                  30 gtt gcc gtt gcg gct ggt ttt tat tta ggc agt ggt gca aca gca cag      264
Val Ala Val Ala Ala Gly Phe Tyr Leu Gly Ser Gly Ala Thr Ala Gln
            35                  40                  45 gct gca act act gaa tcg aat gca tcg gct aaa act gaa cag gtt gtg      312
Ala Ala Thr Thr Glu Ser Asn Ala Ser Ala Lys Thr Glu Gln Val Val
        50                  55                  60 caa cag aac tca act tca gct gcc agt gac tca act tca aca tct aat      360
Gln Gln Asn Ser Thr Ser Ala Ala Ser Asp Ser Thr Ser Thr Ser Asn
65                  70                  75                  80 agc agt gca gcc gtg tcc aca agc agt gct acg ccg gta agc acc gag      408
Ser Ser Ala Ala Val Ser Thr Ser Ser Ala Thr Pro Val Ser Thr Glu
                85                  90                  95 tct gct tct agc atg acg gtt tct gat ttg cca gca tcg gcc agc gcg      456
Ser Ala Ser Ser Met Thr Val Ser Asp Leu Pro Ala Ser Ala Ser Ala
                100                 105                 110 gct tca gac aat caa gct tcg gct gcc aat gcc agt gaa agc agt agt      504
Ala Ser Asp Asn Gln Ala Ser Ala Ala Asn Ala Ser Glu Ser Ser Ser
        115                 120                 125 cag tcg gca tca agc tca gtt gcc agc gat gcc gca gct act gta agc      552
Gln Ser Ala Ser Ser Ser Val Ala Ser Asp Ala Ala Ala Thr Val Ser
    130                 135                 140 aaa gac tca cag gca gct agt gaa gcc aac agt caa agc gct gct gat      600
Lys Asp Ser Gln Ala Ala Ser Glu Ala Asn Ser Gln Ser Ala Ala Asp
145                 150                 155                 160 gta gaa aca gta cag ttg cca acg tca gcc gct aat gcc aat gct aat      648
Val Glu Thr Val Gln Leu Pro Thr Ser Ala Ala Asn Ala Asn Ala Asn
```

|  |  |  |  |  |  |  |  |  |  |  |  |  |  |  |  |
|---|---|---|---|---|---|---|---|---|---|---|---|---|---|---|---|
| | | 165 | | | | 170 | | | | 175 | | | | | |

```
gaa agc caa gca gcc aat att ttg ggt gct caa gct gtt caa aag gct    696
Glu Ser Gln Ala Ala Asn Ile Leu Gly Ala Gln Ala Val Gln Lys Ala
            180                 185                 190 gcc aat caa cag gcg cca gcc gga ttt acg gtt act gac cca aat tat    744
Ala Asn Gln Gln Ala Pro Ala Gly Phe Thr Val Thr Asp Pro Asn Tyr
                195                 200                 205 ccg gca gaa atg tat aaa gat cca gat gcc agt cac tat acc tac tgg    792
Pro Ala Glu Met Tyr Lys Asp Pro Asp Ala Ser His Tyr Thr Tyr Trp
        210                 215                 220 tgg gca caa agc tcg aat ggc gag tat aac ctg gtt ctt tca act gat    840
Trp Ala Gln Ser Ser Asn Gly Glu Tyr Asn Leu Val Leu Ser Thr Asp
225                 230                 235                 240 cgg aat ggt gat ggc aag gtt tat gtc ttc ttg ctg ggc aac aat aat    888
Arg Asn Gly Asp Gly Lys Val Tyr Val Phe Leu Leu Gly Asn Asn Asn
                245                 250                 255 aat gtt tta ggt aag tac acg gtt gat aaa aat aaa tca aca gaa gta    936
Asn Val Leu Gly Lys Tyr Thr Val Asp Lys Asn Lys Ser Thr Glu Val
        260                 265                 270 gct act gat gac gag gga gat ttt ggc aca gtt tac aat gat ggt cag    984
Ala Thr Asp Asp Glu Gly Asp Phe Gly Thr Val Tyr Asn Asp Gly Gln
            275                 280                 285 tca ggt gtc ttt gtt act tct gat ggt acc tgg aag tca aag ttc aac   1032
Ser Gly Val Phe Val Thr Ser Asp Gly Thr Trp Lys Ser Lys Phe Asn
                290                 295                 300 gtt ttt gac cct aag gcg ggc gag gat gat gga gac tat ggc agt att   1080
Val Phe Asp Pro Lys Ala Gly Glu Asp Asp Gly Asp Tyr Gly Ser Ile
305                 310                 315                 320 agt ttc atg atc cca caa gta gaa acg cag acg acg tac tac gtt act   1128
Ser Phe Met Ile Pro Gln Val Glu Thr Gln Thr Thr Tyr Val Thr
                325                 330                 335 tat ttt gat agc aag ggt aac aag gtc gat aaa cca atc gag gtc agt   1176
Tyr Phe Asp Ser Lys Gly Asn Lys Val Asp Lys Pro Ile Glu Val Ser
        340                 345                 350 gac cct gtc att caa aaa ggt ctg gat ggt caa atc tat acg aca aag   1224
Asp Pro Val Ile Gln Lys Gly Leu Asp Gly Gln Ile Tyr Thr Thr Lys
            355                 360                 365 ggt ggc aaa gta atc aat ggc tat ttt gcc aaa gag cca aaa aat gcc   1272
Gly Gly Lys Val Ile Asn Gly Tyr Phe Ala Lys Glu Pro Lys Asn Ala
                370                 375                 380 cat ggc ttc atg tcg cca ttt ggc aag cag ggt gca atc tac act aaa   1320
His Gly Phe Met Ser Pro Phe Gly Lys Gln Gly Ala Ile Tyr Thr Lys
385                 390                 395                 400 gat tgg cat gat ggg ctt aaa gcc acc ttt acc gaa act gat acc aag   1368
Asp Trp His Asp Gly Leu Lys Ala Thr Phe Thr Glu Thr Asp Thr Lys
                405                 410                 415 acc ggc ttg atg cat gtt gtt gtg aaa cat tat tat cat agt tgg ggt   1416
Thr Gly Leu Met His Val Val Val Lys His Tyr Tyr His Ser Trp Gly
        420                 425                 430 tgg gga act tgg cgg aca gta aaa gag ttt gat ctt gcc cca ggt caa   1464
Trp Gly Thr Trp Arg Thr Val Lys Glu Phe Asp Leu Ala Pro Gly Gln
            435                 440                 445 tca gag aaa gtt gac tat gat gtc tat aaa tca gtt act att cac agc   1512
Ser Glu Lys Val Asp Tyr Asp Val Tyr Lys Ser Val Thr Ile His Ser
                450                 455                 460 atc tac att cca cag acg atc aac att caa tac acc tat gaa aag ctg   1560
Ile Tyr Ile Pro Gln Thr Ile Asn Ile Gln Tyr Thr Tyr Glu Lys Leu
465                 470                 475                 480 ggc aat ctg gtc atc agt tct gac agc aag tcc ttc cca gct gaa gat   1608
Gly Asn Leu Val Ile Ser Ser Asp Ser Lys Ser Phe Pro Ala Glu Asp
```

```
                Gly Asn Leu Val Ile Ser Ser Asp Ser Lys Ser Phe Pro Ala Glu Asp
                                    485                 490                 495 aag act caa tat cca aat gat aag tct gac tca acc aag gcc ggt aat          1656
Lys Thr Gln Tyr Pro Asn Asp Lys Ser Asp Ser Thr Lys Ala Gly Asn
            500                 505                 510 gtt aca att cca aag gta gcc ggc ttt acg cca acg atc aat gac aag          1704
Val Thr Ile Pro Lys Val Ala Gly Phe Thr Pro Thr Ile Asn Asp Lys
            515                 520                 525 acg gtg aca aac tac acg ttt aac cct tct gat tac gtc agc gat ctg          1752
Thr Val Thr Asn Tyr Thr Phe Asn Pro Ser Asp Tyr Val Ser Asp Leu
            530                 535                 540 agt aag gac att aat gtt gtt tat gta gct gac acg caa gaa gct gcc          1800
Ser Lys Asp Ile Asn Val Val Tyr Val Ala Asp Thr Gln Glu Ala Ala
545                 550                 555                 560 atc agc ttc tat gac gag aca gac cac aag cca ctg aat gac caa acg          1848
Ile Ser Phe Tyr Asp Glu Thr Asp His Lys Pro Leu Asn Asp Gln Thr
                565                 570                 575 att cag ctg act ggc aag act ggt gaa aag atc agc cat acc gaa gct          1896
Ile Gln Leu Thr Gly Lys Thr Gly Glu Lys Ile Ser His Thr Glu Ala
            580                 585                 590 aat caa aca ctg gct aag ctg gga aag caa ggc tat gtt gtc gac cag          1944
Asn Gln Thr Leu Ala Lys Leu Gly Lys Gln Gly Tyr Val Val Asp Gln
            595                 600                 605 aat act ttt gct gat gat gca acg tat gac aac gat acg caa gca cca          1992
Asn Thr Phe Ala Asp Asp Ala Thr Tyr Asp Asn Asp Thr Gln Ala Pro
610                 615                 620 caa gag ttt acg atc tac ctc aag cat gat acg acc cat act gac gca          2040
Gln Glu Phe Thr Ile Tyr Leu Lys His Asp Thr Thr His Thr Asp Ala
625                 630                 635                 640 act agc tca aag gca gat caa aag acc gtc agc gaa acg att cac tac          2088
Thr Ser Ser Lys Ala Asp Gln Lys Thr Val Ser Glu Thr Ile His Tyr
                645                 650                 655 gtc tac aaa gat ggg gtc aac gct aat aag ccg gta gct gat gac gct          2136
Val Tyr Lys Asp Gly Val Asn Ala Asn Lys Pro Val Ala Asp Asp Ala
            660                 665                 670 aat aca acg gtt acc ttc aaa cgc ggc tac acg act gac aaa gtt acg          2184
Asn Thr Thr Val Thr Phe Lys Arg Gly Tyr Thr Thr Asp Lys Val Thr
            675                 680                 685 gga aag att gtt tcc tat gat cct tgg acg gtt gat ggc aag caa gcc          2232
Gly Lys Ile Val Ser Tyr Asp Pro Trp Thr Val Asp Gly Lys Gln Ala
            690                 695                 700 gac agc aag acg ttt gat gcc gtc aag agt cca gtc att gct ggt tac          2280
Asp Ser Lys Thr Phe Asp Ala Val Lys Ser Pro Val Ile Ala Gly Tyr
705                 710                 715                 720 acg gcc gat caa gca gaa gtt gcc gct caa acg gta acg cca gat tcc          2328
Thr Ala Asp Gln Ala Glu Val Ala Ala Gln Thr Val Thr Pro Asp Ser
                725                 730                 735 caa aat att aac aag aca gtt tac tat acc gct gac acg caa gaa gct          2376
Gln Asn Ile Asn Lys Thr Val Tyr Tyr Thr Ala Asp Thr Gln Glu Ala
            740                 745                 750 gcc atc aac ttc tat gac gag aca ggc cac aag ctg tta gat aac caa          2424
Ala Ile Asn Phe Tyr Asp Glu Thr Gly His Lys Leu Leu Asp Asn Gln
            755                 760                 765 acg att cat ttg act ggc aag acc ggt gaa aag gta gac cgg acg caa          2472
Thr Ile His Leu Thr Gly Lys Thr Gly Glu Lys Val Asp Arg Thr Gln
            770                 775                 780 gcg gac cag acg ttg gct gat ctg gta aag caa ggc tat gtt ttg gat          2520
Ala Asp Gln Thr Leu Ala Asp Leu Val Lys Gln Gly Tyr Val Leu Asp
785                 790                 795                 800
```

```
aaa gaa aac acg gcc aag gca ttc cca gct gac gcg gta tat gac aac         2568
Lys Glu Asn Thr Ala Lys Ala Phe Pro Ala Asp Ala Val Tyr Asp Asn
            805                 810                 815 aat gac caa acg cca caa gag ttt acg atc tac ctc aag cat ggt acg         2616
Asn Asp Gln Thr Pro Gln Glu Phe Thr Ile Tyr Leu Lys His Gly Thr
        820                 825                 830 acc cat act gac gca acc agc tca aag gca gat caa aag acc gtc agc         2664
Thr His Thr Asp Ala Thr Ser Ser Lys Ala Asp Gln Lys Thr Val Ser
            835                 840                 845 gaa acg att cac tac gtc tac aaa gat ggg gtc aac gct aat aag ccg         2712
Glu Thr Ile His Tyr Val Tyr Lys Asp Gly Val Asn Ala Asn Lys Pro
        850                 855                 860 gta gct gat gac gct aat aca acg gtt acc ttc aaa cgc ggc tac acg         2760
Val Ala Asp Asp Ala Asn Thr Thr Val Thr Phe Lys Arg Gly Tyr Thr
865                 870                 875                 880 act gac aaa gtt acg gga aag att gtt tcc tat gat cct tgg acg gtt         2808
Thr Asp Lys Val Thr Gly Lys Ile Val Ser Tyr Asp Pro Trp Thr Val
            885                 890                 895 gat ggc aag caa gcc gac agc aag acg ttt gat gcc gtc aag agt cca         2856
Asp Gly Lys Gln Ala Asp Ser Lys Thr Phe Asp Ala Val Lys Ser Pro
        900                 905                 910 gtc att gct ggt tac acg gcc gat caa gca gaa gtt gcc gct caa acg         2904
Val Ile Ala Gly Tyr Thr Ala Asp Gln Ala Glu Val Ala Ala Gln Thr
            915                 920                 925 gta acg cca gat tcc caa aat att aac aag aca gtt tac tat acc gct         2952
Val Thr Pro Asp Ser Gln Asn Ile Asn Lys Thr Val Tyr Tyr Thr Ala
        930                 935                 940 gac acg caa gaa gct gcc atc aac ttc tat gac gag aca ggc cac aag         3000
Asp Thr Gln Glu Ala Ala Ile Asn Phe Tyr Asp Glu Thr Gly His Lys
945                 950                 955                 960 ctg tta gat aac caa acg att cat ctg act ggc aag act ggt gaa aag         3048
Leu Leu Asp Asn Gln Thr Ile His Leu Thr Gly Lys Thr Gly Glu Lys
            965                 970                 975 gtt gat cgg acg caa gcg gac cag acg ctg gct gaa ctg gaa aaa caa         3096
Val Asp Arg Thr Gln Ala Asp Gln Thr Leu Ala Glu Leu Glu Lys Gln
        980                 985                 990 ggc tac gtt ctg gat gag aat aac act aaa ctg gga ttc cca tcc aat        3144
Gly Tyr Val Leu Asp Glu Asn Asn Thr Lys Leu Gly Phe Pro Ser Asn
            995                 1000                1005 gca gcg tat gac gat gat gac gtt aag cca caa gag ttt acg atc            3189
Ala Ala Tyr Asp Asp Asp Asp Val Lys Pro Gln Glu Phe Thr Ile
        1010                1015                1020 tat ctg aag cat ggc atg acg cat acc gat gca acc gac aag aat            3234
Tyr Leu Lys His Gly Met Thr His Thr Asp Ala Thr Asp Lys Asn
1025                1030                1035 gct gaa caa aag att gtt acg gaa acg att cac tac gtt tac gaa            3279
Ala Glu Gln Lys Ile Val Thr Glu Thr Ile His Tyr Val Tyr Glu
        1040                1045                1050 aac aac cag act gct aag aca gac tac acg tca gcg gtt gac ttt            3324
Asn Asn Gln Thr Ala Lys Thr Asp Tyr Thr Ser Ala Val Asp Phe
        1055                1060                1065 aag cgc ggc tac acg act gac aac gtt acg cat aag att att tcc            3369
Lys Arg Gly Tyr Thr Thr Asp Asn Val Thr His Lys Ile Ile Ser
        1070                1075                1080 tac gat cca tgg atg gta tcc agc aag aag ttt ggt ttc gta aag            3414
Tyr Asp Pro Trp Met Val Ser Ser Lys Lys Phe Gly Phe Val Lys
        1085                1090                1095 agt cca gcc att gaa ggc tac acg cca aac cat tcg cag att gat            3459
Ser Pro Ala Ile Glu Gly Tyr Thr Pro Asn His Ser Gln Ile Asp
        1100                1105                1110
```

```
gaa atc act gtt acg cca gat tca aaa gac gtc gtc aag acg gtg   3504
Glu Ile Thr Val Thr Pro Asp Ser Lys Asp Val Val Lys Thr Val
    1115                1120                1125 gtt tat gtt ggg aat gcc caa gaa gcc caa gcc atc ttc tat gat   3549
Val Tyr Val Gly Asn Ala Gln Glu Ala Gln Ala Ile Phe Tyr Asp
    1130                1135                1140 gaa acg acg ggc aaa gaa atc agt ggg aca cgt gaa att gca act   3594
Glu Thr Thr Gly Lys Glu Ile Ser Gly Thr Arg Glu Ile Ala Thr
    1145                1150                1155 ggc aag act gat gaa acg atc agc ttt acc aag gat cca aat gaa   3639
Gly Lys Thr Asp Glu Thr Ile Ser Phe Thr Lys Asp Pro Asn Glu
    1160                1165                1170 gtc gtt aag gaa ctc gaa aag cag ggt tac gtt ttt gac aag gat   3684
Val Val Lys Glu Leu Glu Lys Gln Gly Tyr Val Phe Asp Lys Asp
    1175                1180                1185 aac gct aag aat aat gtc ttt gtc gct gga acg gcc tac gac aag   3729
Asn Ala Lys Asn Asn Val Phe Val Ala Gly Thr Ala Tyr Asp Lys
    1190                1195                1200 aat tcc gaa gtt cac caa tac ttc aag tac tac ctg aag cac gga   3774
Asn Ser Glu Val His Gln Tyr Phe Lys Tyr Tyr Leu Lys His Gly
    1205                1210                1215 cat gcg acg gta acg cca gac caa gat cca caa aaa ggt caa aag   3819
His Ala Thr Val Thr Pro Asp Gln Asp Pro Gln Lys Gly Gln Lys
    1220                1225                1230 acg gtt aca cag aca att aag tac gaa tac gct gat ggc acg gca   3864
Thr Val Thr Gln Thr Ile Lys Tyr Glu Tyr Ala Asp Gly Thr Ala
    1235                1240                1245 act ggt ttg gct gat aat gtg caa acc ttg acg ttc aag cgt aca   3909
Thr Gly Leu Ala Asp Asn Val Gln Thr Leu Thr Phe Lys Arg Thr
    1250                1255                1260 ggt gac aag gat ctc gtt act cat gaa gta acc tgg cca gac tgg   3954
Gly Asp Lys Asp Leu Val Thr His Glu Val Thr Trp Pro Asp Trp
    1265                1270                1275 tca acg gtt gcc ggt caa caa acc agt gtt gta acc agt cca gct   3999
Ser Thr Val Ala Gly Gln Gln Thr Ser Val Val Thr Ser Pro Ala
    1280                1285                1290 ctc aag ggc tac act gct gat acc aac gaa att cca gcc att acc   4044
Leu Lys Gly Tyr Thr Ala Asp Thr Asn Glu Ile Pro Ala Ile Thr
    1295                1300                1305 tac cat gct ggt gac agt gat gtt act tat gtt gtt aag tac aat   4089
Tyr His Ala Gly Asp Ser Asp Val Thr Tyr Val Val Lys Tyr Asn
    1310                1315                1320 gcc gat gtt caa cat gct gtt atc aat tac att gat ggc gaa agt   4134
Ala Asp Val Gln His Ala Val Ile Asn Tyr Ile Asp Gly Glu Ser
    1325                1330                1335 gat gag ata ctg cac act gat aag gtt aat ggc cac tct gac gaa   4179
Asp Glu Ile Leu His Thr Asp Lys Val Asn Gly His Ser Asp Glu
    1340                1345                1350 aag atc aac tac agc act gct gat atg atc aaa cag ttg gaa gcc   4224
Lys Ile Asn Tyr Ser Thr Ala Asp Met Ile Lys Gln Leu Glu Ala
    1355                1360                1365 aag ggt tat gaa ctg ttc aag gac aac ttc cca gct ggt gag aag   4269
Lys Gly Tyr Glu Leu Phe Lys Asp Asn Phe Pro Ala Gly Glu Lys
    1370                1375                1380 ttc gat aac gat gac acc aac gat caa ttc tac acg gta atc ttc   4314
Phe Asp Asn Asp Asp Thr Asn Asp Gln Phe Tyr Thr Val Ile Phe
    1385                1390                1395 aag cac cat cgt gaa aac gtt gat cca aac cac tcc tcg gct gat   4359
Lys His His Arg Glu Asn Val Asp Pro Asn His Ser Ser Ala Asp
```

-continued

```
                      1400                1405                1410
ggc acg aag ggt acg aag acg ctg acg gaa acg gtt cac tac aag        4404
Gly Thr Lys Gly Thr Lys Thr Leu Thr Glu Thr Val His Tyr Lys
    1415                1420                1425 tac gct aat ggc acc aag gcg gct gaa gat cag acg gct cag gta        4449
Tyr Ala Asn Gly Thr Lys Ala Ala Glu Asp Gln Thr Ala Gln Val
    1430                1435                1440 acg ttt acg cgg aac ggt gtc ctg gat gac gtt acg ggt atc gtg        4494
Thr Phe Thr Arg Asn Gly Val Leu Asp Asp Val Thr Gly Ile Val
    1445                1450                1455 gcc tgg ggc aag tgg aac gaa gcc agc cag agc tac aag gct ttg        4539
Ala Trp Gly Lys Trp Asn Glu Ala Ser Gln Ser Tyr Lys Ala Leu
    1460                1465                1470 act tca cca acg att gcc ggc tac gcg cca agc gaa gcg gtg gta        4584
Thr Ser Pro Thr Ile Ala Gly Tyr Ala Pro Ser Glu Ala Val Val
    1475                1480                1485 aag cgc agt tcc aac agc gat gcc gaa caa ggc cca acg ctt acg        4629
Lys Arg Ser Ser Asn Ser Asp Ala Glu Gln Gly Pro Thr Leu Thr
    1490                1495                1500 gtc att tac acg gct gat gcc caa aag gtt cac gtt caa tac att        4674
Val Ile Tyr Thr Ala Asp Ala Gln Lys Val His Val Gln Tyr Ile
    1505                1510                1515 gat ggt gaa act gac cag atg ctg cgt cag gat gat ttg gac ggc        4719
Asp Gly Glu Thr Asp Gln Met Leu Arg Gln Asp Asp Leu Asp Gly
    1520                1525                1530 tac acg gat gaa acg att cct tac agc acg gct gaa ggc atc aag        4764
Tyr Thr Asp Glu Thr Ile Pro Tyr Ser Thr Ala Glu Gly Ile Lys
    1535                1540                1545 aag ttt gaa ggc gac ggt tat gaa ctg ttc aag gac aac ttc cca        4809
Lys Phe Glu Gly Asp Gly Tyr Glu Leu Phe Lys Asp Asn Phe Pro
    1550                1555                1560 gct ggt gag aag ttc gat aac gat gac aag aat gac caa acc tac        4854
Ala Gly Glu Lys Phe Asp Asn Asp Asp Lys Asn Asp Gln Thr Tyr
    1565                1570                1575 acg gta atc ttc aag cac cat cgt gaa aac gtt gat cca aac cac        4899
Thr Val Ile Phe Lys His His Arg Glu Asn Val Asp Pro Asn His
    1580                1585                1590 tcc tcg gct gat ggc acg aag ggt acg aag acg ctg acg gaa acg        4944
Ser Ser Ala Asp Gly Thr Lys Gly Thr Lys Thr Leu Thr Glu Thr
    1595                1600                1605 gtt cac tac aag tac gca gat ggt acc aag gcc gct gaa gat cag        4989
Val His Tyr Lys Tyr Ala Asp Gly Thr Lys Ala Ala Glu Asp Gln
    1610                1615                1620 acg gct cag gta acg ttt acg cgg aac ggt gtc ctg gat gac gtt        5034
Thr Ala Gln Val Thr Phe Thr Arg Asn Gly Val Leu Asp Asp Val
    1625                1630                1635 acg ggt atc gtg gcc tgg ggc aag tgg aac gaa gcc agc cag agc        5079
Thr Gly Ile Val Ala Trp Gly Lys Trp Asn Glu Ala Ser Gln Ser
    1640                1645                1650 tac aag gct ttg act tca cca acg att gcc ggc tac acg cca agc        5124
Tyr Lys Ala Leu Thr Ser Pro Thr Ile Ala Gly Tyr Thr Pro Ser
    1655                1660                1665 gaa gcg gtg gta aag cgc agt tcc aac agc gat gcc gaa caa ggc        5169
Glu Ala Val Val Lys Arg Ser Ser Asn Ser Asp Ala Glu Gln Gly
    1670                1675                1680 cca acg ctt acg gtc atc tac acg gct gat gcc caa aag gtt cac        5214
Pro Thr Leu Thr Val Ile Tyr Thr Ala Asp Ala Gln Lys Val His
    1685                1690                1695 gtt caa tac att gat ggt gaa act gac cag atg ctg cgt cag gat        5259
```

```
Val Gln Tyr Ile Asp Gly Glu Thr Asp Gln Met Leu Arg Gln Asp
    1700            1705                1710 gat ttg gac ggc tac acg gat gaa acg att cct tac agc acg gct      5304
Asp Leu Asp Gly Tyr Thr Asp Glu Thr Ile Pro Tyr Ser Thr Ala
1715            1720                1725 gaa ggc atc aag aag ttt gaa ggc gac ggt tat gaa ctg ttc aag      5349
Glu Gly Ile Lys Lys Phe Glu Gly Asp Gly Tyr Glu Leu Phe Lys
1730            1735                1740 gac aac ttc cca gct ggt gag aag ttc gat aac gat gac acc aac      5394
Asp Asn Phe Pro Ala Gly Glu Lys Phe Asp Asn Asp Asp Thr Asn
1745            1750                1755 gat caa ttc tac acg gta atc ttc aag cac cat cgt gaa aac gtt      5439
Asp Gln Phe Tyr Thr Val Ile Phe Lys His His Arg Glu Asn Val
1760            1765                1770 gat cca aac cac tcc tcg gct gat ggc acg aag ggt acg aag acg      5484
Asp Pro Asn His Ser Ser Ala Asp Gly Thr Lys Gly Thr Lys Thr
1775            1780                1785 ctg acg gaa acg gtt cac tac aag tac gct aat ggc acc aag gcg      5529
Leu Thr Glu Thr Val His Tyr Lys Tyr Ala Asn Gly Thr Lys Ala
1790            1795                1800 gct gaa gat cag acg gct cag gta acg ttt acg cgg aac ggt gtc      5574
Ala Glu Asp Gln Thr Ala Gln Val Thr Phe Thr Arg Asn Gly Val
1805            1810                1815 ctg gat gac gtt acg ggt atc gtg gcc tgg ggc aag tgg aac gaa      5619
Leu Asp Asp Val Thr Gly Ile Val Ala Trp Gly Lys Trp Asn Glu
1820            1825                1830 gcc agc cag agc tac aag gct ttg act tca cca acg att gcc ggc      5664
Ala Ser Gln Ser Tyr Lys Ala Leu Thr Ser Pro Thr Ile Ala Gly
1835            1840                1845 tac gcg cca agc gaa gcg gtg gta aag cgc agt tcc aac agc gat      5709
Tyr Ala Pro Ser Glu Ala Val Val Lys Arg Ser Ser Asn Ser Asp
1850            1855                1860 gcc gaa caa ggc cca acg ctt acg gtc att tac acg gct gat gcc      5754
Ala Glu Gln Gly Pro Thr Leu Thr Val Ile Tyr Thr Ala Asp Ala
1865            1870                1875 caa aag gtt cac gtt caa tac att gat ggt gaa act gac cag atg      5799
Gln Lys Val His Val Gln Tyr Ile Asp Gly Glu Thr Asp Gln Met
1880            1885                1890 ctg cgt cag gat gat ttg gac ggc tac acg gat gaa acg att cct      5844
Leu Arg Gln Asp Asp Leu Asp Gly Tyr Thr Asp Glu Thr Ile Pro
1895            1900                1905 tac agc acg gct gaa ggc atc aag aag ttt gaa ggc gac ggt tat      5889
Tyr Ser Thr Ala Glu Gly Ile Lys Lys Phe Glu Gly Asp Gly Tyr
1910            1915                1920 gaa ctg ttc aag gac aac ttc cca gct ggt gag aag ttc gat aac      5934
Glu Leu Phe Lys Asp Asn Phe Pro Ala Gly Glu Lys Phe Asp Asn
1925            1930                1935 gat gac aag aat gac caa acc tac acg gta atc ttc aag cac cat      5979
Asp Asp Lys Asn Asp Gln Thr Tyr Thr Val Ile Phe Lys His His
1940            1945                1950 cgt gaa aac gtt gat cca aac cac tcc tcg gct gat ggc acg aag      6024
Arg Glu Asn Val Asp Pro Asn His Ser Ser Ala Asp Gly Thr Lys
1955            1960                1965 ggt acg aag acg ctg acg gaa acg gtt cac tac aag tac gca gat      6069
Gly Thr Lys Thr Leu Thr Glu Thr Val His Tyr Lys Tyr Ala Asp
1970            1975                1980 ggt acc aag gcc gct gaa gat cag acg gct cag gta acg ttt acg      6114
Gly Thr Lys Ala Ala Glu Asp Gln Thr Ala Gln Val Thr Phe Thr
1985            1990                1995
```

```
cgg aac ggt gtc ctg gat gac gtt acg ggt atc gtg gcc tgg ggc    6159
Arg Asn Gly Val Leu Asp Asp Val Thr Gly Ile Val Ala Trp Gly
    2000            2005            2010 aag tgg aac gaa gcc agc cag agc tac aag gct ttg act tca cca    6204
Lys Trp Asn Glu Ala Ser Gln Ser Tyr Lys Ala Leu Thr Ser Pro
    2015            2020            2025 acg att gcc ggc tac acg cca agc gaa gcg gtg gta aag cgc agt    6249
Thr Ile Ala Gly Tyr Thr Pro Ser Glu Ala Val Val Lys Arg Ser
    2030            2035            2040 tcc aac agc gat gcc gaa caa ggc cca acg ctt acg gtc atc tac    6294
Ser Asn Ser Asp Ala Glu Gln Gly Pro Thr Leu Thr Val Ile Tyr
    2045            2050            2055 acg gct gat gcc caa aag gtt cac gtt caa tac att gat ggt gaa    6339
Thr Ala Asp Ala Gln Lys Val His Val Gln Tyr Ile Asp Gly Glu
    2060            2065            2070 act gac cag atg ctg cgt cag gat gat ttg gac ggc tac acg gat    6384
Thr Asp Gln Met Leu Arg Gln Asp Asp Leu Asp Gly Tyr Thr Asp
    2075            2080            2085 gaa acg att cct tac agc acg gct gaa ggc atc aag aag ttt gaa    6429
Glu Thr Ile Pro Tyr Ser Thr Ala Glu Gly Ile Lys Lys Phe Glu
    2090            2095            2100 ggc gac ggt tat gaa ctg ttc aag gac aac ttc cca gct ggt gag    6474
Gly Asp Gly Tyr Glu Leu Phe Lys Asp Asn Phe Pro Ala Gly Glu
    2105            2110            2115 aag ttc gat aac gat gac acc aac gat caa ttc tac acg gta atc    6519
Lys Phe Asp Asn Asp Asp Thr Asn Asp Gln Phe Tyr Thr Val Ile
    2120            2125            2130 ttc aag cac cat cgt gaa aac gtt gat cca aac cac tcc tcg gct    6564
Phe Lys His His Arg Glu Asn Val Asp Pro Asn His Ser Ser Ala
    2135            2140            2145 gat ggc acg aag ggt acg aag acg ctg acg gaa acg gtt cac tac    6609
Asp Gly Thr Lys Gly Thr Lys Thr Leu Thr Glu Thr Val His Tyr
    2150            2155            2160 aag tac gct aat ggc acc aag gcg gct gaa gat cag acg gct cag    6654
Lys Tyr Ala Asn Gly Thr Lys Ala Ala Glu Asp Gln Thr Ala Gln
    2165            2170            2175 gta acg ttt acg cgg aac ggt gtc ctg gat gac gtt acg ggt atc    6699
Val Thr Phe Thr Arg Asn Gly Val Leu Asp Asp Val Thr Gly Ile
    2180            2185            2190 gtg gcc tgg ggc aag tgg aac gaa gcc agc cag agc tac aag gct    6744
Val Ala Trp Gly Lys Trp Asn Glu Ala Ser Gln Ser Tyr Lys Ala
    2195            2200            2205 ttg act tca cca acg att gcc ggc tac gcg cca agc gaa gcg gtg    6789
Leu Thr Ser Pro Thr Ile Ala Gly Tyr Ala Pro Ser Glu Ala Val
    2210            2215            2220 gta aag cgc agt tcc aac agc gat gcc gaa caa ggc cca acg ctt    6834
Val Lys Arg Ser Ser Asn Ser Asp Ala Glu Gln Gly Pro Thr Leu
    2225            2230            2235 acg gtc atc tac acg gct gat gcc caa aag gtt cac gtt caa tac    6879
Thr Val Ile Tyr Thr Ala Asp Ala Gln Lys Val His Val Gln Tyr
    2240            2245            2250 att gat ggt gaa act gac cag atg ctg cgt cag gat gat ttg gac    6924
Ile Asp Gly Glu Thr Asp Gln Met Leu Arg Gln Asp Asp Leu Asp
    2255            2260            2265 ggc tac acg gat gaa acg att cct tac agc acg gct gaa ggc atc    6969
Gly Tyr Thr Asp Glu Thr Ile Pro Tyr Ser Thr Ala Glu Gly Ile
    2270            2275            2280 aag aag ttt gaa ggc gac ggt tat gaa ctg ttc aag gac aac ttc    7014
Lys Lys Phe Glu Gly Asp Gly Tyr Glu Leu Phe Lys Asp Asn Phe
    2285            2290            2295
```

-continued

```
cca gct ggt gag aag ttc gat aac gat gac aag aat gac caa acc      7059
Pro Ala Gly Glu Lys Phe Asp Asn Asp Asp Lys Asn Asp Gln Thr
    2300                2305                2310 tac acg gta atc ttc aag cac cat cgt gaa aac gtt gat cca aac      7104
Tyr Thr Val Ile Phe Lys His His Arg Glu Asn Val Asp Pro Asn
    2315                2320                2325 cac tcc tcg gct gat ggc acg aag ggt acg aag acg ctg acg gaa      7149
His Ser Ser Ala Asp Gly Thr Lys Gly Thr Lys Thr Leu Thr Glu
    2330                2335                2340 acg gtt cac tac aag tac gca gat ggt acc aag gcc gct gaa gat      7194
Thr Val His Tyr Lys Tyr Ala Asp Gly Thr Lys Ala Ala Glu Asp
    2345                2350                2355 cag acg gct cag gta acg ttt acg cgg aac ggt gtc ctg gat gac      7239
Gln Thr Ala Gln Val Thr Phe Thr Arg Asn Gly Val Leu Asp Asp
    2360                2365                2370 gtt acg ggt atc gtg gcc tgg ggc aag tgg aac gaa gcc agc cag      7284
Val Thr Gly Ile Val Ala Trp Gly Lys Trp Asn Glu Ala Ser Gln
    2375                2380                2385 agc tac aag gct ttg act tca cca acg att gcc ggc tac acg cca      7329
Ser Tyr Lys Ala Leu Thr Ser Pro Thr Ile Ala Gly Tyr Thr Pro
    2390                2395                2400 agc gaa gcg gtg gta aag cgc agt tcc aac agc gat gcc gaa caa      7374
Ser Glu Ala Val Val Lys Arg Ser Ser Asn Ser Asp Ala Glu Gln
    2405                2410                2415 ggc cca acg ctt acg gtc atc tac acg gct gat gcc caa aag gtt      7419
Gly Pro Thr Leu Thr Val Ile Tyr Thr Ala Asp Ala Gln Lys Val
    2420                2425                2430 cac gtt caa tac att gat ggt gaa act gac cag atg ctg cgt cag      7464
His Val Gln Tyr Ile Asp Gly Glu Thr Asp Gln Met Leu Arg Gln
    2435                2440                2445 gat gat ttg gac ggc tac acg gat gaa acg att cct tac agc acg      7509
Asp Asp Leu Asp Gly Tyr Thr Asp Glu Thr Ile Pro Tyr Ser Thr
    2450                2455                2460 gct gaa ggc atc aag aag ttt gaa ggc gac ggt tat gaa ctg ttc      7554
Ala Glu Gly Ile Lys Lys Phe Glu Gly Asp Gly Tyr Glu Leu Phe
    2465                2470                2475 aag gac aac ttc cca gct ggt gag aag ttc gac aac gat gac aag      7599
Lys Asp Asn Phe Pro Ala Gly Glu Lys Phe Asp Asn Asp Asp Lys
    2480                2485                2490 act gac caa acc tac acg gta atc ttc aag cac cat cgt gaa aac      7644
Thr Asp Gln Thr Tyr Thr Val Ile Phe Lys His His Arg Glu Asn
    2495                2500                2505 gtt gat cca aac cac tcc tcg gct gac ggc acg aaa ggt acg aag      7689
Val Asp Pro Asn His Ser Ser Ala Asp Gly Thr Lys Gly Thr Lys
    2510                2515                2520 acg ctg acg gaa acg gtt cac tac aag tac gca gat ggt acc aag      7734
Thr Leu Thr Glu Thr Val His Tyr Lys Tyr Ala Asp Gly Thr Lys
    2525                2530                2535 gcc gct gaa gat cag acg gct cag gta acg ttt acg cgg aac ggt      7779
Ala Ala Glu Asp Gln Thr Ala Gln Val Thr Phe Thr Arg Asn Gly
    2540                2545                2550 gtc ctg gat gac gtt acg ggt atc gtg gcc tgg ggc aag tgg aac      7824
Val Leu Asp Asp Val Thr Gly Ile Val Ala Trp Gly Lys Trp Asn
    2555                2560                2565 gaa gcc agc caa agc tac aag gct ctg act tca cca acg att gcc      7869
Glu Ala Ser Gln Ser Tyr Lys Ala Leu Thr Ser Pro Thr Ile Ala
    2570                2575                2580 ggc tac acg cca agt gaa gcg gta gta aag cgc agt tcc aac agc      7914
Gly Tyr Thr Pro Ser Glu Ala Val Val Lys Arg Ser Ser Asn Ser
```

```
                2585                2590                2595
gat gcc gaa caa ggc cca acg ctt acg gtc atc tac acg gct gat    7959
Asp Ala Glu Gln Gly Pro Thr Leu Thr Val Ile Tyr Thr Ala Asp
        2600                2605                2610 gcc caa aca gcc tac gtc aag tac gtt gat gac act ggc gag        8004
Ala Gln Thr Ala Tyr Val Lys Tyr Val Asp Asp Thr Thr Gly Glu
        2615                2620                2625 acg ctg cgt caa gac gat ctg cac ggc tac acg gat gaa acg att    8049
Thr Leu Arg Gln Asp Asp Leu His Gly Tyr Thr Asp Glu Thr Ile
        2630                2635                2640 cct tac agc acg gct gaa ggc atc aag aag ttt gaa ggc gac ggt    8094
Pro Tyr Ser Thr Ala Glu Gly Ile Lys Lys Phe Glu Gly Asp Gly
        2645                2650                2655 tat gaa ctg ttc aag gac aac ttc cca gct ggt gag aag ttc gac    8139
Tyr Glu Leu Phe Lys Asp Asn Phe Pro Ala Gly Glu Lys Phe Asp
        2660                2665                2670 aac gat gac aag act gac caa acc tac acg gta atc ttc aag cac    8184
Asn Asp Asp Lys Thr Asp Gln Thr Tyr Thr Val Ile Phe Lys His
        2675                2680                2685 cat cgt gaa aac gtt gat cca aac cac tcc tcg gct gac ggc acg    8229
His Arg Glu Asn Val Asp Pro Asn His Ser Ser Ala Asp Gly Thr
        2690                2695                2700 aaa ggt acg aag acg ctg acg gaa acg gtt cac tac aag tac gca    8274
Lys Gly Thr Lys Thr Leu Thr Glu Thr Val His Tyr Lys Tyr Ala
        2705                2710                2715 gat ggt acc aag gcc gct gaa gat cag acg gct cag gta acg ttt    8319
Asp Gly Thr Lys Ala Ala Glu Asp Gln Thr Ala Gln Val Thr Phe
        2720                2725                2730 acg cgg aac ggt gtc ctg gat gac gtt acg ggt atc gtg gcc tgg    8364
Thr Arg Asn Gly Val Leu Asp Asp Val Thr Gly Ile Val Ala Trp
        2735                2740                2745 ggc aag tgg aac gaa gcc agc caa agc tac aag gct ctg act tca    8409
Gly Lys Trp Asn Glu Ala Ser Gln Ser Tyr Lys Ala Leu Thr Ser
        2750                2755                2760 cca acg att gcc ggc tac acg cca agt gaa gcg gta gta aag cgc    8454
Pro Thr Ile Ala Gly Tyr Thr Pro Ser Glu Ala Val Val Lys Arg
        2765                2770                2775 agt tcc aac agc gat gcc gaa caa ggc cca acg ctt acg gtc atc    8499
Ser Ser Asn Ser Asp Ala Glu Gln Gly Pro Thr Leu Thr Val Ile
        2780                2785                2790 tac acg gct gat gcc caa aca gcc tac gtc aag tac gtt gat gac    8544
Tyr Thr Ala Asp Ala Gln Thr Ala Tyr Val Lys Tyr Val Asp Asp
        2795                2800                2805 acg act ggc gag acg ctg cgt caa gac gat ctg cac ggc tac acg    8589
Thr Thr Gly Glu Thr Leu Arg Gln Asp Asp Leu His Gly Tyr Thr
        2810                2815                2820 gat gaa acg att cca tac agc acg gct gaa ggc atc aag aag tac    8634
Asp Glu Thr Ile Pro Tyr Ser Thr Ala Glu Gly Ile Lys Lys Tyr
        2825                2830                2835 gaa ggc gac ggc tac gtt ctg gta tcg gac ggc ttt aag cca ggt    8679
Glu Gly Asp Gly Tyr Val Leu Val Ser Asp Gly Phe Lys Pro Gly
        2840                2845                2850 act aag ttc ggt gtt ggc acg cca acc tat gaa gtt cac ttc aag    8724
Thr Lys Phe Gly Val Gly Thr Pro Thr Tyr Glu Val His Phe Lys
        2855                2860                2865 cat ggc atg acg cat acc gat gca acc gac aag aat gct gaa caa    8769
His Gly Met Thr His Thr Asp Ala Thr Asp Lys Asn Ala Glu Gln
        2870                2875                2880 aag acg gtt acg gaa acg att cac tac gtt gac gaa aac aac caa    8814
```

-continued

| | | | | | | | | | | | | |
|---|---|---|---|---|---|---|---|---|---|---|---|---|
| Lys | Thr | Val | Thr | Glu | Thr | Ile | His | Tyr | Val | Asp | Glu | Asn Asn Gln |
| | 2885 | | | | 2890 | | | | 2895 | | | |

```
acc gtt cag cca gac tcc acg aca gca gta acc ttc aag cgc ggc      8859
Thr Val Gln Pro Asp Ser Thr Thr Ala Val Thr Phe Lys Arg Gly
    2900            2905            2910 tac acg acc gat aac gtt acc ggc aag gtt gtt tcc tac gat cca      8904
Tyr Thr Thr Asp Asn Val Thr Gly Lys Val Val Ser Tyr Asp Pro
    2915            2920            2925 tgg acg gtt gat ggt aat cag gct gac agt aag aca ttt gct gcc      8949
Trp Thr Val Asp Gly Asn Gln Ala Asp Ser Lys Thr Phe Ala Ala
    2930            2935            2940 gta cct agc cca gca gtc gaa ggt tac acg cca aac cac cag caa      8994
Val Pro Ser Pro Ala Val Glu Gly Tyr Thr Pro Asn His Gln Gln
    2945            2950            2955 att aac gaa ttc acc gtt acg cca gat tca aaa gac att gtc aag      9039
Ile Asn Glu Phe Thr Val Thr Pro Asp Ser Lys Asp Ile Val Lys
    2960            2965            2970 acg gtc gtt tat gtt ggt gat ccc caa gaa gct caa gcc atc ttc      9084
Thr Val Val Tyr Val Gly Asp Pro Gln Glu Ala Gln Ala Ile Phe
    2975            2980            2985 tat gat gaa aca acg ggc aag gaa atc agc aac acg cgt gaa atc      9129
Tyr Asp Glu Thr Thr Gly Lys Glu Ile Ser Asn Thr Arg Glu Ile
    2990            2995            3000 gta aat ggc aag act gat gaa acg atc ggc ttt acc aag gat cca      9174
Val Asn Gly Lys Thr Asp Glu Thr Ile Gly Phe Thr Lys Asp Pro
    3005            3010            3015 aat gaa gtc gtc aag gaa ctc gaa aag caa ggt tat gtc ttt gat      9219
Asn Glu Val Val Lys Glu Leu Glu Lys Gln Gly Tyr Val Phe Asp
    3020            3025            3030 aag gac aat gct aat aac aat gtc ttt gct gcc ggc acg acc tac      9264
Lys Asp Asn Ala Asn Asn Asn Val Phe Ala Ala Gly Thr Thr Tyr
    3035            3040            3045 gac aag aat tct gaa gtt cac caa tac ttc aag tac tac ttc acg      9309
Asp Lys Asn Ser Glu Val His Gln Tyr Phe Lys Tyr Tyr Phe Thr
    3050            3055            3060 cac gct acg acg atc gtt acg cca gac aat cca aag acg ccg gct      9354
His Ala Thr Thr Ile Val Thr Pro Asp Asn Pro Lys Thr Pro Ala
    3065            3070            3075 gat gta ttg ccg gac aac cct ggc aag aat tac ccg agc ggt gtt      9399
Asp Val Leu Pro Asp Asn Pro Gly Lys Asn Tyr Pro Ser Gly Val
    3080            3085            3090 gcc aag gat gat ctg aac aag acc gtt acg cgg acg atc aac att      9444
Ala Lys Asp Asp Leu Asn Lys Thr Val Thr Arg Thr Ile Asn Ile
    3095            3100            3105 acg acg cca gat ggc aag aca cag acg atc acg cag aag gct gaa      9489
Thr Thr Pro Asp Gly Lys Thr Gln Thr Ile Thr Gln Lys Ala Glu
    3110            3115            3120 ttt acg cgg agt gca acg gtt gat gag gtt acc ggt gaa gta act      9534
Phe Thr Arg Ser Ala Thr Val Asp Glu Val Thr Gly Glu Val Thr
    3125            3130            3135 tat gga cca tgg tcg aag aat gtc gtt ttg gaa agc gtt gac gta      9579
Tyr Gly Pro Trp Ser Lys Asn Val Val Leu Glu Ser Val Asp Val
    3140            3145            3150 cca aac att tct gga tac gtg cca tct gca tcc gtt cca gaa att      9624
Pro Asn Ile Ser Gly Tyr Val Pro Ser Ala Ser Val Pro Glu Ile
    3155            3160            3165 acg gtt acg cca aat gat caa gac atg acg atc aac atc acc tac      9669
Thr Val Thr Pro Asn Asp Gln Asp Met Thr Ile Asn Ile Thr Tyr
    3170            3175            3180
```

-continued

```
aag aag ctt gat tct ggc aag gca gct gac caa ggc ggt aat gct       9714
Lys Lys Leu Asp Ser Gly Lys Ala Ala Asp Gln Gly Gly Asn Ala
3185            3190                3195 tcc aat ggt ggt caa gca acg aat ggc ggt tca acg act ggt caa       9759
Ser Asn Gly Gly Gln Ala Thr Asn Gly Gly Ser Thr Thr Gly Gln
    3200            3205                3210 tcc gct caa aac ggc cag tca ggt caa acc caa aac aat gct ggt       9804
Ser Ala Gln Asn Gly Gln Ser Gly Gln Thr Gln Asn Asn Ala Gly
3215            3220                3225 gct caa caa ttg cca caa act ggt aac gcc aac aat gaa aag ggc       9849
Ala Gln Gln Leu Pro Gln Thr Gly Asn Ala Asn Asn Glu Lys Gly
    3230            3235                3240 gca ctg gga ttg gca agc gca atg ttc gcc gct ggt ctt ggc ctg       9894
Ala Leu Gly Leu Ala Ser Ala Met Phe Ala Ala Gly Leu Gly Leu
3245            3250                3255 ggc ttt ggc tca aag aag aag tgt cac gaa gac tagatgaaac            9937
Gly Phe Gly Ser Lys Lys Lys Cys His Glu Asp
    3260            3265 aataaaatag attcatcaca gataaaaaag actcaacctt tgattttca aaggttgagc  9997 cttttttgtct tttttcgcaa aga                                       10020

<210> SEQ ID NO 18
<211> LENGTH: 3269
<212> TYPE: PRT
<213> ORGANISM: Lactobacillus reuteri

<400> SEQUENCE: 18

Met Val Gly Lys Asn Asn Tyr Val Arg Glu Ser Lys Ser Asn Glu
1               5                   10                  15

His Phe Gln Arg Phe Ala Leu Arg Lys Leu Ser Val Gly Val Val Ser
            20                  25                  30

Val Ala Val Ala Ala Gly Phe Tyr Leu Gly Ser Gly Ala Thr Ala Gln
        35                  40                  45

Ala Ala Thr Thr Glu Ser Asn Ala Ser Ala Lys Thr Glu Gln Val Val
    50                  55                  60

Gln Gln Asn Ser Thr Ser Ala Ala Ser Asp Ser Thr Ser Thr Ser Asn
65                  70                  75                  80

Ser Ser Ala Ala Val Ser Thr Ser Ser Ala Thr Pro Val Ser Thr Glu
                85                  90                  95

Ser Ala Ser Ser Met Thr Val Ser Asp Leu Pro Ala Ser Ala Ser Ala
            100                 105                 110

Ala Ser Asp Asn Gln Ala Ser Ala Ala Asn Ala Ser Glu Ser Ser Ser
        115                 120                 125

Gln Ser Ala Ser Ser Val Ala Ser Asp Ala Ala Thr Val Ser
    130                 135                 140

Lys Asp Ser Gln Ala Ala Ser Glu Ala Asn Ser Gln Ser Ala Ala Asp
145                 150                 155                 160

Val Glu Thr Val Gln Leu Pro Thr Ser Ala Ala Asn Ala Asn Ala Asn
                165                 170                 175

Glu Ser Gln Ala Ala Asn Ile Leu Gly Ala Gln Ala Val Gln Lys Ala
            180                 185                 190

Ala Asn Gln Gln Ala Pro Ala Gly Phe Thr Val Thr Asp Pro Asn Tyr
        195                 200                 205

Pro Ala Glu Met Tyr Lys Asp Pro Asp Ala Ser His Tyr Thr Tyr Trp
    210                 215                 220

Trp Ala Gln Ser Ser Asn Gly Glu Tyr Asn Leu Val Leu Ser Thr Asp
```

-continued

```
               225                 230                 235                 240
Arg Asn Gly Asp Gly Lys Val Tyr Val Phe Leu Leu Gly Asn Asn Asn
                245                 250                 255
Asn Val Leu Gly Lys Tyr Thr Val Asp Lys Asn Lys Ser Thr Glu Val
                260                 265                 270
Ala Thr Asp Asp Glu Gly Asp Phe Gly Thr Val Tyr Asn Asp Gly Gln
                275                 280                 285
Ser Gly Val Phe Val Thr Ser Asp Gly Thr Trp Lys Ser Lys Phe Asn
        290                 295                 300
Val Phe Asp Pro Lys Ala Gly Glu Asp Gly Asp Tyr Gly Ser Ile
305                 310                 315                 320
Ser Phe Met Ile Pro Gln Val Glu Thr Gln Thr Thr Tyr Val Thr
                325                 330                 335
Tyr Phe Asp Ser Lys Gly Asn Lys Val Asp Lys Pro Ile Glu Val Ser
                340                 345                 350
Asp Pro Val Ile Gln Lys Gly Leu Asp Gly Gln Ile Tyr Thr Thr Lys
                355                 360                 365
Gly Gly Lys Val Ile Asn Gly Tyr Phe Ala Lys Glu Pro Lys Asn Ala
        370                 375                 380
His Gly Phe Met Ser Pro Phe Gly Lys Gln Gly Ala Ile Tyr Thr Lys
385                 390                 395                 400
Asp Trp His Asp Gly Leu Lys Ala Thr Phe Thr Glu Thr Asp Thr Lys
                405                 410                 415
Thr Gly Leu Met His Val Val Lys His Tyr Tyr His Ser Trp Gly
                420                 425                 430
Trp Gly Thr Trp Arg Thr Val Lys Glu Phe Asp Leu Ala Pro Gly Gln
        435                 440                 445
Ser Glu Lys Val Asp Tyr Asp Val Tyr Lys Ser Val Thr Ile His Ser
        450                 455                 460
Ile Tyr Ile Pro Gln Thr Ile Asn Ile Gln Tyr Thr Tyr Glu Lys Leu
465                 470                 475                 480
Gly Asn Leu Val Ile Ser Ser Asp Ser Lys Ser Phe Pro Ala Glu Asp
                485                 490                 495
Lys Thr Gln Tyr Pro Asn Asp Lys Ser Asp Ser Thr Lys Ala Gly Asn
                500                 505                 510
Val Thr Ile Pro Lys Val Ala Gly Phe Thr Pro Thr Ile Asn Asp Lys
                515                 520                 525
Thr Val Thr Asn Tyr Thr Phe Asn Pro Ser Asp Tyr Val Ser Asp Leu
                530                 535                 540
Ser Lys Asp Ile Asn Val Val Tyr Val Ala Asp Thr Gln Glu Ala Ala
545                 550                 555                 560
Ile Ser Phe Tyr Asp Glu Thr Asp His Lys Pro Leu Asn Asp Gln Thr
                565                 570                 575
Ile Gln Leu Thr Gly Lys Thr Gly Glu Lys Ile Ser His Thr Glu Ala
                580                 585                 590
Asn Gln Thr Leu Ala Lys Leu Gly Lys Gln Gly Tyr Val Val Asp Gln
        595                 600                 605
Asn Thr Phe Ala Asp Asp Ala Thr Tyr Asp Asn Asp Thr Gln Ala Pro
        610                 615                 620
Gln Glu Phe Thr Ile Tyr Leu Lys His Asp Thr Thr His Thr Asp Ala
625                 630                 635                 640
Thr Ser Ser Lys Ala Asp Gln Lys Thr Val Ser Glu Thr Ile His Tyr
                645                 650                 655
```

-continued

Val Tyr Lys Asp Gly Val Asn Ala Asn Lys Pro Val Ala Asp Asp Ala
            660                 665                 670

Asn Thr Thr Val Thr Phe Lys Arg Gly Tyr Thr Thr Asp Lys Val Thr
        675                 680                 685

Gly Lys Ile Val Ser Tyr Asp Pro Trp Thr Val Asp Gly Lys Gln Ala
690                 695                 700

Asp Ser Lys Thr Phe Asp Ala Val Lys Ser Pro Val Ile Ala Gly Tyr
705                 710                 715                 720

Thr Ala Asp Gln Ala Glu Val Ala Ala Gln Thr Val Thr Pro Asp Ser
            725                 730                 735

Gln Asn Ile Asn Lys Thr Val Tyr Tyr Thr Ala Asp Thr Gln Glu Ala
                740                 745                 750

Ala Ile Asn Phe Tyr Asp Glu Thr Gly His Lys Leu Leu Asp Asn Gln
            755                 760                 765

Thr Ile His Leu Thr Gly Lys Thr Gly Glu Lys Val Asp Arg Thr Gln
    770                 775                 780

Ala Asp Gln Thr Leu Ala Asp Leu Val Lys Gln Gly Tyr Val Leu Asp
785                 790                 795                 800

Lys Glu Asn Thr Ala Lys Ala Phe Pro Ala Asp Ala Val Tyr Asp Asn
                805                 810                 815

Asn Asp Gln Thr Pro Gln Glu Phe Thr Ile Tyr Leu Lys His Gly Thr
            820                 825                 830

Thr His Thr Asp Ala Thr Ser Ser Lys Ala Asp Gln Lys Thr Val Ser
    835                 840                 845

Glu Thr Ile His Tyr Val Tyr Lys Asp Gly Val Asn Ala Asn Lys Pro
850                 855                 860

Val Ala Asp Asp Ala Asn Thr Thr Val Thr Phe Lys Arg Gly Tyr Thr
865                 870                 875                 880

Thr Asp Lys Val Thr Gly Lys Ile Val Ser Tyr Asp Pro Trp Thr Val
                885                 890                 895

Asp Gly Lys Gln Ala Asp Ser Lys Thr Phe Asp Ala Val Lys Ser Pro
            900                 905                 910

Val Ile Ala Gly Tyr Thr Ala Asp Gln Ala Glu Val Ala Ala Gln Thr
    915                 920                 925

Val Thr Pro Asp Ser Gln Asn Ile Asn Lys Thr Val Tyr Tyr Thr Ala
930                 935                 940

Asp Thr Gln Glu Ala Ala Ile Asn Phe Tyr Asp Glu Thr Gly His Lys
945                 950                 955                 960

Leu Leu Asp Asn Gln Thr Ile His Leu Thr Gly Lys Thr Gly Glu Lys
                965                 970                 975

Val Asp Arg Thr Gln Ala Asp Thr Leu Ala Glu Leu Glu Lys Gln
            980                 985                 990

Gly Tyr Val Leu Asp Glu Asn Asn Thr Lys Leu Gly Phe Pro Ser Asn
    995                 1000                1005

Ala Ala Tyr Asp Asp Asp Val Lys Pro Gln Glu Phe Thr Ile
        1010                1015                1020

Tyr Leu Lys His Gly Met Thr His Thr Asp Ala Thr Asp Lys Asn
    1025                1030                1035

Ala Glu Gln Lys Ile Val Thr Glu Thr Ile His Tyr Val Tyr Glu
        1040                1045                1050

Asn Asn Gln Thr Ala Lys Thr Asp Tyr Thr Ser Ala Val Asp Phe
    1055                1060                1065

```
Lys Arg Gly Tyr Thr Thr Asp Asn Val Thr His Lys Ile Ile Ser
1070            1075            1080

Tyr Asp Pro Trp Met Val Ser Ser Lys Lys Phe Gly Phe Val Lys
1085            1090            1095

Ser Pro Ala Ile Glu Gly Tyr Thr Pro Asn His Ser Gln Ile Asp
1100            1105            1110

Glu Ile Thr Val Thr Pro Asp Ser Lys Asp Val Val Lys Thr Val
1115            1120            1125

Val Tyr Val Gly Asn Ala Gln Glu Ala Gln Ala Ile Phe Tyr Asp
1130            1135            1140

Glu Thr Thr Gly Lys Glu Ile Ser Gly Thr Arg Glu Ile Ala Thr
1145            1150            1155

Gly Lys Thr Asp Glu Thr Ile Ser Phe Thr Lys Asp Pro Asn Glu
1160            1165            1170

Val Val Lys Glu Leu Glu Lys Gln Gly Tyr Val Phe Asp Lys Asp
1175            1180            1185

Asn Ala Lys Asn Asn Val Phe Val Ala Gly Thr Ala Tyr Asp Lys
1190            1195            1200

Asn Ser Glu Val His Gln Tyr Phe Lys Tyr Tyr Leu Lys His Gly
1205            1210            1215

His Ala Thr Val Thr Pro Asp Gln Asp Pro Gln Lys Gly Gln Lys
1220            1225            1230

Thr Val Thr Gln Thr Ile Lys Tyr Glu Tyr Ala Asp Gly Thr Ala
1235            1240            1245

Thr Gly Leu Ala Asp Asn Val Gln Thr Leu Thr Phe Lys Arg Thr
1250            1255            1260

Gly Asp Lys Asp Leu Val Thr His Glu Val Thr Trp Pro Asp Trp
1265            1270            1275

Ser Thr Val Ala Gly Gln Gln Thr Ser Val Val Thr Ser Pro Ala
1280            1285            1290

Leu Lys Gly Tyr Thr Ala Asp Thr Asn Glu Ile Pro Ala Ile Thr
1295            1300            1305

Tyr His Ala Gly Asp Ser Asp Val Thr Tyr Val Val Lys Tyr Asn
1310            1315            1320

Ala Asp Val Gln His Ala Val Ile Asn Tyr Ile Asp Gly Glu Ser
1325            1330            1335

Asp Glu Ile Leu His Thr Asp Lys Val Asn Gly His Ser Asp Glu
1340            1345            1350

Lys Ile Asn Tyr Ser Thr Ala Asp Met Ile Lys Gln Leu Glu Ala
1355            1360            1365

Lys Gly Tyr Glu Leu Phe Lys Asp Asn Phe Pro Ala Gly Glu Lys
1370            1375            1380

Phe Asp Asn Asp Thr Asn Asp Gln Phe Tyr Thr Val Ile Phe
1385            1390            1395

Lys His His Arg Glu Asn Val Asp Pro Asn His Ser Ser Ala Asp
1400            1405            1410

Gly Thr Lys Gly Thr Lys Thr Leu Thr Glu Thr Val His Tyr Lys
1415            1420            1425

Tyr Ala Asn Gly Thr Lys Ala Ala Glu Asp Gln Thr Ala Gln Val
1430            1435            1440

Thr Phe Thr Arg Asn Gly Val Leu Asp Asp Val Thr Gly Ile Val
1445            1450            1455

Ala Trp Gly Lys Trp Asn Glu Ala Ser Gln Ser Tyr Lys Ala Leu
```

```
                1460                1465                1470

Thr Ser Pro Thr Ile Ala Gly Tyr Ala Pro Ser Glu Ala Val Val
    1475                1480                1485

Lys Arg Ser Ser Asn Ser Asp Ala Glu Gln Gly Pro Thr Leu Thr
    1490                1495                1500

Val Ile Tyr Thr Ala Asp Ala Gln Lys Val His Val Gln Tyr Ile
    1505                1510                1515

Asp Gly Glu Thr Asp Gln Met Leu Arg Gln Asp Asp Leu Asp Gly
    1520                1525                1530

Tyr Thr Asp Glu Thr Ile Pro Tyr Ser Thr Ala Glu Gly Ile Lys
    1535                1540                1545

Lys Phe Glu Gly Asp Gly Tyr Glu Leu Phe Lys Asp Asn Phe Pro
    1550                1555                1560

Ala Gly Glu Lys Phe Asp Asn Asp Asp Lys Asn Asp Gln Thr Tyr
    1565                1570                1575

Thr Val Ile Phe Lys His His Arg Glu Asn Val Asp Pro Asn His
    1580                1585                1590

Ser Ser Ala Asp Gly Thr Lys Gly Thr Lys Thr Leu Thr Glu Thr
    1595                1600                1605

Val His Tyr Lys Tyr Ala Asp Gly Thr Lys Ala Ala Glu Asp Gln
    1610                1615                1620

Thr Ala Gln Val Thr Phe Thr Arg Asn Gly Val Leu Asp Asp Val
    1625                1630                1635

Thr Gly Ile Val Ala Trp Gly Lys Trp Asn Glu Ala Ser Gln Ser
    1640                1645                1650

Tyr Lys Ala Leu Thr Ser Pro Thr Ile Ala Gly Tyr Thr Pro Ser
    1655                1660                1665

Glu Ala Val Val Lys Arg Ser Ser Asn Ser Asp Ala Glu Gln Gly
    1670                1675                1680

Pro Thr Leu Thr Val Ile Tyr Thr Ala Asp Ala Gln Lys Val His
    1685                1690                1695

Val Gln Tyr Ile Asp Gly Glu Thr Asp Gln Met Leu Arg Gln Asp
    1700                1705                1710

Asp Leu Asp Gly Tyr Thr Asp Glu Thr Ile Pro Tyr Ser Thr Ala
    1715                1720                1725

Glu Gly Ile Lys Lys Phe Glu Gly Asp Gly Tyr Glu Leu Phe Lys
    1730                1735                1740

Asp Asn Phe Pro Ala Gly Glu Lys Phe Asp Asn Asp Asp Thr Asn
    1745                1750                1755

Asp Gln Phe Tyr Thr Val Ile Phe Lys His His Arg Glu Asn Val
    1760                1765                1770

Asp Pro Asn His Ser Ser Ala Asp Gly Thr Lys Gly Thr Lys Thr
    1775                1780                1785

Leu Thr Glu Thr Val His Tyr Lys Tyr Ala Asn Gly Thr Lys Ala
    1790                1795                1800

Ala Glu Asp Gln Thr Ala Gln Val Thr Phe Thr Arg Asn Gly Val
    1805                1810                1815

Leu Asp Asp Val Thr Gly Ile Val Ala Trp Gly Lys Trp Asn Glu
    1820                1825                1830

Ala Ser Gln Ser Tyr Lys Ala Leu Thr Ser Pro Thr Ile Ala Gly
    1835                1840                1845

Tyr Ala Pro Ser Glu Ala Val Val Lys Arg Ser Ser Asn Ser Asp
    1850                1855                1860
```

-continued

```
Ala Glu Gln Gly Pro Thr Leu Thr Val Ile Tyr Thr Ala Asp Ala
1865                 1870                1875

Gln Lys Val His Val Gln Tyr Ile Asp Gly Glu Thr Asp Gln Met
    1880                1885                1890

Leu Arg Gln Asp Asp Leu Asp Gly Tyr Thr Asp Glu Thr Ile Pro
    1895                1900                1905

Tyr Ser Thr Ala Glu Gly Ile Lys Lys Phe Glu Gly Asp Gly Tyr
    1910                1915                1920

Glu Leu Phe Lys Asp Asn Phe Pro Ala Gly Glu Lys Phe Asp Asn
1925                 1930                1935

Asp Asp Lys Asn Asp Gln Thr Tyr Thr Val Ile Phe Lys His His
1940                 1945                1950

Arg Glu Asn Val Asp Pro Asn His Ser Ser Ala Asp Gly Thr Lys
1955                 1960                1965

Gly Thr Lys Thr Leu Thr Glu Thr Val His Tyr Lys Tyr Ala Asp
1970                 1975                1980

Gly Thr Lys Ala Ala Glu Asp Gln Thr Ala Gln Val Thr Phe Thr
1985                 1990                1995

Arg Asn Gly Val Leu Asp Asp Val Thr Gly Ile Val Ala Trp Gly
2000                 2005                2010

Lys Trp Asn Glu Ala Ser Gln Ser Tyr Lys Ala Leu Thr Ser Pro
2015                 2020                2025

Thr Ile Ala Gly Tyr Thr Pro Ser Glu Ala Val Val Lys Arg Ser
2030                 2035                2040

Ser Asn Ser Asp Ala Glu Gln Gly Pro Thr Leu Thr Val Ile Tyr
2045                 2050                2055

Thr Ala Asp Ala Gln Lys Val His Val Gln Tyr Ile Asp Gly Glu
2060                 2065                2070

Thr Asp Gln Met Leu Arg Gln Asp Asp Leu Asp Gly Tyr Thr Asp
2075                 2080                2085

Glu Thr Ile Pro Tyr Ser Thr Ala Glu Gly Ile Lys Lys Phe Glu
2090                 2095                2100

Gly Asp Gly Tyr Glu Leu Phe Lys Asp Asn Phe Pro Ala Gly Glu
2105                 2110                2115

Lys Phe Asp Asn Asp Asp Thr Asn Asp Gln Phe Tyr Thr Val Ile
2120                 2125                2130

Phe Lys His His Arg Glu Asn Val Asp Pro Asn His Ser Ser Ala
2135                 2140                2145

Asp Gly Thr Lys Gly Thr Lys Thr Leu Thr Glu Thr Val His Tyr
2150                 2155                2160

Lys Tyr Ala Asn Gly Thr Lys Ala Ala Glu Asp Gln Thr Ala Gln
2165                 2170                2175

Val Thr Phe Thr Arg Asn Gly Val Leu Asp Asp Val Thr Gly Ile
2180                 2185                2190

Val Ala Trp Gly Lys Trp Asn Glu Ala Ser Gln Ser Tyr Lys Ala
2195                 2200                2205

Leu Thr Ser Pro Thr Ile Ala Gly Tyr Ala Pro Ser Glu Ala Val
2210                 2215                2220

Val Lys Arg Ser Ser Asn Ser Asp Ala Glu Gln Gly Pro Thr Leu
2225                 2230                2235

Thr Val Ile Tyr Thr Ala Asp Ala Gln Lys Val His Val Gln Tyr
2240                 2245                2250
```

```
Ile Asp Gly Glu Thr Asp Gln Met Leu Arg Gln Asp Asp Leu Asp
2255                2260                2265

Gly Tyr Thr Asp Glu Thr Ile Pro Tyr Ser Thr Ala Glu Gly Ile
2270                2275                2280

Lys Lys Phe Glu Gly Asp Gly Tyr Glu Leu Phe Lys Asp Asn Phe
2285                2290                2295

Pro Ala Gly Glu Lys Phe Asp Asn Asp Lys Asn Asp Gln Thr
2300                2305                2310

Tyr Thr Val Ile Phe Lys His His Arg Glu Asn Val Asp Pro Asn
2315                2320                2325

His Ser Ser Ala Asp Gly Thr Lys Gly Thr Lys Thr Leu Thr Glu
2330                2335                2340

Thr Val His Tyr Lys Tyr Ala Asp Gly Thr Lys Ala Ala Glu Asp
2345                2350                2355

Gln Thr Ala Gln Val Thr Phe Thr Arg Asn Gly Val Leu Asp Asp
2360                2365                2370

Val Thr Gly Ile Val Ala Trp Gly Lys Trp Asn Glu Ala Ser Gln
2375                2380                2385

Ser Tyr Lys Ala Leu Thr Ser Pro Thr Ile Ala Gly Tyr Thr Pro
2390                2395                2400

Ser Glu Ala Val Val Lys Arg Ser Ser Asn Ser Asp Ala Glu Gln
2405                2410                2415

Gly Pro Thr Leu Thr Val Ile Tyr Thr Ala Asp Ala Gln Lys Val
2420                2425                2430

His Val Gln Tyr Ile Asp Gly Glu Thr Asp Gln Met Leu Arg Gln
2435                2440                2445

Asp Asp Leu Asp Gly Tyr Thr Asp Glu Thr Ile Pro Tyr Ser Thr
2450                2455                2460

Ala Glu Gly Ile Lys Lys Phe Glu Gly Asp Gly Tyr Glu Leu Phe
2465                2470                2475

Lys Asp Asn Phe Pro Ala Gly Glu Lys Phe Asp Asn Asp Asp Lys
2480                2485                2490

Thr Asp Gln Thr Tyr Thr Val Ile Phe Lys His His Arg Glu Asn
2495                2500                2505

Val Asp Pro Asn His Ser Ser Ala Asp Gly Thr Lys Gly Thr Lys
2510                2515                2520

Thr Leu Thr Glu Thr Val His Tyr Lys Tyr Ala Asp Gly Thr Lys
2525                2530                2535

Ala Ala Glu Asp Gln Thr Ala Gln Val Thr Phe Thr Arg Asn Gly
2540                2545                2550

Val Leu Asp Asp Val Thr Gly Ile Val Ala Trp Gly Lys Trp Asn
2555                2560                2565

Glu Ala Ser Gln Ser Tyr Lys Ala Leu Thr Ser Pro Thr Ile Ala
2570                2575                2580

Gly Tyr Thr Pro Ser Glu Ala Val Val Lys Arg Ser Ser Asn Ser
2585                2590                2595

Asp Ala Glu Gln Gly Pro Thr Leu Thr Val Ile Tyr Thr Ala Asp
2600                2605                2610

Ala Gln Thr Ala Tyr Val Lys Tyr Val Asp Asp Thr Thr Gly Glu
2615                2620                2625

Thr Leu Arg Gln Asp Asp Leu His Gly Tyr Thr Asp Glu Thr Ile
2630                2635                2640

Pro Tyr Ser Thr Ala Glu Gly Ile Lys Lys Phe Glu Gly Asp Gly
```

```
              2645                2650                2655

Tyr Glu Leu Phe Lys Asp Asn Phe Pro Ala Gly Glu Lys Phe Asp
              2660                2665                2670

Asn Asp Asp Lys Thr Asp Gln Thr Tyr Thr Val Ile Phe Lys His
              2675                2680                2685

His Arg Glu Asn Val Asp Pro Asn His Ser Ser Ala Asp Gly Thr
              2690                2695                2700

Lys Gly Thr Lys Thr Leu Thr Glu Thr Val His Tyr Lys Tyr Ala
              2705                2710                2715

Asp Gly Thr Lys Ala Ala Glu Asp Gln Thr Ala Gln Val Thr Phe
              2720                2725                2730

Thr Arg Asn Gly Val Leu Asp Asp Val Thr Gly Ile Val Ala Trp
              2735                2740                2745

Gly Lys Trp Asn Glu Ala Ser Gln Ser Tyr Lys Ala Leu Thr Ser
              2750                2755                2760

Pro Thr Ile Ala Gly Tyr Thr Pro Ser Glu Ala Val Val Lys Arg
              2765                2770                2775

Ser Ser Asn Ser Asp Ala Glu Gln Gly Pro Thr Leu Thr Val Ile
              2780                2785                2790

Tyr Thr Ala Asp Ala Gln Thr Ala Tyr Val Lys Tyr Val Asp Asp
              2795                2800                2805

Thr Thr Gly Glu Thr Leu Arg Gln Asp Asp Leu His Gly Tyr Thr
              2810                2815                2820

Asp Glu Thr Ile Pro Tyr Ser Thr Ala Glu Gly Ile Lys Lys Tyr
              2825                2830                2835

Glu Gly Asp Gly Tyr Val Leu Val Ser Asp Gly Phe Lys Pro Gly
              2840                2845                2850

Thr Lys Phe Gly Val Gly Thr Pro Thr Tyr Glu Val His Phe Lys
              2855                2860                2865

His Gly Met Thr His Thr Asp Ala Thr Asp Lys Asn Ala Glu Gln
              2870                2875                2880

Lys Thr Val Thr Glu Thr Ile His Tyr Val Asp Glu Asn Asn Gln
              2885                2890                2895

Thr Val Gln Pro Asp Ser Thr Thr Ala Val Thr Phe Lys Arg Gly
              2900                2905                2910

Tyr Thr Thr Asp Asn Val Thr Gly Lys Val Val Ser Tyr Asp Pro
              2915                2920                2925

Trp Thr Val Asp Gly Asn Gln Ala Asp Ser Lys Thr Phe Ala Ala
              2930                2935                2940

Val Pro Ser Pro Ala Val Glu Gly Tyr Thr Pro Asn His Gln Gln
              2945                2950                2955

Ile Asn Glu Phe Thr Val Thr Pro Asp Ser Lys Asp Ile Val Lys
              2960                2965                2970

Thr Val Val Tyr Val Gly Asp Pro Gln Glu Ala Gln Ala Ile Phe
              2975                2980                2985

Tyr Asp Glu Thr Thr Gly Lys Glu Ile Ser Asn Thr Arg Glu Ile
              2990                2995                3000

Val Asn Gly Lys Thr Asp Glu Thr Ile Gly Phe Thr Lys Asp Pro
              3005                3010                3015

Asn Glu Val Val Lys Glu Leu Glu Lys Gln Gly Tyr Val Phe Asp
              3020                3025                3030

Lys Asp Asn Ala Asn Asn Asn Val Phe Ala Ala Gly Thr Thr Tyr
              3035                3040                3045
```

Asp Lys Asn Ser Glu Val His Gln Tyr Phe Lys Tyr Tyr Phe Thr
3050                3055                3060

His Ala Thr Thr Ile Val Thr Pro Asp Asn Pro Lys Thr Pro Ala
     3065                3070                3075

Asp Val Leu Pro Asp Asn Pro Gly Lys Asn Tyr Pro Ser Gly Val
     3080                3085                3090

Ala Lys Asp Asp Leu Asn Lys Thr Val Thr Arg Thr Ile Asn Ile
     3095                3100                3105

Thr Thr Pro Asp Gly Lys Thr Gln Thr Ile Thr Gln Lys Ala Glu
     3110                3115                3120

Phe Thr Arg Ser Ala Thr Val Asp Glu Val Thr Gly Glu Val Thr
     3125                3130                3135

Tyr Gly Pro Trp Ser Lys Asn Val Val Leu Glu Ser Val Asp Val
     3140                3145                3150

Pro Asn Ile Ser Gly Tyr Val Pro Ser Ala Ser Val Pro Glu Ile
     3155                3160                3165

Thr Val Thr Pro Asn Asp Gln Asp Met Thr Ile Asn Ile Thr Tyr
     3170                3175                3180

Lys Lys Leu Asp Ser Gly Lys Ala Ala Asp Gln Gly Gly Asn Ala
     3185                3190                3195

Ser Asn Gly Gly Gln Ala Thr Asn Gly Gly Ser Thr Thr Gly Gln
     3200                3205                3210

Ser Ala Gln Asn Gly Gln Ser Gly Gln Thr Gln Asn Asn Ala Gly
     3215                3220                3225

Ala Gln Gln Leu Pro Gln Thr Gly Asn Ala Asn Asn Glu Lys Gly
     3230                3235                3240

Ala Leu Gly Leu Ala Ser Ala Met Phe Ala Ala Gly Leu Gly Leu
     3245                3250                3255

Gly Phe Gly Ser Lys Lys Lys Cys His Glu Asp
     3260                3265

<210> SEQ ID NO 19
<211> LENGTH: 164
<212> TYPE: PRT
<213> ORGANISM: Lactobacillus gasseri
<220> FEATURE:
<223> OTHER INFORMATION: MUB200

<400> SEQUENCE: 19

Thr Val Thr Tyr Lys Ala Asn Pro Gln Lys Ile Thr Val Asn Tyr Ile
1               5                   10                  15

Asp Asp Thr Thr Gly Lys Thr Leu Ser Thr Lys Asp Leu Asn Gly Lys
                20                  25                  30

Ser Asp Glu Lys Ser Asp Tyr Ala Thr Lys Asp Ser Ile Ala Glu Tyr
            35                  40                  45

Glu Lys Gln His Tyr Asp Leu Val Ser Asp Glu Thr Asn Gly Ser Glu
        50                  55                  60

Leu Val Phe Asp His Asp Asp Lys Val Asp Gln Val Tyr Asn Val His
65                  70                  75                  80

Phe Thr His His Met Thr Ser Ile Asn Asp Thr Lys Lys Ile Asn Glu
                85                  90                  95

Thr Ile His Tyr Val Tyr Glu Asp Gly Thr Lys Ala His Asp Asp Ile
            100                 105                 110

Asn Gly Gln Pro Val Ile Phe Thr His Asp Gly Glu Arg Asp Glu Val
        115                 120                 125

```
Thr Asn Lys Glu His Trp Asn Asp Trp Lys Ser Glu Lys Asp Ser Phe
            130                 135                 140
Asp Glu Val Asn Ser Pro Lys Ile Ala Gly Tyr Thr Pro Asp Phe Ala
145                 150                 155                 160
Thr Ile Glu Lys

<210> SEQ ID NO 20
<211> LENGTH: 152
<212> TYPE: PRT
<213> ORGANISM: Lactobacillus johnsonii
<220> FEATURE:
<223> OTHER INFORMATION: MUB200

<400> SEQUENCE: 20

Ile Tyr Ser Pro Asp Ala Gln His Met Ile Ile Thr Tyr Val Asp Asp
1               5                   10                  15
Thr Thr Gly Glu Ile Leu Arg Thr Asp Lys Arg Asp Gly Phe Ser Asp
            20                  25                  30
Gln Asp Ala Lys Tyr Thr Thr Gly Asp Thr Ile Lys Gln Tyr Glu Asp
        35                  40                  45
Gln His Tyr Lys Leu Val Ser Asp Ser Thr Lys Gly Gln Pro Leu Ile
    50                  55                  60
Phe Asp His Asp Asp Asn Val Asp Gln Thr Tyr Glu Val His Leu Lys
65                  70                  75                  80
His Ser Thr Glu Asn Val Thr Arg Asn Asp Thr Val Thr Arg Thr Ile
                85                  90                  95
His Tyr Leu Tyr Asp Asn Gly Asn Thr Ala Lys Pro Asp Lys Thr Gln
            100                 105                 110
Thr Val Ser Phe Asn Glu Thr Gly Thr Lys Asp Val Thr Gly Lys
        115                 120                 125
Thr Thr Trp Asp Asn Asp Asn Ala Gln Ser Val Asp Ser Val Ile Thr
    130                 135                 140
Pro Ser Ile Thr Gly Tyr Thr Pro
145                 150

<210> SEQ ID NO 21
<211> LENGTH: 168
<212> TYPE: PRT
<213> ORGANISM: Lactobacillus fermentum
<220> FEATURE:
<223> OTHER INFORMATION: MUB200

<400> SEQUENCE: 21

Thr Ile Thr Tyr Thr Ala Asp Thr Gln Lys Gly Ser Val Ser Tyr Val
1               5                   10                  15
Asp Asp Thr Thr Gly Lys Thr Leu Lys Thr Asp Ser Ile Ser Gly Thr
            20                  25                  30
Thr Gly Ser Lys Ser Ser Tyr Ser Thr Ser Gly Ser Ile Ala Asp Tyr
        35                  40                  45
Lys Lys Gln Gly Tyr Glu Leu Val Thr Asp Gly Tyr Pro Ala Asp Leu
    50                  55                  60
Thr Phe Asp Asn Asp Asp Thr Lys Asp Gln Asn Phe Thr Val His Leu
65                  70                  75                  80
Lys His Gln Asn Ile Gln Ser Thr Glu Ala Lys Thr Val Thr Glu Thr
                85                  90                  95
Ile His Tyr Gln Gly Ala Gly Asn Gln Thr Pro Ala Asp Ser Ala Asp
            100                 105                 110
```

```
Gln Ser Phe Ala Ala Val Thr Ser Pro Val Ile Lys Gly Tyr Thr Ala
        115                 120                 125

Asp Lys Ala Gln Ile Asp Lys Gln Thr Val Asn Gly Asp Ser Lys Asn
    130                 135                 140

Thr Ala Gln Val Thr Phe Thr Arg Gln Val Ser Thr Asp Ala Val Thr
145                 150                 155                 160

Gly Glu Lys Thr Tyr Gly Ser Trp
                165

<210> SEQ ID NO 22
<211> LENGTH: 182
<212> TYPE: PRT
<213> ORGANISM: Lactobacillus acidophilus
<220> FEATURE:
<223> OTHER INFORMATION: MUB200

<400> SEQUENCE: 22

Val Val Pro Ala Lys Asp Gln Ala Ala Val Asn Tyr Val Asp Ala
1               5                   10                  15

Asp Glu Asp Asn Lys Leu Ile Thr Ser Ser Gly Asp Leu Thr Gly Lys
                20                  25                  30

Ala Gly Glu Thr Ile Asn Tyr Ser Thr Ala Asp Thr Ile Lys Asp Leu
            35                  40                  45

Glu Asn Lys Gly Tyr Val Leu Val Asn Asp Gly Phe Pro Ala Gly Ala
    50                  55                  60

Lys Tyr Asp Ser Asp Asn Thr Thr Gln Ile Tyr Thr Val Leu
65                  70                  75                  80

Lys His Gly Thr Thr Thr Ile Thr Pro Asp Lys Pro Gly Lys Pro Gly
                85                  90                  95

Glu Pro Ile Asn Pro Asn Asp Pro Asp Gly Pro Lys Trp Pro Asp Asn
            100                 105                 110

Ser Gly Glu Asn Asn Leu Ser Lys Thr Gly Thr Gln Thr Ile His Tyr
        115                 120                 125

Thr Gly Ala Gly Asp Lys Thr Pro Glu Asp Asn Lys Gln Glu Phe Thr
    130                 135                 140

Phe Thr Lys Thr Met Val Val Asp Asn Val Thr Gly Lys Val Ile Thr
145                 150                 155                 160

Asp Gly Ala Trp Asn Val Thr Ser His Thr Phe Gly Asn Val Asp Thr
                165                 170                 175

Pro Val Ile Asp Gly Tyr
            180

<210> SEQ ID NO 23
<211> LENGTH: 70
<212> TYPE: PRT
<213> ORGANISM: Lactobacillus acidophilus
<220> FEATURE:
<223> OTHER INFORMATION: NCFM

<400> SEQUENCE: 23

Val Asn Tyr Val Asp Ala Asp Glu Asp Asn Lys Leu Ile Thr Ser Ser
1               5                   10                  15

Gly Asp Leu Thr Gly Lys Ala Gly Glu Thr Ile Asn Tyr Ser Thr Ala
                20                  25                  30

Asp Thr Ile Lys Asp Leu Glu Asn Lys Gly Tyr Val Leu Val Asn Asp
            35                  40                  45

Gly Phe Pro Ala Gly Ala Lys Tyr Asp Ser Asp Asp Asn Thr Thr Gln
```

```
                50                  55                  60
Ile Tyr Thr Val Val Leu
 65                  70

<210> SEQ ID NO 24
<211> LENGTH: 68
<212> TYPE: PRT
<213> ORGANISM: Streptococcus salivarius
<220> FEATURE:
<223> OTHER INFORMATION: SK126

<400> SEQUENCE: 24

Ile Thr Tyr Val Asp Gln Thr Thr Gly Gln Thr Leu Ala Asn Asp Gln
 1               5                  10                  15

Val Gly Gly Lys Ser Gly Glu Ala Ile Asn Tyr Ser Thr Ala Asp Lys
                20                  25                  30

Ile Lys Tyr Tyr Glu Asp Arg Gly Tyr Val Leu Val Ser Asp Glu Phe
            35                  40                  45

Pro Thr Gly Ala His Phe Asp Asn Asp Ala Ser Val Asp Gln Thr Trp
        50                  55                  60

Thr Val Thr Leu
 65

<210> SEQ ID NO 25
<211> LENGTH: 70
<212> TYPE: PRT
<213> ORGANISM: Lactobacillus johnsonii
<220> FEATURE:
<223> OTHER INFORMATION: NCC 533

<400> SEQUENCE: 25

Val Asn Tyr Ile Asp Ala Asp Asp Asn Ala Ile Ile Thr Ser Ser
 1               5                  10                  15

Asp Asn Leu Thr Gly Lys Ala Gly Glu Lys Ile Asp Tyr Ser Thr Ala
                20                  25                  30

Ser Thr Ile Glu Glu Leu Glu Asn Lys Gly Tyr Val Leu Val Ser Asp
            35                  40                  45

Gly Phe Pro Ala Gly Ala Thr Phe Asp Asn Asp Asn Thr Thr Gln
        50                  55                  60

Ile Tyr Thr Val Val Leu
 65                  70

<210> SEQ ID NO 26
<211> LENGTH: 68
<212> TYPE: PRT
<213> ORGANISM: Streptococcus salivarius
<220> FEATURE:
<223> OTHER INFORMATION: SK126

<400> SEQUENCE: 26

Ile Thr Tyr Val Asp Gln Thr Thr Gly Gln Thr Leu Ala Asn Asp Gln
 1               5                  10                  15

Val Gly Gly Lys Ser Gly Glu Ala Ile Asn Tyr Ser Thr Ala Asp Lys
                20                  25                  30

Ile Lys Tyr Tyr Glu Asp Arg Gly Tyr Val Leu Val Ser Asp Glu Phe
            35                  40                  45

Pro Lys Gly Ala His Phe Asp Asn Asp Ala Ser Val Asp Gln Ile Trp
        50                  55                  60

Thr Val Thr Leu
 65
```

<210> SEQ ID NO 27
<211> LENGTH: 68
<212> TYPE: PRT
<213> ORGANISM: Streptococcus salivarius
<220> FEATURE:
<223> OTHER INFORMATION: SK126

<400> SEQUENCE: 27

Ile Thr Tyr Val Asp Gln Thr Thr Ser Gln Thr Leu Ala Asn Asp Gln
1               5                   10                  15

Val Gly Gly Lys Ser Gly Glu Ala Ile Asn Tyr Ser Thr Ala Asp Lys
            20                  25                  30

Ile Lys Tyr Tyr Glu Asp Arg Gly Tyr Val Leu Val Ser Asp Glu Phe
        35                  40                  45

Pro Thr Gly Ala His Phe Asp Asn Asp Ala Ser Val Asp Gln Thr Trp
    50                  55                  60

Thr Val Thr Leu
65

<210> SEQ ID NO 28
<211> LENGTH: 70
<212> TYPE: PRT
<213> ORGANISM: Lactobacillus reuteri
<220> FEATURE:
<223> OTHER INFORMATION: 100-23

<400> SEQUENCE: 28

Val Asn Tyr Val Asp Gln Asp Asn Asn Ala Gln Ile Ala Thr Ser
1               5                   10                  15

Gly Asn Leu Thr Gly Lys Pro Gly Ser Val Ile Asn Tyr Ser Thr Ala
            20                  25                  30

Asp Gln Ile Lys Gln Leu Glu Ala Gln Gly Tyr Val Leu Val Ser Asp
        35                  40                  45

Gly Phe Pro Ala Gly Ala Val Phe Asp Asn Asp Asn Thr Thr Gln
    50                  55                  60

Thr Tyr Thr Val Val Leu
65                  70

<210> SEQ ID NO 29
<211> LENGTH: 66
<212> TYPE: PRT
<213> ORGANISM: Leuconostoc argentinum
<220> FEATURE:
<223> OTHER INFORMATION: KCTC 3773

<400> SEQUENCE: 29

Val Ser Tyr Val Asp Asp Thr Thr Gly Lys Thr Leu Lys Thr Asp Ser
1               5                   10                  15

Ile Ser Gly Thr Thr Gly Ser Lys Ser Ser Tyr Ser Thr Ser Gly Asn
            20                  25                  30

Ile Ala Asp Tyr Lys Lys His Gly Tyr Glu Leu Val Thr Asp Gly Tyr
        35                  40                  45

Pro Ala Asp Leu Thr Phe Asp Asn Asp Lys Thr Asp Gln Asn Phe
    50                  55                  60

Thr Val
65

<210> SEQ ID NO 30
<211> LENGTH: 66

<212> TYPE: PRT
<213> ORGANISM: Lactobacillus coryniformis
<220> FEATURE:
<223> OTHER INFORMATION: subspecies torquens KCTC 3535

<400> SEQUENCE: 30

Val Ser Tyr Val Asp Asp Thr Thr Gly Lys Thr Leu Lys Thr Asp Ser
1               5                   10                  15

Ile Ser Gly Thr Thr Gly Ser Lys Ser Ser Tyr Ser Thr Ser Gly Asn
            20                  25                  30

Ile Ala Asp Tyr Lys Lys Gln Gly Tyr Glu Leu Val Thr Asp Gly Tyr
        35                  40                  45

Pro Ala Asp Leu Thr Phe Asp Asn Asp Thr Thr Asp Gln Asn Phe
    50                  55                  60

Thr Val
65

<210> SEQ ID NO 31
<211> LENGTH: 70
<212> TYPE: PRT
<213> ORGANISM: Lactobacillus reuteri
<220> FEATURE:
<223> OTHER INFORMATION: 100-23

<400> SEQUENCE: 31

Val Asn Tyr Val Asp Gln Asp Asn Asn Ala Gln Ile Ala Thr Ser
1               5                   10                  15

Gly Asn Leu Thr Gly Lys Pro Gly Ser Val Ile Asn Tyr Ser Thr Ala
            20                  25                  30

Asp Gln Ile Lys Gln Leu Glu Asp Gln Gly Tyr Val Leu Val Ser Asp
        35                  40                  45

Gly Phe Pro Ala Gly Ala Val Phe Asp Asn Asp Asn Thr Thr Gln
    50                  55                  60

Thr Tyr Thr Val Val Leu
65                  70

<210> SEQ ID NO 32
<211> LENGTH: 70
<212> TYPE: PRT
<213> ORGANISM: Streptococcus salivarius
<220> FEATURE:
<223> OTHER INFORMATION: CCHSS3

<400> SEQUENCE: 32

Ala Ser Val Thr Tyr Arg Asp Glu Thr Ser Gly Ser Ile Leu Glu Thr
1               5                   10                  15

Val Ala Leu Ala Gly Lys Ser Gly Glu Ala Ile Asn Tyr Ser Thr Ala
            20                  25                  30

Glu Arg Ile Lys His Tyr Gln Asp Leu Gly Tyr Ala Leu Val Thr Asp
        35                  40                  45

Gly Tyr Pro Ala Gly Ala Ser Phe Asp Leu Asp Ser Thr Val Asp Gln
    50                  55                  60

Ala Trp Thr Val Ser Phe
65                  70

<210> SEQ ID NO 33
<211> LENGTH: 66
<212> TYPE: PRT
<213> ORGANISM: Leuconostoc citreum
<220> FEATURE:
<223> OTHER INFORMATION: KM20

<400> SEQUENCE: 33

Val Ser Tyr Val Asp Asp Thr Thr Gly Lys Thr Leu Lys Thr Asp Ser
1               5                   10                  15

Ile Ser Gly Thr Thr Gly Ser Lys Ser Ser Tyr Ser Thr Ser Gly Asn
            20                  25                  30

Ile Ala Asp Tyr Lys Lys Gln Gly Tyr Glu Leu Val Thr Asp Gly Tyr
            35                  40                  45

Pro Ala Asp Leu Thr Phe Asp Asn Asn Asp Thr Thr Asp Gln Asn Phe
            50                  55                  60

Thr Val
65

<210> SEQ ID NO 34
<211> LENGTH: 64
<212> TYPE: PRT
<213> ORGANISM: Lactobacillus gasseri
<220> FEATURE:
<223> OTHER INFORMATION: 202-4

<400> SEQUENCE: 34

Asp Gly Ala Asn Lys Gln Leu Ala Thr Ser Gly Asp Leu Thr Gly Lys
1               5                   10                  15

Ser Gly Ser Glu Ile Ser Tyr Ser Thr Ala Asp Gln Ile Lys Lys Leu
            20                  25                  30

Ile Asn Gln Gly Tyr Val Leu Lys Asn Asp Gly Phe Pro Ala Gly Ala
            35                  40                  45

Val Phe Asp Asn Asp Asp Ser Lys Asn Gln Val Phe Tyr Val Asp Phe
            50                  55                  60

<210> SEQ ID NO 35
<211> LENGTH: 64
<212> TYPE: PRT
<213> ORGANISM: Lactobacillus gasseri
<220> FEATURE:
<223> OTHER INFORMATION: 224-1

<400> SEQUENCE: 35

Asp Gly Ala Asn Lys Gln Leu Ala Thr Ser Gly Asp Leu Thr Gly Lys
1               5                   10                  15

Ser Gly Ser Glu Ile Ser Tyr Ser Thr Ala Asp Gln Ile Lys Lys Leu
            20                  25                  30

Ile Asn Gln Gly Tyr Val Leu Lys Asn Asp Gly Phe Pro Ala Gly Ala
            35                  40                  45

Val Phe Asp Asn Asp Asp Ser Lys Asn Gln Val Phe Tyr Val Asp Phe
            50                  55                  60

<210> SEQ ID NO 36
<211> LENGTH: 64
<212> TYPE: PRT
<213> ORGANISM: Lactobacillus gasseri
<220> FEATURE:
<223> OTHER INFORMATION: ATCC 33323

<400> SEQUENCE: 36

Asp Gly Ala Asn Lys Gln Leu Ala Thr Ser Gly Asp Leu Thr Gly Lys
1               5                   10                  15

Ser Gly Ser Glu Ile Ser Tyr Ser Thr Ala Asp Gln Ile Lys Lys Leu
            20                  25                  30

Ile Asn Gln Gly Tyr Val Leu Lys Asn Asp Gly Phe Pro Ala Gly Ala

```
                35                  40                  45

Val Phe Asp Asn Asp Asp Ser Lys Asn Gln Val Phe Tyr Val Asp Phe
    50                  55                  60

<210> SEQ ID NO 37
<211> LENGTH: 64
<212> TYPE: PRT
<213> ORGANISM: Lactobacillus gasseri
<220> FEATURE:
<223> OTHER INFORMATION: MV-22

<400> SEQUENCE: 37

Asp Gly Ala Asn Lys Gln Leu Ala Thr Ser Gly Asp Leu Thr Gly Lys
1               5                   10                  15

Ser Gly Ser Glu Ile Ser Tyr Ser Thr Ala Asp Gln Ile Lys Lys Leu
                20                  25                  30

Ile Asn Gln Gly Tyr Val Leu Lys Asn Asp Gly Phe Pro Ala Gly Ala
            35                  40                  45

Val Phe Asp Asn Asp Asp Ser Lys Asn Gln Val Phe Tyr Val Asp Phe
    50                  55                  60

<210> SEQ ID NO 38
<211> LENGTH: 71
<212> TYPE: PRT
<213> ORGANISM: Lactobacillus delbrueckii
<220> FEATURE:
<223> OTHER INFORMATION: subspecies bulgaricus ND02

<400> SEQUENCE: 38

Ala Lys Val Ala Tyr Ile Asp Asp Lys Thr Gly Lys Thr Leu Lys Thr
1               5                   10                  15

Asp Ser Leu Thr Gly Val Thr Asn Ala Lys Ser Gly Tyr Thr Thr Ala
                20                  25                  30

Asp Ser Ile Lys Thr Tyr Gln Ala Leu Gly Tyr Lys Leu Val Ser Asp
            35                  40                  45

Asp Thr Lys Gly Ala Glu Ile Val Phe Asp Asn Glu Asp Gly Lys Asp
    50                  55                  60

Gln Ser Tyr Thr Val His Phe
65                  70

<210> SEQ ID NO 39
<211> LENGTH: 70
<212> TYPE: PRT
<213> ORGANISM: Lactobacillus crispatus
<220> FEATURE:
<223> OTHER INFORMATION: 125-2-CHN

<400> SEQUENCE: 39

Val Asn Tyr Ile Asp Ser Asp Glu Gly Asn Lys Val Ile Thr Thr Ser
1               5                   10                  15

Gly Asn Leu Ser Gly Lys Ala Gly Ser Thr Ile Asp Tyr Ser Thr Lys
                20                  25                  30

Ser Thr Ile Ala Asp Leu Glu Asn Lys Gly Tyr Val Leu Val Asn Asp
            35                  40                  45

Gly Phe Pro Ala Gly Ala Lys Phe Asp Ser Asp Asp Asn Thr Thr Gln
    50                  55                  60

Ile Phe Thr Val Val Leu
65                  70

<210> SEQ ID NO 40
```

```
<211> LENGTH: 70
<212> TYPE: PRT
<213> ORGANISM: Streptococcus sp.
<220> FEATURE:
<223> OTHER INFORMATION: S. species C150

<400> SEQUENCE: 40

Ala Ser Val Thr Tyr Arg Asp Glu Thr Gly Gly Ser Thr Leu Glu Thr
1               5                   10                  15

Val Ser Leu Ala Gly Lys Ser Gly Glu Ala Val Gly Tyr Ser Thr Ala
            20                  25                  30

Glu Arg Ile Lys His Tyr Gln Asp Leu Gly Tyr Val Leu Val Thr Asp
        35                  40                  45

Gly Tyr Pro Ala Gly Thr Thr Phe Asp Leu Asp Ser Thr Val Asp Gln
    50                  55                  60

Ala Trp Thr Val Ser Phe
65                  70

<210> SEQ ID NO 41
<211> LENGTH: 70
<212> TYPE: PRT
<213> ORGANISM: Streptococcus salivarius
<220> FEATURE:
<223> OTHER INFORMATION: SK126

<400> SEQUENCE: 41

Ala Ser Val Thr Tyr Arg Asp Glu Thr Ser Gly Ser Thr Leu Glu Thr
1               5                   10                  15

Val Ala Leu Ala Gly Lys Ser Gly Glu Ala Val Asn Tyr Ser Thr Ala
            20                  25                  30

Asp Arg Ile Lys His Tyr Gln Asp Leu Gly Tyr Val Leu Val Thr Asp
        35                  40                  45

Gly Tyr Pro Ala Gly Ala Thr Phe Asp Leu Asp Ser Thr Val Asp Gln
    50                  55                  60

Ala Trp Thr Val Ser Phe
65                  70

<210> SEQ ID NO 42
<211> LENGTH: 70
<212> TYPE: PRT
<213> ORGANISM: Streptococcus mitis
<220> FEATURE:
<223> OTHER INFORMATION: NCTC 12261

<400> SEQUENCE: 42

Ile Arg Tyr Val Ser Thr Asn Gly Asn Gln Val Leu Lys Thr Asp Glu
1               5                   10                  15

Val Thr Gly Lys Ser Gly Glu Ala Ile Ala Tyr Ser Thr Thr Ser Gln
            20                  25                  30

Ile Asn Glu Phe Lys Lys Gln Gly Tyr Lys Leu Val Ser Asp Glu Phe
        35                  40                  45

Thr Ala Gly Gly Ala Lys Val Tyr Asp Tyr Asp Thr Ala Arg Asp Gln
    50                  55                  60

Val Tyr Thr Val Thr Leu
65                  70

<210> SEQ ID NO 43
<211> LENGTH: 69
<212> TYPE: PRT
<213> ORGANISM: Weissella cibaria
<220> FEATURE:
```

-continued

<223> OTHER INFORMATION: KACC 11862

<400> SEQUENCE: 43

```
Ile Ala Tyr Ile Asp Lys Thr Thr Gly Lys Gln Leu Ala Leu Asp Pro
1               5                   10                  15

Ile Thr Gly His Ser Asp Glu Ser Ser Thr Tyr Thr Thr Ala Asp Lys
            20                  25                  30

Ile Ala Ala Tyr Glu Ala Ala Gly Tyr Val Leu Val Ser Asp Gly Tyr
        35                  40                  45

Pro Gly Ala Asn Phe Thr Phe Asp Arg Glu Asp Tyr Asp Gln Thr
    50                  55                  60

Tyr Glu Val Ile Leu
65
```

<210> SEQ ID NO 44
<211> LENGTH: 68
<212> TYPE: PRT
<213> ORGANISM: Streptococcus salivarius
<220> FEATURE:
<223> OTHER INFORMATION: CCHSS3

<400> SEQUENCE: 44

```
Ile Thr Tyr Ile Asp Glu Thr Thr Gly Ala Tyr Leu Val Ser Asp Gln
1               5                   10                  15

Leu Thr Gly Glu Leu Gly Glu Ala Ile Glu Tyr Gly Thr Ala Thr Arg
            20                  25                  30

Ile Lys Thr Phe Lys Asp Met Gly Tyr Glu Leu Ile Gln Asp Glu Phe
        35                  40                  45

Pro Lys Asp Ala Ile Phe Asp Asp Lys Asp Ile Asp Gln Glu Trp
    50                  55                  60

Phe Val Leu Leu
65
```

<210> SEQ ID NO 45
<211> LENGTH: 67
<212> TYPE: PRT
<213> ORGANISM: Lactobacillus johnsonii
<220> FEATURE:
<223> OTHER INFORMATION: ATCC 33200

<400> SEQUENCE: 45

```
Val Thr Tyr Val Asp Asp Lys Thr Gly Lys Thr Leu Lys Val Asp Asn
1               5                   10                  15

Leu Asn Gly Val Thr Ser Ala Lys Ser Gly Tyr Thr Thr Lys Ala Ala
            20                  25                  30

Ile Asp Thr Tyr Thr Gly Leu Gly Tyr Thr Leu Val Ser Asp Asp Thr
        35                  40                  45

Asn Gly Asn Glu Val Val Phe Asp Asn Asp Ser Asn Asp Gln Ala
    50                  55                  60

Phe Thr Val
65
```

<210> SEQ ID NO 46
<211> LENGTH: 70
<212> TYPE: PRT
<213> ORGANISM: Lactobacillus acidophilus
<220> FEATURE:
<223> OTHER INFORMATION: NCFM

<400> SEQUENCE: 46

```
Val Asn Tyr Ile Asp Ala Asp Glu Gly Asn Lys Val Ile Ile Ser Ser
1               5                   10                  15

Gly Asn Leu Ile Gly Lys Ala Gly Asp Lys Val Asp Tyr Asn Thr Ser
            20                  25                  30

Asp Thr Ile Lys Asn Leu Glu Asn Lys Gly Tyr Val Leu Val His Asn
            35                  40                  45

Gly Phe Pro Asp Gly Val Thr Phe Asp Asn Asp Ser Thr Ile Gln
        50                  55                  60

Thr Tyr Thr Val Ile Leu
65              70

<210> SEQ ID NO 47
<211> LENGTH: 70
<212> TYPE: PRT
<213> ORGANISM: Lactobacillus acidophilus
<220> FEATURE:
<223> OTHER INFORMATION: ATCC 4796

<400> SEQUENCE: 47

Val Asn Tyr Ile Asp Ala Asp Glu Gly Asn Lys Val Ile Ile Ser Ser
1               5                   10                  15

Gly Asn Leu Ile Gly Lys Ala Gly Asp Lys Val Asp Tyr Asn Thr Ser
            20                  25                  30

Asp Thr Ile Lys Asn Leu Glu Asn Lys Gly Tyr Val Leu Val His Asn
            35                  40                  45

Gly Phe Pro Asp Gly Val Thr Phe Asp Asn Asp Ser Thr Ile Gln
        50                  55                  60

Thr Tyr Thr Val Ile Leu
65              70

<210> SEQ ID NO 48
<211> LENGTH: 68
<212> TYPE: PRT
<213> ORGANISM: Streptococcus salivarius
<220> FEATURE:
<223> OTHER INFORMATION: SK126

<400> SEQUENCE: 48

Ile Thr Tyr Ile Asp Glu Thr Thr Gly Ala Tyr Leu Val Ser Asp Gln
1               5                   10                  15

Leu Thr Gly Glu Leu Gly Glu Ala Ile Glu Tyr Gly Thr Ala Thr Arg
            20                  25                  30

Ile Lys Thr Phe Lys Asp Met Gly Tyr Asp Leu Ile Gln Asp Glu Phe
            35                  40                  45

Pro Lys Asp Ala Ile Phe Asp Asp Lys Asp Ile Asp Gln Glu Trp
        50                  55                  60

Phe Val Leu Leu
65

<210> SEQ ID NO 49
<211> LENGTH: 66
<212> TYPE: PRT
<213> ORGANISM: Lactobacillus delbrueckii
<220> FEATURE:
<223> OTHER INFORMATION: Subspecies bulgaricus ND02

<400> SEQUENCE: 49

Val Ser Tyr Val Asp Asp Thr Thr Gly Lys Thr Leu Lys Thr Asp Ser
1               5                   10                  15

Ile Ser Gly Ile Thr Gly Ser Lys Ser Ser Tyr Ser Thr Ser Gly Ser
```

```
            20                  25                  30

Ile Ala Asp Tyr Lys Lys Gln Gly Tyr Glu Leu Val Thr Asp Gly Tyr
        35                  40                  45

Pro Ala Asp Leu Thr Phe Asp Asn Asp Thr Asp Gln Asn Phe
    50                  55                  60

Thr Val
65

<210> SEQ ID NO 50
<211> LENGTH: 66
<212> TYPE: PRT
<213> ORGANISM: Lactobacillus fermentum
<220> FEATURE:
<223> OTHER INFORMATION: 28-3-CHN

<400> SEQUENCE: 50

Val Ser Tyr Val Asp Asp Thr Thr Gly Lys Thr Leu Lys Thr Asp Ser
1               5                   10                  15

Ile Ser Gly Thr Thr Gly Ser Lys Ser Ser Tyr Ser Thr Ser Gly Ser
                20                  25                  30

Ile Ala Asp Tyr Lys Lys Gln Gly Tyr Glu Leu Val Thr Asp Gly Tyr
        35                  40                  45

Pro Ala Asp Leu Thr Phe Asp Asn Asp Thr Asp Gln Asn Phe
    50                  55                  60

Thr Val
65

<210> SEQ ID NO 51
<211> LENGTH: 66
<212> TYPE: PRT
<213> ORGANISM: Lactobacillus fermentum
<220> FEATURE:
<223> OTHER INFORMATION: IFO 3956

<400> SEQUENCE: 51

Val Ser Tyr Val Asp Asp Thr Thr Gly Lys Thr Leu Lys Thr Asp Ser
1               5                   10                  15

Ile Ser Gly Thr Thr Gly Ser Lys Ser Ser Tyr Ser Thr Ser Gly Ser
                20                  25                  30

Ile Ala Asp Tyr Lys Lys Gln Gly Tyr Glu Leu Val Thr Asp Gly Tyr
        35                  40                  45

Pro Ala Asp Leu Thr Phe Asp Asn Asp Thr Lys Asp Gln Asn Phe
    50                  55                  60

Thr Val
65

<210> SEQ ID NO 52
<211> LENGTH: 68
<212> TYPE: PRT
<213> ORGANISM: Streptococcus sp.
<220> FEATURE:
<223> OTHER INFORMATION: S. species C150

<400> SEQUENCE: 52

Val Thr Tyr Val Asp Gly Thr Thr Arg Lys Lys Leu Glu Val Val Asp
1               5                   10                  15

Leu Leu Gly Lys Ser Gly Glu Val Ile Asp Tyr Ser Thr Ile Glu Arg
                20                  25                  30

Ile Lys Tyr Tyr Ser Asp Arg Gly Tyr Thr Leu Leu Ala Asp Gly Phe
        35                  40                  45
```

```
Thr Asn Gly Val Ile Phe Asp Gly Asp Ser His Val Asp Gln Asn Phe
 50                  55                  60

Met Val Thr Leu
 65

<210> SEQ ID NO 53
<211> LENGTH: 66
<212> TYPE: PRT
<213> ORGANISM: Lactobacillus fermentum
<220> FEATURE:
<223> OTHER INFORMATION: 28-3-CHN

<400> SEQUENCE: 53

Val Ser Tyr Val Asp Asp Thr Thr Arg Lys Thr Leu Lys Thr Asp Ser
  1               5                  10                  15

Ile Ser Gly Thr Thr Gly Ser Lys Ser Ser Tyr Ser Thr Ser Gly Ser
                 20                  25                  30

Ile Ala Asp Tyr Lys Lys Gln Gly Tyr Glu Leu Val Thr Asp Gly Tyr
             35                  40                  45

Pro Ala Asp Leu Met Phe Asp Asn Asp Asp Thr Thr Asp Gln Asn Phe
 50                  55                  60

Thr Val
 65

<210> SEQ ID NO 54
<211> LENGTH: 64
<212> TYPE: PRT
<213> ORGANISM: Lactobacillus gasseri
<220> FEATURE:
<223> OTHER INFORMATION: JV-V03

<400> SEQUENCE: 54

Ile Ile Tyr Val Asp Glu Thr Thr Gly Lys Ala Leu Glu Thr Ala Thr
  1               5                  10                  15

Val Asp Gly Lys Tyr Asn Glu Ser Ile Asn Tyr Ser Thr Ala Asp Lys
                 20                  25                  30

Ile Lys Tyr Tyr Glu Ser Leu Gly Tyr Glu Leu Val Lys Asp Gly Tyr
             35                  40                  45

Thr Ala Gly Lys Phe Gly Glu Thr Thr Lys Thr Phe Tyr Val Ile Phe
 50                  55                  60

<210> SEQ ID NO 55
<211> LENGTH: 52
<212> TYPE: PRT
<213> ORGANISM: Lactobacillus gasseri
<220> FEATURE:
<223> OTHER INFORMATION: 202-4

<400> SEQUENCE: 55

Ile Val Tyr Val Asp Glu Thr Thr Gly Lys Glu Leu Glu Arg Ala Thr
  1               5                  10                  15

Val Asp Gly Lys Tyr Asn Glu Thr Ile Asn Tyr Ser Thr Ala Asp Lys
                 20                  25                  30

Ile Lys Tyr Tyr Glu Ser Leu Gly Tyr Glu Leu Val Lys Asp Gly Tyr
             35                  40                  45

Thr Gly Gly Glu
 50

<210> SEQ ID NO 56
<211> LENGTH: 68
```

```
<212> TYPE: PRT
<213> ORGANISM: Lactobacillus gasseri
<220> FEATURE:
<223> OTHER INFORMATION: MV-22

<400> SEQUENCE: 56

Leu Asp Asn Glu Gly Gln Gln Ile Thr Ser Ser Gly Pro Leu Ile Gly
1               5                   10                  15

Lys Pro Asn Glu Asn Ile Thr Asp Leu Tyr Ser Thr Ser Ile Pro Leu
            20                  25                  30

Ala Gly Leu Glu Lys Ala Gly Tyr His Val Ile Phe Asn Asn Phe Asp
        35                  40                  45

Gly Asn Asn Lys Ile Gln Lys Phe Asp Gly Asn Asp Leu Thr Thr Gln
    50                  55                  60

Val Phe Thr Val
65

<210> SEQ ID NO 57
<211> LENGTH: 68
<212> TYPE: PRT
<213> ORGANISM: Lactobacillus gasseri
<220> FEATURE:
<223> OTHER INFORMATION: L. gasseri 202-4

<400> SEQUENCE: 57

Leu Asp Asn Glu Gly Gln Gln Ile Thr Ser Ser Gly Pro Leu Ile Gly
1               5                   10                  15

Lys Pro Asn Glu Asn Ile Thr Asp Leu Tyr Ser Thr Ser Ile Pro Leu
            20                  25                  30

Ala Gly Leu Glu Lys Ala Gly Tyr His Val Ile Phe Asn Asn Phe Asp
        35                  40                  45

Gly Asn Asn Lys Ile Gln Lys Phe Asp Gly Asn Asp Leu Thr Thr Gln
    50                  55                  60

Val Phe Thr Val
65

<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence: Synthetic
      MUB40-1 polypeptide sequence

<400> SEQUENCE: 58

Thr Ala Glu Gly Ile Lys Lys Phe Glu Gly Asp Gly Tyr Glu Leu Phe
1               5                   10                  15

Lys Asp Asn Phe Pro Ala Gly Glu Lys Phe Asp Asn Asp Thr Asn
            20                  25                  30

Asp Gln Phe Tyr Thr Val Ile Phe
        35                  40

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence: Synthetic
      MUB40-2 polypeptide sequence

<400> SEQUENCE: 59

Gly Tyr Thr Asp Glu Thr Ile Pro Tyr Ser Thr Ala Glu Gly Ile Lys
```

```
                1               5                  10                 15
Lys Phe Glu Gly Asp Gly Tyr Glu Leu Phe Lys Asp Asn Phe Pro Ala
            20                 25                 30
Gly Glu Lys Phe Asp Asn Asp Asp
            35                 40
```

<210> SEQ ID NO 60
<211> LENGTH: 40
<212> TYPE: PRT
<213> ORGANISM: Artificial Sequence
<220> FEATURE:
<223> OTHER INFORMATION: Description of Artificial Sequence: Synthetic
      MUB40-3 polypeptide sequence

<400> SEQUENCE: 60

```
Asp Gln Met Leu Arg Gln Asp Asp Leu Asp Gly Tyr Thr Asp Glu Thr
1               5                  10                 15
Ile Pro Tyr Ser Thr Ala Glu Gly Ile Lys Lys Phe Glu Gly Asp Gly
            20                 25                 30
Tyr Glu Leu Phe Lys Asp Asn Phe
            35                 40
```

<210> SEQ ID NO 61
<211> LENGTH: 40
<212> TYPE: PRT
<213> ORGANISM: Artificial Sequence
<220> FEATURE:
<223> OTHER INFORMATION: Description of Artificial Sequence: Synthetic
      MUB40-4 polypeptide sequence

<400> SEQUENCE: 61

```
Val His Val Gln Tyr Ile Asp Gly Glu Thr Asp Gln Met Leu Arg Gln
1               5                  10                 15
Asp Asp Leu Asp Gly Tyr Thr Asp Glu Thr Ile Pro Tyr Ser Thr Ala
            20                 25                 30
Glu Gly Ile Lys Lys Phe Glu Gly
            35                 40
```

<210> SEQ ID NO 62
<211> LENGTH: 41
<212> TYPE: PRT
<213> ORGANISM: Artificial Sequence
<220> FEATURE:
<223> OTHER INFORMATION: Description of Artificial Sequence: Synthetic
      MUB40-1 polypeptide with cysteine residue at
      N-terminal extremity

<400> SEQUENCE: 62

```
Cys Thr Ala Glu Gly Ile Lys Lys Phe Glu Gly Asp Gly Tyr Glu Leu
1               5                  10                 15
Phe Lys Asp Asn Phe Pro Ala Gly Glu Lys Phe Asp Asn Asp Asp Thr
            20                 25                 30
Asn Asp Gln Phe Tyr Thr Val Ile Phe
            35                 40
```

<210> SEQ ID NO 63
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Cys Gly Tyr Thr Asp Glu Thr Ile Pro Tyr Ser Thr Ala Glu Gly Ile
1               5                   10                  15

Lys Lys Phe Glu Gly Asp Gly Tyr Glu Leu Phe Lys Asp Asn Phe Pro
            20                  25                  30

Ala Gly Glu Lys Phe Asp Asn Asp Asp
        35                  40
```

<210> SEQ ID NO 64
<211> LENGTH: 41
<212> TYPE: PRT
<213> ORGANISM: Artificial Sequence
<220> FEATURE:
<223> OTHER INFORMATION: Description of Artificial Sequence: Synthetic
      MUB40-3 polypeptide with cysteine residue at
      N-terminal extremity

<400> SEQUENCE: 64

```
Cys Asp Gln Met Leu Arg Gln Asp Asp Leu Asp Gly Tyr Thr Asp Glu
1               5                   10                  15

Thr Ile Pro Tyr Ser Thr Ala Glu Gly Ile Lys Lys Phe Glu Gly Asp
            20                  25                  30

Gly Tyr Glu Leu Phe Lys Asp Asn Phe
        35                  40
```

<210> SEQ ID NO 65
<211> LENGTH: 41
<212> TYPE: PRT
<213> ORGANISM: Artificial Sequence
<220> FEATURE:
<223> OTHER INFORMATION: Description of Artificial Sequence: Synthetic
      MUB40-4 polypeptide with cysteine residue at
      N-terminal extremity

<400> SEQUENCE: 65

```
Cys Val His Val Gln Tyr Ile Asp Gly Glu Thr Asp Gln Met Leu Arg
1               5                   10                  15

Gln Asp Asp Leu Asp Gly Tyr Thr Asp Glu Thr Ile Pro Tyr Ser Thr
            20                  25                  30

Ala Glu Gly Ile Lys Lys Phe Glu Gly
        35                  40
```

<210> SEQ ID NO 66
<211> LENGTH: 264
<212> TYPE: DNA
<213> ORGANISM: Artificial Sequence
<220> FEATURE:
<223> OTHER INFORMATION: Description of Artificial Sequence: Synthetic
      gene sequence corresponding to MUB70
<220> FEATURE:
<221> NAME/KEY: misc_feature
<222> LOCATION: (16)..(21)
<223> OTHER INFORMATION: EcorV/SmaI restriction site
<220> FEATURE:
<221> NAME/KEY: misc_feature
<222> LOCATION: (247)..(252)
<223> OTHER INFORMATION: EcorV/SmaI restriction site

<400> SEQUENCE: 66

```
tcgcgaggat ccggtgatat cgttcacgtt caatacattg atggtgaaac tgaccagatg    60
ctgcgtcagg atgatttgga cggctacacg gatgaaacga ttccttacag cacggctgaa   120
ggcatcaaga agtttgaagg cgacggttat gaactgttca aggacaactt cccagctggt   180
gagaagttcg ataacgatga caccaacgat caattctaca cggtaatctt caagcaccat   240
```
cgtggcccgg gagggcccaa gctt                                          264

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      MUB40 consensus sequence
<220> FEATURE:
<221> NAME/KEY: MOD_RES
<222> LOCATION: (3)..(18)
<223> OTHER INFORMATION: Any amino acid and this region may encompass 12
      to 16 residues wherein some positions may be absent
<220> FEATURE:
<221> NAME/KEY: MOD_RES
<222> LOCATION: (19)..(19)
<223> OTHER INFORMATION: Phe or Tyr
<220> FEATURE:
<221> NAME/KEY: MOD_RES
<222> LOCATION: (21)..(29)
<223> OTHER INFORMATION: Any amino acid and this region may encompass 5
      to 9 residues wherein some positions may be absent
<220> FEATURE:
<223> OTHER INFORMATION: See specification as filed for detailed
      description of substitutions and preferred embodiments

<400> SEQUENCE: 67

Gly Tyr Xaa Xaa Xaa Xaa Xaa Xaa Xaa Xaa Xaa Xaa Xaa Xaa Xaa
1               5                   10                  15

Xaa Xaa Xaa Asp Xaa Xaa Xaa Xaa Xaa Xaa Xaa Xaa Xaa Gln
            20                  25                  30

<210> SEQ ID NO 68
<211> LENGTH: 33
<212> TYPE: PRT
<213> ORGANISM: Artificial Sequence
<220> FEATURE:
<223> OTHER INFORMATION: Description of Artificial Sequence: Synthetic
      MUB40 consensus sequence
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(18)
<223> OTHER INFORMATION: Any amino acid and this region may encompass 10
      to 14 residues wherein some positions may be absent
<220> FEATURE:
<221> NAME/KEY: MOD_RES
<222> LOCATION: (19)..(19)
<223> OTHER INFORMATION: Phe or Tyr
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (23)..(28)
<223> OTHER INFORMATION: Any amino acid and this region may encompass 2
      to 6 residues wherein some positions may be absent
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (31)..(31)
<223> OTHER INFORMATION: Tyr, Phe or Trp
<220> FEATURE:
<221> NAME/KEY: MOD_RES
<222> LOCATION: (32)..(32)
<223> OTHER INFORMATION: Thr, Tyr or Glu

```
<400> SEQUENCE: 68

Gly Tyr Xaa Leu Xaa Xaa Xaa Xaa Xaa Xaa Xaa Xaa Xaa Xaa Xaa
1               5                   10                  15

Xaa Xaa Xaa Asp Xaa Asp Xaa Xaa Xaa Xaa Xaa Gln Xaa Xaa Xaa
                20                  25                  30

Val

<210> SEQ ID NO 69
<211> LENGTH: 41
<212> TYPE: PRT
<213> ORGANISM: Lactobacillus reuteri
<220> FEATURE:
<223> OTHER INFORMATION: LPXTG motif

<400> SEQUENCE: 69

Ser Thr Ala Asp Gln Ile Lys Gln Leu Glu Ala Gln Gly Tyr Val Leu
1               5                   10                  15

Val Ser Asp Gly Phe Pro Ala Gly Ala Val Phe Asp Asn Asp Asn
                20                  25                  30

Thr Thr Gln Thr Tyr Thr Val Val Leu
        35                  40

<210> SEQ ID NO 70
<211> LENGTH: 41
<212> TYPE: PRT
<213> ORGANISM: Lactobacillus fermentum

<400> SEQUENCE: 70

Ser Thr Ala Ala Thr Ile Lys Gln Leu Glu Asp Gln Gly Tyr Val Leu
1               5                   10                  15

Val Ser Asn Gly Phe Pro Ala Gly Ala Val Phe Asp Asn Asp Asn
                20                  25                  30

Thr Thr Gln Thr Tyr Thr Val Val Leu
        35                  40

<210> SEQ ID NO 71
<211> LENGTH: 41
<212> TYPE: PRT
<213> ORGANISM: Lactobacillus acidophilus

<400> SEQUENCE: 71

Ser Thr Ala Asp Thr Ile Lys Asp Leu Glu Asn Lys Gly Tyr Val Leu
1               5                   10                  15

Val Asn Asp Gly Phe Pro Ala Gly Ala Lys Tyr Asp Ser Asp Asn
                20                  25                  30

Thr Thr Gln Ile Tyr Thr Val Val Leu
        35                  40

<210> SEQ ID NO 72
<211> LENGTH: 41
<212> TYPE: PRT
<213> ORGANISM: Lactobacillus crispatus

<400> SEQUENCE: 72

Ser Thr Lys Ser Thr Ile Ala Asp Leu Glu Asn Lys Gly Tyr Val Leu
1               5                   10                  15

Val Asn Asp Gly Phe Pro Ala Gly Ala Lys Phe Asp Ser Asp Asn
                20                  25                  30

Thr Thr Gln Ile Phe Thr Val Val Leu
        35                  40
```

<210> SEQ ID NO 73
<211> LENGTH: 41
<212> TYPE: PRT
<213> ORGANISM: Lactobacillus johnsonii

<400> SEQUENCE: 73

Ser Thr Ala Ser Thr Ile Glu Glu Leu Glu Asn Lys Gly Tyr Val Leu
1               5                   10                  15

Val Ser Asp Gly Phe Pro Ala Gly Ala Thr Phe Asp Asn Asp Asp Asn
            20                  25                  30

Thr Thr Gln Ile Tyr Thr Val Val Leu
        35                  40

<210> SEQ ID NO 74
<211> LENGTH: 41
<212> TYPE: PRT
<213> ORGANISM: Lactobacillus hominis

<400> SEQUENCE: 74

Ser Thr Gln Ser Thr Ile Thr Ser Leu Glu Asn Gln Gly Tyr Glu Leu
1               5                   10                  15

Val His Asp Gly Phe Pro Thr Gly Ala Thr Tyr Asp Asn Asp Asp Asn
            20                  25                  30

Thr Thr Gln Thr Tyr Thr Val Val Leu
        35                  40

<210> SEQ ID NO 75
<211> LENGTH: 41
<212> TYPE: PRT
<213> ORGANISM: Lactobacillus gasseri

<400> SEQUENCE: 75

Ser Thr Ala Asp Gln Ile Lys Lys Leu Ile Asn Gln Gly Tyr Val Leu
1               5                   10                  15

Lys Asn Asp Gly Phe Pro Ala Gly Ala Val Phe Asp Asn Asp Asp Ser
            20                  25                  30

Lys Asn Gln Val Phe Tyr Val Asp Phe
        35                  40

<210> SEQ ID NO 76
<211> LENGTH: 41
<212> TYPE: PRT
<213> ORGANISM: Lactobacillus mucosae

<400> SEQUENCE: 76

Ser Thr Ala Glu Gly Ile Lys Lys Phe Glu Gly Asp Gly Tyr Glu Leu
1               5                   10                  15

Phe Lys Asp Asn Phe Pro Ala Gly Glu Lys Phe Asp Asn Asp Asp Ala
            20                  25                  30

Asn Asp Gln Thr Tyr Thr Val Ile Phe
        35                  40

<210> SEQ ID NO 77
<211> LENGTH: 41
<212> TYPE: PRT
<213> ORGANISM: Streptococcus sp.
<220> FEATURE:
<223> OTHER INFORMATION: Streptococcus sp. C150

<400> SEQUENCE: 77

```
Ser Thr Ala Glu Arg Ile Lys His Tyr Gln Asp Leu Gly Tyr Val Leu
1               5                   10                  15

Val Thr Asp Gly Tyr Pro Ala Gly Thr Thr Phe Asp Leu Asp Ser Thr
            20                  25                  30

Val Asp Gln Ala Trp Thr Val Ser Phe
        35                  40
```

<210> SEQ ID NO 78
<211> LENGTH: 40
<212> TYPE: PRT
<213> ORGANISM: Streptococcus salivarius

<400> SEQUENCE: 78

```
Thr Ala Glu Arg Ile Lys His Tyr Gln Asp Leu Gly Tyr Ala Leu Val
1               5                   10                  15

Thr Asp Gly Tyr Pro Ala Gly Ala Ser Phe Asp Leu Asp Ser Thr Val
            20                  25                  30

Asp Gln Ala Trp Thr Val Ser Phe
        35                  40
```

<210> SEQ ID NO 79
<211> LENGTH: 38
<212> TYPE: PRT
<213> ORGANISM: Lactococcus garvieae

<400> SEQUENCE: 79

```
Thr Ser Gly Ser Ile Ala Asp Tyr Lys Lys His Gly Tyr Glu Leu Val
1               5                   10                  15

Thr Asp Gly Tyr Pro Ala Asp Leu Thr Phe Asp Asn Asp Thr Thr
            20                  25                  30

Asp Gln Asn Phe Thr Val
        35
```

<210> SEQ ID NO 80
<211> LENGTH: 39
<212> TYPE: PRT
<213> ORGANISM: Leuconostoc argentinum

<400> SEQUENCE: 80

```
Ser Thr Ser Gly Asn Ile Ala Asp Tyr Lys Lys His Gly Tyr Glu Leu
1               5                   10                  15

Val Thr Asp Gly Tyr Pro Ala Asp Leu Thr Phe Asp Asn Asp Lys
            20                  25                  30

Thr Asp Gln Asn Phe Thr Val
        35
```

<210> SEQ ID NO 81
<211> LENGTH: 38
<212> TYPE: PRT
<213> ORGANISM: Lactobacillus coryniformis

<400> SEQUENCE: 81

```
Thr Ser Gly Asn Ile Ala Asp Tyr Lys Lys Gln Gly Tyr Glu Leu Val
1               5                   10                  15

Thr Asp Gly Tyr Pro Ala Asp Leu Thr Phe Asp Asn Asp Thr Thr
            20                  25                  30

Asp Gln Asn Phe Thr Val
        35
```

<210> SEQ ID NO 82

-continued

```
<211> LENGTH: 43
<212> TYPE: PRT
<213> ORGANISM: Streptococcus cristatus

<400> SEQUENCE: 82

Ser Thr Ala Ser Arg Ile Glu Gln Leu Lys Gln Ala Gly Tyr Thr Leu
1               5                   10                  15

Val Ser Asp Gly Phe Thr Gln Pro Asn Gly Gln Lys Phe Asp Asn Asp
            20                  25                  30

Lys Thr Lys Asp Gln Thr Trp Thr Val Val Val
        35                  40

<210> SEQ ID NO 83
<211> LENGTH: 38
<212> TYPE: PRT
<213> ORGANISM: Weissella confusa

<400> SEQUENCE: 83

Thr Ala Asp Arg Ile Lys Ala Tyr Glu Ala Gln Gly Tyr Thr Leu Val
1               5                   10                  15

Ser Asp Asp Phe Pro Ala Asp Phe Gln Phe Asp Arg Asp Asp Ala Thr
            20                  25                  30

Glu Gln Lys Phe Glu Val
        35

<210> SEQ ID NO 84
<211> LENGTH: 5
<212> TYPE: PRT
<213> ORGANISM: Lactobacillus reuteri
<220> FEATURE:
<221> NAME/KEY: MOD_RES
<222> LOCATION: (3)..(3)
<223> OTHER INFORMATION: Any amino acid

<400> SEQUENCE: 84

Leu Pro Xaa Thr Gly
1               5

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Leu Cys Ile Leu Leu Ala Val Val Ala Phe Val Gly Leu Ser Leu
1               5                   10                  15

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Gly Gly Ser
1

<210> SEQ ID NO 87
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 87

Glu Asn Leu Tyr Phe Gln Ser
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Asn Leu Tyr Phe Gln Gly
1               5

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
taatgaccgg t                                                     11
```